US011136353B2

(12) United States Patent
Stover et al.

(10) Patent No.: US 11,136,353 B2
(45) Date of Patent: Oct. 5, 2021

(54) FUSION PROTEIN COMPOSITION(S) COMPRISING MASKED TYPE I INTERFERONS (IFNA AND IFNB) FOR USE IN THE TREATMENT OF CANCER AND METHODS THEREOF

(71) Applicant: Qwixel Therapeutics LLC, Los Angeles, CA (US)

(72) Inventors: David Stover, Encino, CA (US); Sherie Morrison, Los Angeles, CA (US); Alex Vasuthasawat, Los Angeles, CA (US); Kham Trinh, Porter Ranch, CA (US); George Ayoub, Los Angeles, CA (US)

(73) Assignee: Qwixel Therapeutics LLC, Los Angeles, CA (US)

( * ) Notice: Subject to any disclaimer, the term of this patent is extended or adjusted under 35 U.S.C. 154(b) by 0 days.

(21) Appl. No.: 16/849,889

(22) Filed: Apr. 15, 2020

(65) Prior Publication Data

US 2020/0331966 A1 Oct. 22, 2020

Related U.S. Application Data

(60) Provisional application No. 62/920,140, filed on Apr. 15, 2019.

(51) Int. Cl.
*C07K 7/08* (2006.01)
*A61K 47/65* (2017.01)
*A61P 35/00* (2006.01)
*A61K 38/00* (2006.01)

(52) U.S. Cl.
CPC .............. *C07K 7/08* (2013.01); *A61K 47/65* (2017.08); *A61P 35/00* (2018.01); *A61K 38/00* (2013.01)

(58) Field of Classification Search
CPC .................... C07K 7/08; A61K 47/65
See application file for complete search history.

(56) References Cited

U.S. PATENT DOCUMENTS

| | | | |
|---|---|---|---|
| 7,456,257 B2 | 11/2008 | Jones et al. | |
| 7,732,572 B2 | 6/2010 | Cox, III | |
| 7,741,449 B2 | 6/2010 | Witte et al. | |
| 8,143,026 B2 | 3/2012 | Rosen et al. | |
| 8,268,967 B2 | 9/2012 | DeFrees et al. | |
| 8,399,219 B2 | 3/2013 | Stagliano et al. | |
| 8,563,269 B2 | 10/2013 | Stagliano et al. | |
| 8,980,267 B2 | 3/2015 | Grewal et al. | |
| 8,993,266 B2 * | 3/2015 | Stagliano | C07K 14/57 435/69.51 |
| 9,139,634 B2 | 9/2015 | Morrison et al. | |
| 9,161,991 B2 | 10/2015 | Pieczykolan et al. | |
| 9,272,029 B2 | 3/2016 | Chang et al. | |
| 9,644,016 B2 * | 5/2017 | Stagliano | A61P 35/04 |
| 9,803,021 B2 | 10/2017 | Morrison | |
| 10,513,549 B2 * | 12/2019 | Stagliano | G01N 33/6866 |
| 2002/0081664 A1 | 6/2002 | Lo et al. | |
| 2004/0014652 A1 | 1/2004 | Trouet et al. | |
| 2008/0064862 A1 | 3/2008 | Harvey et al. | |
| 2008/0132681 A1 | 6/2008 | Hays et al. | |
| 2009/0028822 A1 | 1/2009 | DeFrees et al. | |
| 2009/0081218 A1 | 3/2009 | Wang et al. | |
| 2010/0189651 A1 | 7/2010 | Stagliano et al. | |
| 2010/0221212 A1 * | 9/2010 | Stagliano | C07K 16/00 424/85.4 |
| 2010/0310510 A1 | 12/2010 | Kinstler et al. | |
| 2012/0058084 A1 | 3/2012 | Rau et al. | |
| 2013/0101555 A1 | 4/2013 | Stagliano et al. | |
| 2015/0203559 A1 * | 7/2015 | Stagliano | A61K 47/64 424/85.5 |
| 2017/0240608 A1 * | 8/2017 | Stagliano | C07K 16/00 |
| 2018/0066267 A1 | 3/2018 | Puckette et al. | |
| 2020/0123227 A1 | 4/2020 | Fu et al. | |
| 2020/0308243 A1 * | 10/2020 | Stagliano | C07K 14/705 |

FOREIGN PATENT DOCUMENTS

| | | | | |
|---|---|---|---|---|
| WO | WO 2010/096838 | * | 8/2010 | ............ A61K 38/21 |
| WO | WO2011/064758 A2 | | 6/2011 | |
| WO | WO2014/166500 A2 | | 10/2014 | |
| WO | WO2015/056125 A1 | | 4/2015 | |

OTHER PUBLICATIONS

Redlich, et. al., Antibodies that Neutralize Human B Interferon Biological Activity Recognize a Linear Epitope . . . , Proc. Natl. Acad. Sci. vol. 88 pp. 4040-4044 (May 1991).
Seelig, et. al., Development of a Receptor Peptide Antagonist to Human Gamma Interferon and Characterization . . . , J. Bio. Chem. vol. 270, No. 16, pp. 9241-9249 (Apr. 21, 1995).
Erster, et. al., Site-Specific Targeting of Antibody Activity In Vivo Mediated by Disease-Associated Proteases, J. Controlled Rel. 161 (2012) 804-812.
Wong, et. al., In Vivo Imaging of Protease Activity by Probody therapeutic Activation, Biochimie 122 (2016) 62-67.
Tanimoto, et. al., Transmembrane Serine Protease TADG-15 (ST14/Matripase/MT-SP1): Expression . . . , Brit. J. Cancer (2005) 92, 278-283.
Trinh, et. al., Anti-CD20-Interferon-B Fusion Protein Therapy of Murine B Cell Lymphomas, J. Immunother (Jun. 2013) 35(5): 305-318.
Huang, et. al., Targeting IFN-A to B Cell Lymphoma by a Tumor-Specific Antibody Elicits Potent Antitumor Activities, J. Immunol. 179:6881-6888 (2007).

(Continued)

*Primary Examiner* — Amber D Steele
(74) *Attorney, Agent, or Firm* — Morrison & Foerster LLP

(57) ABSTRACT

Fusion Protein compositions comprising masked IFNs and methods of making masked IFNs are disclosed herein. Consequently, the masked IFNs can be fused to a Mab or binding fragment thereof and be administered to patients as a therapeutic modality and provide a method of treating cancer, immunological disorders and other disease.

31 Claims, 32 Drawing Sheets

Specification includes a Sequence Listing.

(56) References Cited

OTHER PUBLICATIONS

Xuan, et. al., Targeted Delivery of Interferon-A via Fusion to Anti-CD20 Results in Potent Antitumor Activity Against B-Cell Lymphoma, Blood, vol. 115, No. 14 (Apr. 2010).
Zitvogel, et. al., Type I Interferons in Anticancer Immunity, Nature Immuno. vol. 15, pp. 405-414 (Jul. 2015).
De Weerd, et. al., The Interferons and Thier Receptors—Distribution and Regulation, Immuno & Cell Bio. vol. 90, pp. 483-491 (2012).
Desnoyers, et. al., Tumor-Specific Activation of an EGFR-Targeting Probody Enhances Therapeutic Index, Sci. Transl. Med. 5, 207ra144 (2013).
Heffner, et. al., (POSTER) BT062, an Antibody-Drug Conjugate Directed Against CD138, Given Weekly for 3 Weeks in Each 4 Week Cycle: Safety and Further Evidence of . . . (2012).
Schroder, et. al., Interferon-gamma: An Overview of Signals, Mechanisms and Functions, J. Leuk. Bio. vol. 75, pp. 163-189 (Feb. 2004).
Peng, et. al., A Single-Chain IL-12 IgG3 Antibody Fusion Protein Retains antibody Specficity and IL-12 Bioactivity and Demonstrates . . . , J. Immunol. 163:250-258 (1999).
Vasuthasawat, et. al., Targeted Immunotherapy Using Anti-CD-138-Interferon A Fusion Proteins and Bortezomib . . . MAbs vol. 8, No. 7 pp. 1386-1397 (2016).
Gharbaran, Advances in the Molecular Functions of Syndecan-1 (SDC1/CD138) in the Pathogenesis . . . , Crt. Rev. Onco/Hemo 94(2015) 1-17.

* cited by examiner

Figure 1
Matripase ST 14 Cleaves an IFN Mask from the Heavy Chain of an anti-CD138 Fusion Ab.

1. anti-CD138 IFNa
2. anti-CD138 IFNa mask
3. anti-CD138 IFNa mask w/ MST14

H Chain

Matripase ST 14 Cleaves an IFN Mask from the Heavy Chain Of an anti-CD138 (N297Q) aglycosylated Fusion Ab.
1. anti-CD138 IFNα
2. anti-CD138 IFNα mask N297Q
3. anti-CD138 IFNα mask N297Q w/ MST14

Figure 3
Matripase ST 14 Cleaves an IFN Mask from the Heavy Chain of an anti-5T4 Fusion Ab and anti-mesothelin Fusion Ab.

1. anti-5T4 IFNα mask
2. anti-5T4 IFNα mask w/ MST14
3. anti-mesothelin IFNα mask
4. anti-mesothelin IFNα mask w/ MST14
5. anti-CD138 IFNα

Figure 4
Masked anti-5T4 Fusion Abs and Masked anti-mesothelin Fusion Abs Bind IFNα2 Receptor with reduced affinity relative to unmasked fusion protein Figure 5
Masked anti-CD20 Fusion Abs and Masked anti-CD138 Fusion Abs Bind IFNα2 Receptor with reduced affinity relative to un Masking Reduces IFNα Fusion Protein Activation of IFN Receptor; while MST14 Restores Activity.

*Twice as much h

Methods of Reducing and Restoring masked IFNα Activity

Induction of IP-10 in Human Peripheral Blood Mononuclear Cells ("PMBC")

Figure 9
QXL138AM: Construct Design

- Antibody: Anti-CD138 IgG1 - IFNα2- peptide (QXL138AM)
- Heavy Chain Isotype: Human Gamma 1
- Sequence:

MDPKGSLSWRILFLSLAFELSYGQVQLQQSGSELMMPGASVKISCKATGYTFSNYWI
EWVKQRPGHGLEWIGEILPGTGRTIYNEKFKGKATFTADISSNTVQMQLSSLTSEDSA
VYYCARRDYGNFYYAMDYWGQGTSVTVSSASTKGPSVFPLAPSSKSTSGGTAALGCL
VKDYFPEPVTVSWNSGALTSGVHTFPAVLQSSGLYSLSSVVTVPSSLGTQTYICNVN
HKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDI
AVEWESNGQPENNYKTTPPVLDSGSFFLYSKLTVDKSRWQQGNVFSCSVMHEALHNH
YTQKSLSLSPGSGGGSCDLPQTHSLGSRRTLMLLAQMRRISLFSCLKDRHDFGFPQE
EFGNQFQKAETIPVLHEMIQQIFNLFSTKDSSAAWDETLLDKFYTELYQQLNDLEACV
IQGVGVTETPLMKEDSIIAVRKYFQRITLYLKEKKYSPCAWEVVRAEIMRSFSLSTNL
QESLRSKEGSSGLSGRSDNHGSSGGSGGGSGIQMTQSPSSLSAGDRVTITCKASQSVSNDLAWYQQKPGKAPKLLIYSASYRYTGVPDRFSGSGGGTDFTLTISSLQPEDFATYYCQQDYSSPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC GG\*

(SEQ ID NO: 17)

- Light Chain Isotype: Human Kappa

QXL138AM: Expression / Purification Characterization

QXL138AM: Analysis of Heavy and Light Chain by Mass Spectrometer

QXL138AM: Characterization by SDS-Page

Characterization of Masked Fusion Abs by SDS-Page

Binding of Fusion Abs to Mask by ELISA

Figure 15
Characterization of Targeted Fusion Abs versus Non-Targeted Fusion Abs
(A) 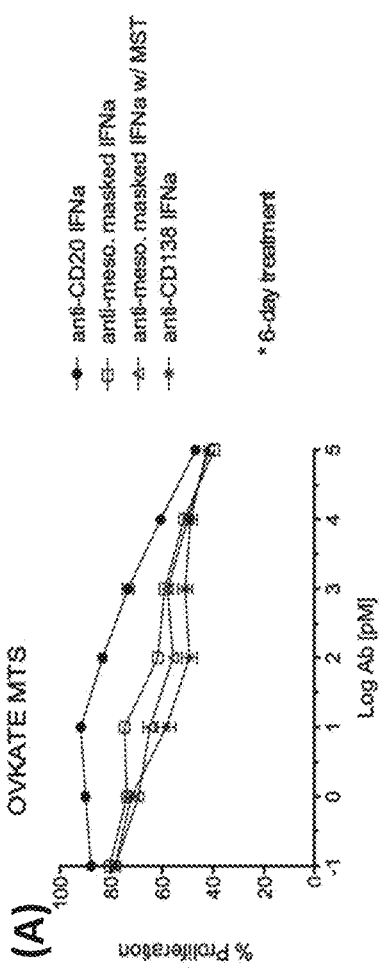
Conclusion: There's a clear targeting advantage seen between targeted vs. non-targeted fusion Ab. Although the difference is small, it appears the masked IFNa fusion Ab is less effective than the unmasked fusion Ab.
(B) 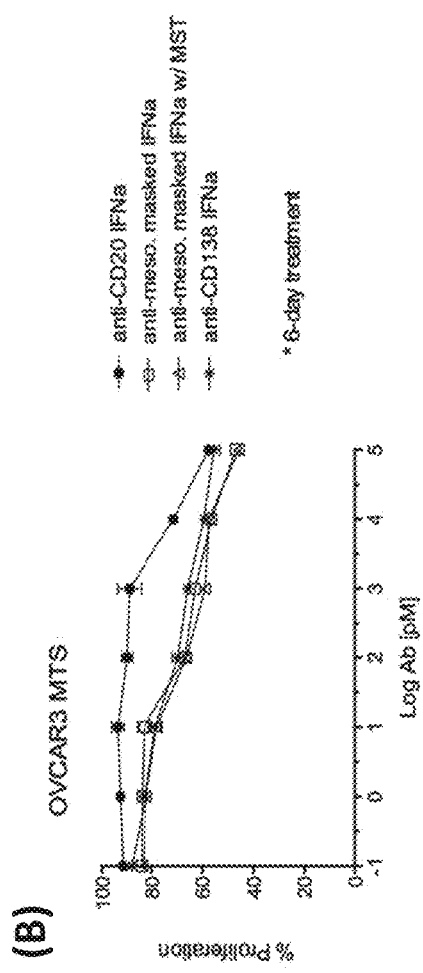
Concl

Figure 16
Characterization of Targeted Fusion Abs versus Non-Targeted Fusion Abs
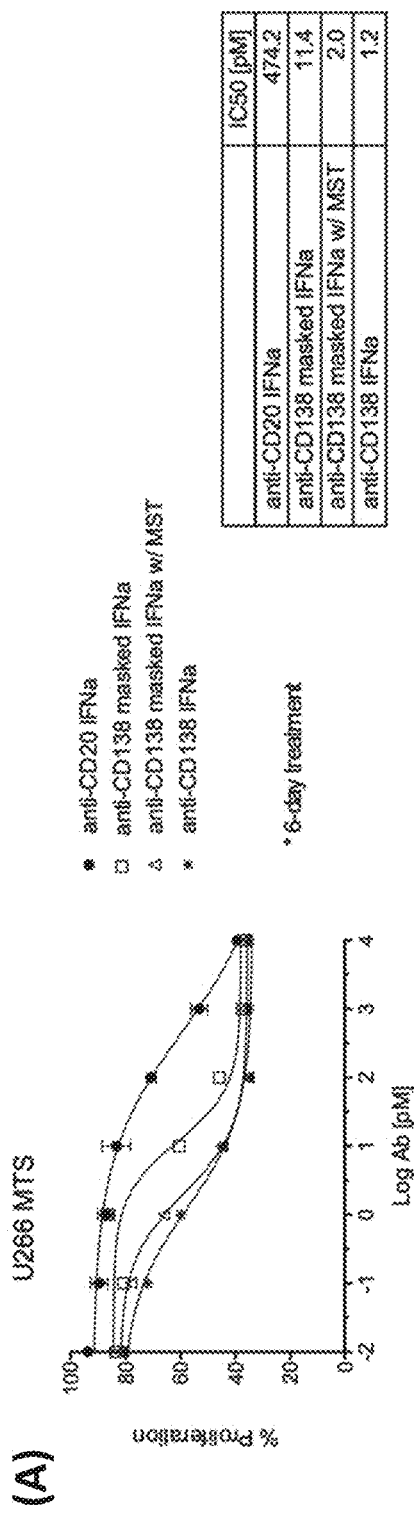
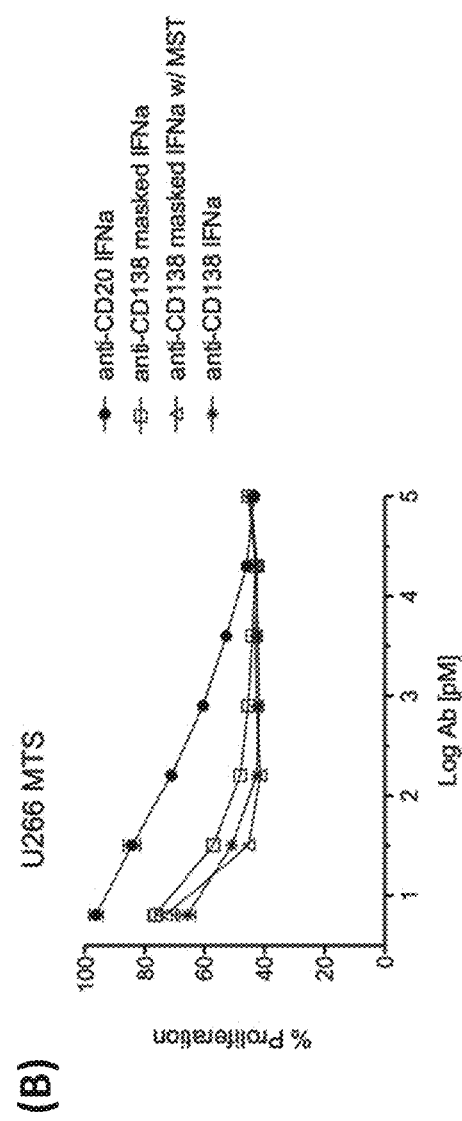
Conclusion: There's a clear targeting advantage seen between targeted vs. non-targeted fusion Ab. It also appears the masked Ab is less effective than the cleaved version.

Removal of the IFN Mask Restores Inhibition of Cell Proliferation

Tumor Cell Line Cytotoxicity of Masked/Unmasked & Targeted/Non-Targeted Fusion Abs

Tumor Cell Line Cytotoxicity of Masked/Unmasked & Targeted/Non-Targeted Fusion Abs

Masking Reduces IFNR Activation of PBMCs

Masking Reduces IFNR Activation of PBMCs

QXL138A & QXL138AM: Functional Studies *In Vitro*

QXL138A & QXL138AM: In Vivo Efficacy in Human Myeloma Xenograft (H929)

QXL138A & QXL138AM: In Vivo Efficacy in Human Myeloma Xenograft (H929)

QXL138A Shows Synergies With Standard of Care Treatment (bortezomib) in Myeloma

QXL138A Shows Synergies With Standard of Care Treatment (bortezomib) in Myeloma

QXL138AM Shows Synergies With Standard of Care Treatment (Pomalidomide) in Myeloma QXL138A Shows Synergies With Standard of Care Treatment (Pomalidomide) in Myeloma Matripase ST 14 Cleaves a Second IFN Mask from the Heavy Chain of an Masked anti-CD138 (Mask1) Fusion Abs and Masked anti-CD138 (Mask2) Fusion Abs Bind IFNα2 Receptor with reduced affinity relative to unmasked fusion protein Methods of Reducing and Restoring masked IFNα Activity

FUSION PROTEIN COMPOSITION(S) COMPRISING MASKED TYPE I INTERFERONS (IFNA AND IFNB) FOR USE IN THE TREATMENT OF CANCER AND METHODS THEREOF

CROSS-REFERENCE TO RELATED APPLICATIONS

This application claims priority to U.S. Provisional Patent Application No. 62/920,140, filed Apr. 15, 2019, the contents of which are fully incorporated by reference herein.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165802000100.txt, date recorded: Jul. 7, 2020, size: 24.7 KB).

STATEMENT OF RIGHTS TO INVENTIONS MADE UNDER FEDERALLY SPONSORED RESEARCH

Not applicable.

FIELD OF THE INVENTION

The invention described herein relates to the field of cancer therapy and therapy of other immunological disorders or diseases. Specifically, the invention relates to masked Type I interferon (IFN) compositions which can be fused to a tumor antigen binding protein and used as a vehicle for targeted cancer therapy in humans. The invention further relates to the treatment of disorders or diseases such as cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of this century, cancer is predicted to become the leading cause of death unless medical developments change the current trend.

Several cancers stand out as having high rates of mortality. Hematological malignancies, including myeloma, cause 50,000 deaths annually in the United States alone (American Cancer Society, 2018). In addition, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasize to sites distant from the primary tumor and with very few exceptions, metastatic disease is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

Furthermore, the therapeutic utility of monoclonal antibodies (mAbs) (G. Kohler and C. Milstein, Nature 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., Annual Rev. Immunol., 6:555-580 (1988)).

Additionally, the interferons, including IFNα and IFNβ (type I) and IFNγ (type II) are essential mediators of anti-cancer immunity having both direct anti-proliferative effects against many cancers as well as a multitude of anti-tumor immunotherapeutic effects. However, while IFNα has shown efficacy against multiple human cancers, its clinical utility to date has been limited by the inability to achieve effective concentrations of IFN at tumor sites without causing systemic toxicity.

Due to the systemic toxicity, several groups have approached this problem by using the tumor-targeting ability of monoclonal antibodies to carry IFNs directly to tumor sites. See, Huang, et al., J. Immunol. 179(10), pp. 6881-6888 (2007) and Vasuthasawat, et. al., J. Immunol. 36(5), pp. 305-318 (2013). It is noted that the initial work has used anti-CD20-IFNα2 proteins to target IFNα to CD20 expressed on lymphomas and anti-CD138-IFNα2 fusion proteins to target CD138 expressed on multiple myeloma. See, Vasuthasawat, et. al., MAbs 8(7), pp. 1386-1397 (2016). While these approaches have shown great therapeutic promise and are currently being tested in human clinical trials and developed commercially, there are several deficiencies.

While it is noted that using the antibody binding specificity to target tumor-associated antigens delivers a greater percentage (%) of the IFN to the site of the tumor than is achieved when IFN is injected on its own, the attached interferon still is recognized and bound by interferon receptors expressed throughout the body that are not tumor associated. Thus, Mab-fused IFN may still induce toxicity and/or have increased clearance due to the systemic exposure and interaction with IFN receptors throughout the body.

From the aforementioned, it will be readily apparent to those skilled in the art that a new treatment paradigm is needed in the treatment of cancers and immunological diseases.

Given the current deficiencies associated with delivering IFN to a cancer cell, it is an object of the present invention to provide new and improved methods of treating cancer(s), immunological disorders, and other diseases utilizing a masked IFN that inhibits the activity of IFN until it reaches the tumor. Provided are compositions, kits and methods for use that meet such needs.

SUMMARY OF THE INVENTION

The invention provides for antibodies, antigen-binding fragments, and fusion protein compositions that bind to a full range of tumor associated antigens (TAAs). In a further embodiment, the fusion protein compositions comprise a type I Interferon. In a further embodiment, the IFN is masked so its activity is reduced or nullified until it reaches a tumor cell. In a further embodiment, the TAA is set forth in Table I. In a preferred embodiment, the TAA is associated with a solid tumor. In one embodiment, the TAA comprises CD138. In a further embodiment, the TAA is CD20. In a further embodiment, the TAA is mesothelin. In another embodiment, the TAA is 5T4. In yet another embodiment, the IFN or functionally active mutants are set forth in Table II. In a preferred embodiment, the IFN comprises IFNA2.

In a further embodiment, the invention comprises a targeted masked IFN. In a preferred embodiment, the targeted masked IFN comprises IFNA1.

In a further embodiment, the invention comprises a targeted masked IFN. In a preferred embodiment, the targeted masked IFN comprises IFNA14.

In a further embodiment, the invention comprises a targeted masked IFN. In a preferred embodiment, the targeted masked IFN comprises IFNB1.

In another embodiment, the present disclosure teaches methods of producing a targeted masked IFN.

In another embodiment, the present disclosure teaches methods of treating cancer(s), immunological disorders and other diseases in humans.

In a preferred embodiment, the present disclosure teaches methods of treating cancer with a masked IFN which is fused to a MAb which binds a TAA.

In some of any of the embodiments, the methods for treating a cancer involves administering to a subject, such as a human subject, a therapeutically effective amount of any of the compositions or any of the fusion proteins, such as any of the targeted Masked IFNs described herein.

Also provided are pharmaceutical compositions comprising a therapeutically effective amount of any of the compositions or any of the fusion proteins, such as any of the targeted Masked IFNs described herein. In some of any of the embodiments, the pharmaceutical composition is for use in therapy including treatment of cancer. In some of any of the embodiments, the cancer comprises a cancer found in a solid tumor; or the cancer arises in the hematopoietic system. In some of any of the embodiments, the pharmaceutical composition further comprises one or more anti-neoplastic agents.

Also provided are kits, such as kits comprising any of the compositions or any of the fusion proteins, such as any of the targeted Masked IFNs described herein.

BRIEF DESCRIPTION OF THE FIGURES

FIG. 1. Matriptase ST 14 Cleaves an IFN Mask from the Heavy Chain of an anti-CD138 Fusion Ab.

FIG. 3. Matriptase ST 14 Cleaves an IFN Mask from the Heavy Chain of an anti-5T4 Fusion Ab & anti-mesothelin Fusion Ab.

FIG. 4. Masked anti-5T4 Fusion Abs and Masked anti-mesothelin Fusion Abs Bind IFNα2 Receptor with reduced affinity relative to unmasked fusion protein.

FIG. 5. Masked anti-CD20 Fusion Abs and Masked anti-CD138 Fusion Abs Bind IFNα2 Receptor with reduced affinity relative to unmasked fusion protein.

FIG. 7(A) shows anti-5T4 Fusion Abs. FIG. 7(B) shows anti-mesothelin Abs.

FIG. 9. QXL138AM Construct Design.

FIG. 14(A) shows binding to Mask (Peptide 1). FIG. 14(B) shows binding to Mask (Peptide 2).

FIG. 15(A-B). Characterization of Targeted Fusion Abs Versus Non-Targeted Fusion Abs. FIG. 15(A) shows proliferation in OVKATE cells. FIG. 15(B) shows proliferation in OVCAR3 cells.

FIG. 16(A-B). Characterization of Targeted Fusion Abs Versus Non-Targeted Fusion Abs. FIG. 16(A) shows proliferation in U266 MTS cells. FIG. 16(B) shows proliferation in U266 MTS cells.

FIG. 32(A) shows anti-CD138 Fusion Abs (Mask1 and Mask2) without MST. FIG. 32(B) shows anti-CD138 Fusion (Mask1 and Mask2) with MST.

DETAILED DESCRIPTION OF THE INVENTION

Figure 2:
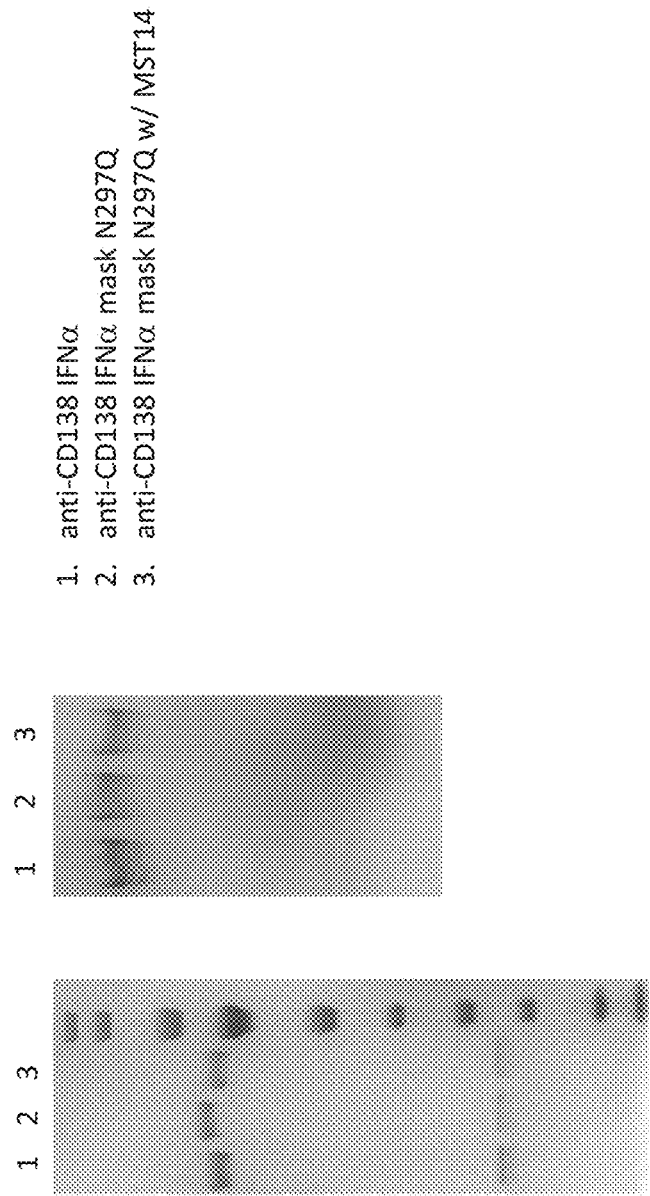
FIG. 2. Matriptase ST 14 Cleaves an IFN Mask from the Heavy Chain of an anti-CD138 (N297Q) aglycosylated Fusion Ab.

Provided herein are fusion proteins and compositions comprising an interferon (IFN). In some aspects, the provided fusion proteins and compositions comprise an IFN and an antibody or an antigen-binding fragment thereof, such as an antibody or antigen-binding fragment thereof that is specific for a tumor-associated antigen (TAA). In some embodiments, the interferon is a Type I IFN. In some aspects, the provided fusion proteins and compositions comprise an IFN and a mask, such as a polypeptide sequence that blocks the interaction between the IFN and its receptor, e.g., an IFN-α receptor (IFNAR). In some aspects, the provided fusion proteins or compositions comprise an IFN, an antibody or antigen-binding fragment thereof and a mask. In some of any of the provided embodiments, the fusion proteins or compositions also contain a flexible peptide linker. In some embodiments, the fusion proteins or compositions also contain a protease cleavage site, such as a tumor associated protease cleavage site. In some aspects, the cleavage of the protease cleavage site, for example at or near the site of the tumor or in the tumor microenvironment (TME), can lead to an "unmasking" of the IFN and permit binding of the IFN to its receptor. In some aspects, the antibody or antigen-binding fragment thereof, e.g., that is specific for a TAA, can target the fusion protein or composition, to particular sites or location of tumor or cancer. Accordingly, in some aspects, the provided fusion proteins and compositions can be used for treating a disease or disorder, such as a cancer or a tumor. Also provided are methods of making such fusion proteins or compositions, methods related to using such fusion proteins or compositions, such as in a method of treatment or in a therapeutic method, and pharmaceutical compositions or kits comprising such fusion proteins or compositions.

As described further herein, the provided embodiments, including the targeted masked IFNs, provide a unique advantage over available approaches for several reasons, including a masked IFN whose activity is significantly reduced and/or eliminated until it reaches the site of the tumor, so that non-specific activity is minimized and the fusion protein is not trapped by interferon receptors that are not at the tumor site. At the site of the tumor, the mask can be removed and the binding and activity of the IFN is re-activated, which can maximize the efficacy in the tumor, and increase the effective concentration of the fusion protein without increasing the toxicity. In addition, by virtue of the antibody that is attached to the IFN, the fusion protein can be targeted to a specific tumor (e.g., a tumor that expresses the TAA specifically bound by the antibody). The specific targeting allows for greater opportunity that the IFN will be directed to the cancer of interest and avoid non-cancerous or non-tumorous tissue.

Outline of Sections
I.) Definitions
II.) Antibodies
III.) Interferon(s)
IV.) Methods of Masking IFNs
  a. Discussion of Available Approaches
  b. Methods of Masking IFN of the Disclosure
V.) Treatment of Cancer(s) Expressing a Tumor Associates Antigen (TAA)
VI.) Targeted Masked IFN Fusion Protein Cocktails
VII.) Combination Therapy
VIII.) KITS/Articles of Manufacture All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I.) Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. Edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

"Altering the native glycosylation pattern" is intended for purposes herein to mean deleting one or more carbohydrate moieties found in native antibody sequence (either by removing the underlying glycosylation site or by deleting the glycosylation by chemical and/or enzymatic means), and/or adding one or more glycosylation sites that are not present in the native antibody sequence, wherein the "native glycosylation pattern" refers to the natural post-translational glycosylation pattern resulting from a particular combination of an antibody sequence, cell type, and growth conditions used. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a TAA-related protein). For example, an analog of a TAA protein can be specifically bound by an antibody or T cell that specifically binds to a TAA.

The term "antibody" is used in the broadest sense unless clearly indicated otherwise. Therefore, an "antibody" can be naturally occurring or man-made such as monoclonal antibodies produced by conventional hybridoma or transgenic mice technology. Antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds to a TAA and/or exhibits the desired biological activity and specifically covers monoclonal antibodies (including full length monoclonal antibodies), polyclonal antibodies, multi-specific antibodies (e.g., bispecific antibodies), and antibody fragments so long as they specifically bind a TAA and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is an IgG1, IgG2, IgG3, IgG4 antibody or any known antibody isotype. The antibodies useful in the present methods and compositions can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and at least one VH region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); Goding, MONOCLONAL ANTIBODIES: PRINCIPLES AND PRACTICE (Academic Press, 1993); and CURRENT PROTOCOLS IN IMMUNOLOGY (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective TAA. See e.g., ANTIBODY ENGINEERING: A PRACTICAL APPROACH (Oxford University Press, 1996). Suitable antibodies with the desired biologic activities can be identified using the following in vitro assays including but not limited to: proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the TAA or its receptor.

The term "antigen-binding fragment" or "antibody fragment" of an antibody (or simply "antibody portion"), as used herein, refers to one or more fragments of a TAA antibody that retain the ability to specifically bind to a TAA antigen (e.g., CD138, CD20, mesothelin, 5T4 and variants thereof; see also, Table I). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The term "Fc", as used herein, refers to a region comprising a hinge region, CH2 and/or CH3 domains.

As used herein, any form of the "antigen" can be used to generate an antibody that is specific for a TAA. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain or intracellular domain. As used herein, the term "portion", in the context of an antigen, refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the TAA of interest.

The antibodies or antigen binding fragments thereof provided herein may constitute or be part of a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade.

As used herein, the term "conservative substitution" refers to substitutions of amino acids and/or amino acid sequences that are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., MOLECULAR BIOLOGY OF THE GENE, The Benjamin/Cummings Pub. Co., p. 224 (4th Edition 1987)). Such exemplary substitutions are preferably made in accordance with those amino acids set forth in Table(s) III. For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine; and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g. Table III herein; pages 13-15 "Biochemistry" 2nd ED. Lubert Stryer ed. (Stanford University); Henikoff et al.; PNAS 1992 Vol 89 10915-10919; Lei et al., J Biol Chem 1995 May 19; 270(20):11882-6). Other substitutions are also permissible and may be determined empirically or in accord with known conservative substitutions.

The term "fusion protein" as used herein means a protein of the invention which is fused to an IFN of the invention at the C-terminus using the linkers and methods known in the art. See, for example, U.S. Pat. No. 9,803,021, which is incorporated by reference herein. Exemplary linkers which can be used to fuse an IFN to a protein of the invention include, but are not limited to: (i) GGGGSGGGGSGGGGS (SEQ ID NO: 1); (ii) GGGGS (SEQ ID NO: 2); (iii) SGGGGS (SEQ ID NO: 3); AGAAAKGAAAKAG (SEQ ID NO: 4); SGGAGGS (SEQ ID NO: 5); Landar; Double Landar; 1qo0E_1; IgG3 hinge; IgG3 hingeΔcys; and/or IgG1 hingeΔcys.

The terms "inhibit" or "inhibition of" as used herein means to reduce by a measurable amount, or to prevent entirely.

The term "interferon" as used herein means a group of signaling proteins made and released by host cells in response to the presence of several viruses. In a typical scenario, a virus-infected cell will release interferons causing nearby cells to heighten their anti-viral defenses. IFNs belong to the large class of proteins known as cytokines, molecules used for communication between cells to trigger the protective defenses of the immune system that help eradicate pathogens.

The term "Type 1 interferon" or "Type I interferon" as used herein means a large subgroup of interferon proteins that help regulate the activity of the immune system. All type I IFNs bind to a specific cell surface receptor complex known as the IFN-α receptor (IFNAR) that consists of IFNAR1 and IFNAR2 chains. An exemplary list of type I interferons of the present disclosure are set forth in Table II.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The term "mask" in referring to a masked IFN (also denoted as "masked" IFN) means for purposes of this invention, any peptide or protein that blocks cytokine interaction and/or activation of IFNAR. It is within the scope of the invention that "mask" can be modified by substitutions using recombinant means. The modification in amino acids includes deletions, additions, and substitutions of amino acids.

The term "targeted masked IFN" as used herein means a type I interferon in which a polypeptide is attached at the carboxy terminus of the IFN thereby reducing the ability to bind the IFNAR. The masked IFN further comprises attachment to the carboxy terminus of a targeted binding protein (i.e. antibody). It is within the scope of the invention that "targeted masked IFN(s) can be modified by substitutions using recombinant means. The modification in amino acids includes deletions, additions, and substitutions of amino acids.

The terms "metastatic cancer" and "metastatic disease" mean cancers that have spread to regional lymph nodes or to distant sites, and are meant to include stage D disease under the AUA system and stage T×N×M+ under the TNM system.

"Molecular recognition" means a chemical event in which a host molecule is able to form a complex with a second molecule (i.e. the guest). This process occurs through non-covalent chemical bonds, including but not limited to, hydrogen bonding, hydrophobic interactions, ionic interaction.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example. These monoclonal antibodies will usually bind with at least a Kd of about 1 µM, more usually at least about 300 nM, typically at least about 30 nM, preferably at least about 10 nM, more preferably at least about 3 nM or better, usually determined by ELISA.

"Pharmaceutically acceptable" refers to a non-toxic, inert, and/or composition that is physiologically compatible with humans or other mammals.

As used herein, the term "single-chain Fv" or "scFv" or "single chain" antibody refers to antibody fragments comprising the $V_H$ and $V_L$ domains of antibody, wherein these domains are present in a single polypeptide chain. Generally; the Fv polypeptide further comprises a polypeptide linker between the $V_H$ and $V_L$ domains which enables the scFv to form the desired structure for antigen binding. For a review of scFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds a TAA antigen but does not bind to the irrelevant antigen. In another embodiment, a specific antibody is one that binds human TAA antigen but does not bind a non-human TAA antigen with 70%, 75%, 80%, 85%, 90%, 91%, 92%, 93%, 94%, 95%, 96%, 97%, 98%, 99% or greater amino acid homology with the TAA antigen. In another embodiment, a specific antibody is one that binds human TAA antigen but does not bind a non-human TAA antigen with 70%, 75%, 80%, 85%, 90%, 91%, 92%, 93%, 94%, 95%, 96%, 97%, 98%, 99% or greater percent identity with the amino acid sequence of the TAA antigen. In another embodiment, a specific antibody is one that binds human TAA antigen and binds murine TAA antigen, but with a higher degree of binding the human antigen. In another embodiment, a specific antibody is one that binds human TAA antigen and binds primate TAA antigen, but with a higher degree of binding the human antigen. In another embodiment, the specific antibody binds to human TAA antigen and any non-human TAA antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

II.) Antibodies

In some embodiments, the provided fusion proteins, such as a targeted masked interferon (IFN), and compositions, comprise an antibody or an antigen-binding fragment thereof. In some of any of the provided embodiments, the antibody binds, such as specifically binds, recognizes, targets an antigen that is an antigen that is associated with a disease or a disorder, such as a cancer or an immunological disorder or disease, such as a tumor associated antigen (TAA). In some aspects, by virtue of the binding of to the antigen (e.g., TAA), the provided fusion protein, such as the targeted masked IFN, can be targeted to the relevant physical location for the therapy, such as regions of the cancer or the tumor. In some aspects, the described antibody or antigen-binding fragment thereof can be used as the component for any of the fusion proteins provided herein, for example, in any of the targeted IFN, antibody-IFN fusion protein or targeted masked IFN, provided herein.

An aspect of the invention provides antibodies that bind to an antigen associated with a cancer or tumor, such as a tumor associated antigen (TAA) and TAA-related proteins (See, Table I ), in one embodiment, the antibody that binds to a TAA related protein is an antibody that specifically binds to a TAA protein comprising an amino acid of the proteins set forth in Table 1. For example; antibodies that bind a TAA protein comprising the amino acid sequence of one of the proteins set forth in Table I can bind TAA-related proteins such as TAA variants and the homologs or analogs thereof.

In some aspects, antibodies that bind to a TAA or a TAA-related protein, such as anti-TAA antibodies of the provided embodiments are particularly useful in cancer, for prognostic assays; imaging, diagnostic, and therapeutic methodologies. In some aspects, the antibodies of the provided embodiments are therapeutic antibodies, e.g., therapeutic antibodies that specifically bind a TAA, such as a TAA set forth in Table I. Similarly, such antibodies are useful (e.g. when combined with a therapeutic agent; in a fusion protein, in the treatment, and/or prognosis of cancers, such as ovarian, head and neck, multiple myeloma, and other cancers, to the extent TAA is also expressed or overexpressed in these other cancers. Moreover, antibodies of the provided embodiments, including intracellularly expressed antibodies (e.g., single chain antibodies) are therapeutically useful in treating cancers in which the expression of TAA is involved, such as advanced or metastatic cancers in solid tumors or other advanced or metastatic cancers. In one embodiment is a TAA binding assay disclosed herein for use in detection of cancer, for example, in an immunoassay.

In some embodiments, the provided fusion protein or composition comprises an antibody that binds a Tumor Associated Antigen (TAA), for example a TAA selected from exemplary TAAs set forth in Table I. In some embodiments, the TAA is an antigen expressed on the surface of a tumor, such as the surface of a tumor cell or a cancer cell. In some embodiments, the TAA includes any antigen associated with any of the disease or conditions described herein, such as any cancer described herein. In some embodiments, the TAA is an antigen that is expressed on the surface of a cell associated with a tumor, such as cells present in the tumor microenvironment (TME). In some embodiments, the TAA is an antigen that is present in the TME.

In some embodiments, the provided fusion protein or composition comprises an antibody which binds a Tumor Associated Antigen associated with tumors arising in the hematopoietic system, such as a hematological malignancy. In some embodiments, the provided fusion protein or composition comprises an antibody that binds to a CD138 antigen. In some embodiments, the antibody binds to, such as specifically binds to, one of the TAA set forth in Table I.

In some embodiments, the antibody comprises or is comprised in a fusion protein. In some embodiments, the antibody is comprised in any of the fusion proteins or compositions provided herein. In some embodiments, the antibody comprises a fusion protein which comprises a Type-1 IFN, such as a Type I IFN set forth in Table II. In some embodiments, the antibody comprises a fusion protein, further comprising targeted IFN-alpha. In some embodiments, the antibody comprises a fusion protein, further comprising a targeted masked IFN-alpha.

In some aspects, the antibody includes an antibody fragment, such as an antigen-binding antibody fragment. Examples of antibody fragments include but are not limited to, Fab fragments, Fab' fragments, F(ab)'$_2$ fragments, single-chain antibody molecules, e.g., single chain Fv proteins ("scFv"), disulfide stabilized Fv proteins ("dsFv"), Fv, Fab'-SH, diabodies, linear antibodies, and multi-specific antibodies formed from antibody fragments.

Various methods for the preparation of antibodies, such as monoclonal antibodies, are well known in the art. For example, antibodies can be prepared by immunizing a suitable mammalian host using a TAA-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of TAA can also be used, such as a TAA GST-fusion protein. In a particular embodiment, a GST fusion protein comprising all or most of the amino acid sequence of FIG. 1 is produced, and then used as an immunogen to generate appropriate antibodies. In another embodiment, a TAA-related protein is synthesized and used as an immunogen.

In addition, naked DNA immunization techniques known in the art are used (with or without purified TAA-related protein or TAA expressing cells) to generate an immune response to the encoded immunogen (for review, see Donnelly et al., 1997, Ann. Rev. Immunol. 15: 617-648).

The amino acid sequence of a TAA protein set forth in Table I can be analyzed to select specific regions of the TAA protein; for example as an immunogen or an epitope, for generating antibodies. For example, hydrophobicity and hydrophilicity analyses of a TAA amino acid sequence are used to identify hydrophilic regions in the TAA structure. Regions of a TAA protein that show immunogenic structure, as well as other regions and domains, can readily be identified using various other methods known in the art, such as Chou-Fasman, Gamier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad, Sci, U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin 1, 1979, Nature 277:491-492, Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Preferred methods for the generation of TAA ant bodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances, linking reagents such as those supplied by Pierce Chemical Co., Rockford, Ill., are effective. Administration of a TAA immunogen is often conducted by injection over a suitable time period and with use of a suitable adjuvant, as is understood in the art. During the immunization schedule, titers of antibodies can be taken to determine adequacy of antibody formation.

TAA monoclonal antibodies can be produced by various means well known in the art. For example, immortalized cell lines that secrete a desired monoclonal antibody, are prepared using the standard hybridoma technology of Kohler and Milstein or modifications that immortalize antibody-producing B cells, as is generally known, Immortalized cell lines that secrete the desired antibodies are screened by immunoassay in which the antigen is a TAA-related protein. When the appropriate immortalized cell culture is identified, the cells can be expanded, and antibodies produced either from in vitro cultures or from ascites fluid.

The antibodies or fragments of the invention can also be produced by recombinant means, Regions that bind specifically to the desired regions of a TAA protein can also be produced in the context of chimeric or complementarity-determining region (CDR) grafted antibodies of multiple species origin. Humanized or human TAA antibodies can also be produced and are preferred for use in therapeutic contexts, Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993. J. Immunol, 151: 2296.

In one embodiment, human monoclonal antibodies of the invention can be prepared using VelocImmune mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586, 251, 6,596,541, 7,105,348, 6,528,313, 6,638,768, and 6,528, 314.

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al, (1994) Nature 368(6474): 856-859).

In another embodiment, fully human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", such mice are described in Tomizuka et al. (2000) Proc. Natl. Acad. Sci. USA 97:722-727 and POT Publication WO 02/43478 to Tomizuka, et al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6; 544; 731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson, et al.

Additionally, human antibodies of the present invention can be made with techniques using transgenic mice, inactivated for antibody production, engineered with human heavy and light chains loci referred to as Xenomouse (Amgen Fremont, Inc., formerly Abgenix, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and Mendez, et. al. Nature Genetics, 15: 146-156 (1998); Kellerman, S. A, & Green, L. L., Curr. Opin. Biotechnol 13, 593-597 (2002).

Any of the methods of production above result in antibodies that have a certain ability to bind TAA, or homologs or fragments or polypeptide sequences having 85, 90, 91; 92, 93, 94, 95, 96, 9, 98, or 99% sequence identity to TAA. The binding affinity ($K_D$) of the antibodies, binding fragments thereof, and antibody drug conjugates comprising the same for TAA may be 1 mM or less; 100 nM or less, 10 nM or less, 2 nM or less or 1 nM or less. Alternatively, the $K_D$ may be between 5 and 10 nM; or between 1 and 2 nM. The K may be between 1 micromolar and 500 micromolar or between 500 micromolar and 1 nM.

The binding affinity of the antigen binding protein is determined by the association constant (Ka) and the dissociation constant (Kd) (KD=Kd/Ka). The binding affinity may be measured by BIACORE for example, by capture of the test antibody onto a protein-A coated sensor surface and flowing TAA over this surface. Alternatively, the binding affinity can be measured by FORTEBIO for example, with the test antibody receptor captured onto a protein-A coated needle and flowing TAA over this surface. One of skill in the art can identify other suitable assays known in the art to measure binding affinity.

The term "specifically binds", as used herein in relation to TAA antigen binding, proteins means that the antigen binding protein binds to the TAA as well as a discrete domain, or discrete amino acid sequence, within a TAA with no or insignificant binding to other (for example, unrelated) proteins. This term, however, does not exclude the fact that the antibodies or binding fragments thereof may also be cross-reactive with closely related molecules. The antibodies and fragments thereof as well as fusion proteins comprising these described herein may specifically bind to a TAA with at least 2, 5, 10, 50, 100, or 1000-fold greater affinity than they bind to closely related molecules.

In one aspect, the invention comprises an antibody which binds a Tumor Associated Antigen (TAA).

In another aspect, the invention comprises an antibody which binds a Tumor Associated Antigen (TAA) associated with a solid cancer tumor.

In another aspect, the invention comprises an antibody which binds a Tumor Associated Antigen associated with tumors arising in the hematopoietic system.

In another aspect, the invention comprises an antibody which binds to a CD138 antigen.

In another aspect, the invention comprises an antibody which binds to a CD20 antigen.

In another aspect, the invention comprises an antibody which binds to a mesothelin antigen.

In another aspect, the invention comprises an antibody which binds to a 5T4 antigen.

In another aspect, the invention comprises an antibody which binds to a PSCA antigen.

In another aspect, the antibody comprises a fusion protein.

In another aspect, the antibody comprises a fusion protein which comprises a type 1 IFN set forth in Table II.

In another aspect, the antibody comprises a fusion protein, further comprising targeted IFN-alpha.

In another aspect, the antibody comprises a fusion protein, further comprising a targeted masked IFN-alpha.

In another aspect, the invention comprises an antibody which binds CD138 which further comprises a heavy chain with the following sequence:

```
                                              (SEQ ID NO: 6)
MDPKGSLSWRILLFLSLAFELSYGQVQLQQSGSELMMPGASVKI

SCKATGYTFSNYWIEWVKQRPGHGLEWIGEILPGTGRTIYNEKF

KGKATFTADISSNTVQMQLSSLTSEDSAVYYCARRDYYGNFYYA

MDYWGQGTSVTVSSASTKGPSVFPLAPSSKSTSGGTAALGCLVK

DYFPEPVTVSWNSGALTSGVHTFPAVLQSSGLYSLSSVVTVPSS

SLGTQTYICNVNHKPSNTKVDKKVEPKSCDKTHTCPPCPAPELL

GGPSVFLFPPKPKDTLMISRTPEVTCVVVDVSHEDPEVKFNWYV

DGVEVHNAKTKPREEQYNSTYRVVSVLTVLHQDWLNGKEYKCKV

SNKALPAPIEKTISKAKGQPREPQVYTLPPSRDELTKNQVSLTC

LVKGFYPSDIAVEWESNGQPENNYKTTPPVLDSDGSFFLYSKLT

VDKSRWQQGNVFSCSVMHEALHNHYTQKSLSLSPG.
```

In another aspect, the invention comprises an antibody which binds CD138 which further comprises a heavy chain with the following sequence:

(SEQ ID NO: 21)
QVQLQQSGSELMMPGASVKISCKATGYTFSNYWIEWVKQRPGHG

LEWIGEILPGTGRTIYNEKFKGKATFTADISSNTVQMQLSSLTS

EDSAVYYCARRDYYGNFYYAMDYWGQGTSVTVSSASTKGPSVFP

LAPSSKSTSGGTAALGCLVKDYFPEPVTVSWNSGALTSGVHTFPA

VLQSSGLYSLSSVVTVPSSSLGTQTYICNVNHKPSNTKVDKKVE

PKSCDKTHTCPPCPAPELLGGPSVFLFPPKPKDTLMISRTPEVT

CVVVDVSHEDPEVKFNWYVDGVEVHNAKTKPREEQYNSTYRVVS

VLTVLHQDWLNGKEYKCKVSNKALPAPIEKTISKAKGQPREPQV

YTLPPSRDELTKNQVSLTCLVKGFYPSDIAVEWESNGQPENNYK

TTPPVLDSDGSFFLYSKLTVDKSRWQQGNVFSCSVMHEALHNHY

TQKSLSLSPG.

III.) Interferon(s)

In some embodiments, the provided fusion proteins, such as a targeted interferon (IFN), e.g., a targeted masked IFN, and compositions, comprise a component that is an interferon (IFN) or a variant thereof. In some aspects, also provided are targeted masked IFNs, such as a Type I IFN that is fused with an antibody or a fragment or a chain thereof, and an "interferon mask."

In some embodiments, provided are fusions proteins comprising an interferon (IFN) or a variant thereof, and an antibody or antigen-binding fragment thereof that specifically binds a tumor associated antigen (TAA), such as an antibody-IFN fusion protein or a targeted IFN. In some aspects, the IFN is any type of IFN described herein. In particular aspects, exemplary of IFN in the provided embodiments include Type I IFNs, including any known Type I IFNs and any described herein, such as those set forth in Table II. Exemplary antibodies in the fusion protein include any described herein, for example, in Section II or Table I. In some of any of the embodiments, provided are interferons (IFNs) or a variant thereof that is attached to or connected to a "mask", such as a peptide or protein that blocks cytokine interaction and/or activation of interferon α α receptor (IFNAR); also in some cases referred to as an interferon mask. In some aspects, provided are masked IFNs. In some aspects, exemplary of IFN in the provided masked IFN include Type I IFNs, including any known Type I IFNs and any described herein, such as those set forth in Table II. Exemplary masks and methods for masking an interferon include any described herein, e.g., in Section IV. In some embodiments, the antibody-IFN fusion protein comprises a "masked" IFN that comprises an IFN component that is selected from the IFN in Table II.

In some aspects, IFNs are proteins used for therapy or treatment of a disease or disorder. In some aspects, the provided fusion proteins and compositions contain the IFN component that can be effective in treating a disease or disorder, such as a cancer or a tumor, and/or can be used to increase the effectiveness of a therapeutic agent, such as an anti-cancer or anti-neoplastic agent.

IFNs are a group of signaling proteins made and released by the cells of a subject or host, such as host cells, in response to the presence of foreign entities in the body, such as a pathogen, including several viruses. In a typical scenario, a virus-infected cell will release interferons causing nearby cells to heighten their anti-viral defenses.

IFNs belong to the large class of proteins known as cytokines, molecules used for communication between cells to trigger the protective defenses of the immune system that help eradicate pathogens. Interferons are named for their ability to "interfere" with viral replication by protecting cells from virus infections. In some aspects, IFNs also have various other functions: (i) they activate immune cells, such as natural killer cells and macrophages: and (ii) they increase host defenses by up-regulating antigen presentation by virtue of increasing the expression of major histocompatibility complex (MHC) antigens.

More than twenty (20) distinct IFN genes and proteins have been identified in animals, including humans. They are typically divided among three classes: Type I IFN, Type II IFN, and Type III IFN. IFNs belonging to all three classes are important for fighting viral infections and for the regulation of the immune system.

Interferon Type I:

All type I IFNs bind to a specific cell surface receptor complex known as the IFN-α/β receptor (IFNAR) that consists of IFNAR1 and IFNAR2 chains. There are thirteen (13) type I interferons present in humans including, but not limited to IFN-α, IFN-β, IFN-ε, IFN-κ and IFN-ω. In general, type 1 interferons are produced when the body recognizes a virus that has invaded it. They are produced by fibroblasts and monocytes. However, the production of type I IFN-α is prohibited by another cytokine known as Interleukin-10. Once released, type I interferons bind to specific receptors on target cells, which leads to expression of proteins that will prevent the virus from producing and replicating its RNA and DNA.

Interferon type II (IFN-γ in humans): This is also known as immune interferon and is activated by Interleukin-12. Furthermore, type II interferons are released by cytotoxic T cells and T helper cells, Type I specifically. However, they block the proliferation of T helper cells type two. The previous, results in an inhibition of $T_h2$ immune response and a further induction of $T_h1$ immune response, which leads to the development of debilitating diseases, such as multiple sclerosis. IFN Type II binds to IFNGR, which consists of IFNGR1 and IFNGR2 chains.

Interferon type III: Signal through a receptor complex consisting of IL10R2 (also called CRF2-4) and IFNLR1 (also called CRF2-12). Recent information demonstrates the importance of Type III IFNs in some types of virus or fungal infections.

In general, type I and II interferons are responsible for regulating and activating the immune response. Expression of type I and III IFNs can be induced in virtually all cell types upon recognition of viral components, especially nucleic acids, by cytoplasmic and endosomal receptors, whereas type II interferon is induced by cytokines such as IL-12, and its expression is restricted to immune cells such as T cells and NK cells.

In some aspects, IFNs and proteins containing or derived from IFNs can be used as a therapeutic agent. In some of any of the provided embodiments, the IFN component of the fusion protein, e.g., targeted masked IFN, is used as a therapeutic agent for treatment of the disease or disorder, such as a cancer.

In some aspects, Interferon therapy is used (in combination with chemotherapy and radiation) as a treatment for some cancers. This treatment can be used in hematological malignancy; leukemia and lymphomas including hairy cell leukemia, chronic myeloid leukemia, nodular lymphoma, and cutaneous T-cell lymphoma. In some instances, patients with recurrent melanomas receive recombinant IFN-α2b.

A major limitation with using available IFN in cancer therapy has been the inability to achieve effective concentrations of IFN at tumor sites without causing systemic toxicity. In order to overcome this limitation, several attempts have been made to solve this problem, by using the tumor targeting ability of monoclonal antibodies to carry IFNs directly to the tumor sites. See, Huang, et al., J. Immunol. 179(10), pp. 6881-6888 (2007) and Vasuthasawat, et. al., J. Immunol. 36(5), pp. 305-318 (2013). It is noted that the initial work has used anti-CD20-IFNα2 proteins to target IFNα to CD20 expressed on lymphomas and anti-CD138-IFNα2 fusion proteins to target CD138 expressed on multiple myeloma. See, Vasuthasawat, et. al., MAbs 8(7), pp. 1386-1397 (2016). While these approaches have shown great therapeutic promise and are currently being tested in human clinical trials and developed commercially, there are several deficiencies of these available approaches.

Although using the antibody binding specificity to target tumor-associated antigens delivers a greater percentage of the IFN to the site of the tumor than is achieved when IFN is injected by itself, the attached interferon still can be recognized and bound by interferon receptors expressed by cells throughout the body, such as cells that are not tumor associated or normal cells. This binding can result both in less IFN reaching the tumor and in unwanted off-target toxicity. Provided are embodiments that overcome such limitations and deficiencies.

Accordingly, it is an object of the present invention to overcome these limitations by providing a mechanism of "masking" the function or the activity of the IFN until at which time the IFN reaches the location or region that is relevant for the treatment of the disease or disorder, such as the tumor. At that time, the IFN is "unmasked" and the activity and function is effectively switched back on. As such, in some embodiments, provided are fusion proteins, e.g., a targeted masked IFN, that is "unmasked" or "activated" only at the location of interest for the therapeutic effect, such as the tumor. In some aspects, masking of the function or activity of the IFN in the rest of the body, e.g., the systemic circulation in general, can reduce or prevent non-specific activity of the IFN and also reduce or prevent the therapeutic agent, e.g., the IFN, from being trapped in or soaked up by non-cancerous or non-tumorous cells in the body. In some aspects, masking of the function or activity of the IFN and targeting the IFN to location of interest, e.g., to a tumor, by virtue of the antibodies present in the provided embodiments, can effectively increase the concentration of the therapeutic agent (e.g., the IFN), for example by preventing the IFN from being bound to and/or trapped in by specific targeting of the agent by the antibody.

Accordingly, in some embodiments, the invention comprises an antibody-IFN fusion protein in which the IFN will selectively bind IFN receptors once it reaches the tumor.

In another embodiment, the antibody-IFN fusion protein comprises an IFN that is separated by a peptide linker that is a site for proteolytic cleavage.

In another embodiment, the antibody-IFN fusion protein comprises a "masked" IFN.

In another embodiment, the antibody-IFN fusion protein comprises a "masked" IFN that is separated by a peptide linker that is a site for proteolytic cleavage.

In another embodiment, the antibody-IFN fusion protein comprises a "masked" IFNA1.

In another embodiment, the antibody-IFN fusion protein comprises a "masked" IFNA1 that is separated by a peptide linker that is a site for proteolytic cleavage.

In another embodiment, the antibody-IFN fusion protein comprises a "masked" IFNA2.

In another embodiment, the antibody-IFN fusion protein comprises a "masked" IFNA2 that is separated by a peptide linker that is a site for proteolytic cleavage.

In another embodiment, the antibody-IFN fusion protein comprises a "masked" IFNB1.

In another embodiment, the antibody-IFN fusion protein comprises a "masked" IFNB1 that is separated by a peptide linker that is a site for proteolytic cleavage.

In another embodiment, the antibody-IFN fusion protein comprises a "masked" IFN selected from the IFN set forth in Table II.

In another embodiment, the antibody-IFN fusion protein comprises a "masked" IFN that is separated by a peptide linker that is a site for proteolytic cleavage and is selected from the IFN set forth in Table II.

In another aspect, the antibody-IFN fusion protein comprises IFNα2 comprising the following:

```
                                              (SEQ ID NO: 7)
CDLPQTHSLGSRRTLMLLAQMRRISLFSCLKDRHDFGFPQEEFG

NQFQKAETIPVLHEMIQQIFNLFSTKDSSAAWDETLLDKFYTEL

YQQLNDLEACVIQGVGVTETPLMKEDSILAVRKYFQRITLYLKE

KKYSPCAWEVVRAEIMRSFSLSTNLQESLRSKE
```

IV.) Methods of Masking IFNs

As previously noted, it is an object of the present invention to provide for targeted masked IFN compositions whereby the activity of an IFN of the present invention (See, Table II) is inhibited until at which time it reaches a tumor and the mask is removed by proteases, such as tumor-associated proteases. In some aspects, the provided masked IFNs, such as targeted masked IFNs, are "unmasked" at or near the location of the disease or disorder to be treated, e.g., at or near a tumor, such as a tumor microenvironment, and become capable of binding to and/or activating the interferon receptor (e.g., IFNAR). In some aspects, the unmasking or activating of the provided fusion proteins, occurs by virtue of cleavage of a component, such as a peptide linker, by a protein in the environment of the tumor, such as a tumor associated protease.

(a) Discussion of Available Approaches.

Available approaches that are related this endeavor is limited. The disclosure presents an explanation of the available approaches to further demonstrate and show the technical advantages of the present invention. A prior approach to improving tumor specific delivery of therapeutics was to create a therapeutic which is activated by tumor associated proteases. An example of this approach has been to take antibodies that recognize tumor associated antigens but are limited in their efficacy because they also recognize antigens present on normal cells and modify them so that they only bind antigen when localized in the target tumor. See, U.S. Pat. No. 8,563,269 (CytomX Therapeutics, San Francisco, Calif.). The so-called "Probodies" have an associated peptide that blocks the antibody binding site joined by a linker that is cleavable by proteases present in the tumor microenvironment. In one case the antibody, CETUXIMAB, specific for epidermal growth factor receptor (EGFR) that was only activated to bind when localized to the tumors was produced. See, Desnoyers, et. al., Sci. Transl. Med., 16:5(207) pp. 207ra144 (2013). In this "Probody", a mask sequence that binds the variable region of CETUXIMAB followed by a GS-linker and then the sequence (SEQ ID NO: 8)
LSGRSDNHGSSGT was attached to the amino terminus of the heavy chain of the antibody. In that case, the underlined sequence is a substrate for UPA and matriptase, proteases known to be up regulated in a variety of human carcinomas with minimal activity in normal tissues. This probody demonstrated improved safety and increased half-life in nonhuman primates.

In addition to producing Probodies with antibody binding activated in the tumor microenvironment, it has been possible to produce a protease activated interferon alpha proprotein. See, U.S. Pat. No. 8,399,219 (CytomX Therapeutics, San Francisco, Calif.). In that case a peptide mask for IFN-α TDVDYYREWSWTQVS (SEQ ID NO: 9) was placed at the amino terminus of single chain recombinant IFNα separated from the IFNα by a cleavable sequence. The resulting construct: GQSGQ TDVDYYREWSETQVS GSSGGS VHMPLGFLGP GGS (SEQ ID NO: 10) IFNα contained IFNα that was selectively activated in the tumor microenvironment. It is taught that VHMPLGFLGP (SEQ ID NO: 11) is a substrate for MMP-9.

(b) Methods of Masking IFN of the Disclosure.

The provided fusion proteins, including masked IFNs and targeted masked IFNs, are capable of being unmasked at or near the location of the disease or disorder. From the aforementioned, the methods of masking IFNs of the present disclosure are clearly distinguishable and provide an advantage over any available approaches.

For example, as described above, the provided embodiments include a mechanism of "masking" the function or the activity of the IFN until at which time the IFN reaches the location or region that is relevant for the treatment of the disease or disorder, such as the tumor, and specific physical targeting of the fusion protein at the location of the tumor by virtue of the TAA-specific antibody that is fused to the IFN. Accordingly, the fusion proteins described herein provide multiple advantages, including, but not limited to, that the IFN is "unmasked" or "activated" only at the location of interest for the therapeutic effect, such as the tumor; non-specific activity of the IFN is reduced; that the IFN is prevented from being trapped in or soaked up by non-cancerous or non-tumorous cells in the body; and/or effectively increasing the concentration of the therapeutic agent (e.g., the IFN) without an increase in toxicity.

In some of any of the embodiments, the provided fusion protein, e.g., a targeted masked IFN, is only unmasked at or near the site of the disease or disorder, e.g., the tumor. Accordingly, in some embodiments, the invention comprises an antibody-IFN fusion protein in which the IFN will selectively bind IFN receptors once it reaches the location or region of the tumor.

In some embodiments, the antibody-IFN fusion protein comprises an IFN that is separated by a peptide linker that is a site for proteolytic cleavage. In some aspects, the proteolytic cleavage of the peptide linker can "unmask" or activate the IFN, for example, at or near a tumor.

As described in the disclosure, the provided embodiments include an antibody-IFN in which the IFN, such as those described in Section III or Table II herein, is fused to the antibody as described herein, for example in Section II or Table I. The IFN is then "masked" so that it will only become active and bind its receptors at the site of the tumor. In an uncleaved state the ideal peptide mask inhibits binding of the protein (e.g., the IFN) to its binding partner (e.g., interferon receptor, such as IFNAR), and following cleavage the peptide mask does not inhibit binding of the protein to its binding partners. In the embodiments provided herein, the cleavage of the "mask," for example, at or near the site of the tumor, allows the Type I IFN to bind to its receptor, e.g., IFNAR, and exert its therapeutic effect.

The following describes an exemplary embodiment:

First, IFNα2 was used and a protease cleavage site and a "mask" that inhibits IFN binding was placed on the 3' terminus fused to $C_H3$. It is contemplated by the disclosure that at the site of the tumor, proteases within the tumor microenvironment will cleave the protease cleavage site releasing the mask and freeing the IFN so that it can bind to its receptor.

The nucleic acids for the construction of a recombinant heavy chain with a protease cleavage site and IFN inhibitory mask were obtained (ATUM, Newark, Calif.) and used to modify the heavy chain (H chain) of anti-CD138-IFNα2 by producing the following fusion at its 3' end:

(SEQ ID NO: 12)
VVRAEIMRSFSLSTNLQESLRSKEgssgLSGRSDNHgssggsgg sggsgTDVDYYREWSWTQVSgg Single underline indicates the carboxy-terminus of IFNα2, double underline represents the sequence for the protease cleavage site, and dashed underline represents the IFNα2 mask. Linker sequences are shown as lower case.

In another embodiment, the construct comprises:

(SEQ ID NO: 13)
VVRAEIMRSFSLSTNLQESLRSKEgssgLSGRSDNHgssggsgg sggsgTDVDYYREWSWTQVgg In one embodiment, the "masked" IFN comprises: TDVDYYREWSWTQV (SEQ ID NO: 14).

In one embodiment, the "masked" IFN comprises: TDVDYYREWSWTQV (SEQ ID NO: 14) and further comprises IFNα1.

In one embodiment, the "masked" IFN comprises: TDVDYYREWSWTQV (SEQ ID NO: 14) and further comprises IFNα2.

In one embodiment, the "masked" IFN comprises: TDVDYYREWSWTQV (SEQ ID NO: 14) and further comprises IFNα4.

In one embodiment, the "masked" IFN comprises: TDVDYYREWSWTQV (SEQ ID NO: 14) and further comprises IFNα5.

In one embodiment, the "masked" IFN comprises: TDVDYYREWSWTQV (SEQ ID NO: 14) and further comprises IFNα1 fused to an antibody which binds CD138.

In one embodiment, the "masked" IFN comprises: TDVDYYREWSWTQV (SEQ ID NO: 14) and further comprises IFNα1 fused to an antibody which binds CD20.

In one embodiment, the "masked" IFN comprises: TDVDYYREWSWTQV (SEQ ID NO: 14) and further comprises IFNα1 fused to an antibody which binds Her2.

In one embodiment, the "masked" IFN comprises: TDVDYYREWSWTQV (SEQ ID NO: 14) and further comprises IFNα1 fused to an antibody which binds CSPG4.

In one embodiment, the "masked" IFN comprises: TDVDYYREWSWTQV (SEQ ID NO: 14) and further comprises IFNα1 fused to an antibody which binds PSCA.

In one embodiment, the "masked" IFN comprises: TDVDYYREWSWTQV (SEQ ID NO: 14) and further comprises IFNα1 fused to an antibody which binds CEA.

In one embodiment, the "masked" IFN comprises: TDVDYYREWSWTQV (SEQ ID NO: 14) and further comprises IFNα1 fused to an antibody which binds RCC.

In one embodiment, the "masked" IFN comprises: TDVDYYREWSWTQV (SEQ ID NO: 14) and further comprises IFNα1 fused to an antibody which binds 5T4.

In one embodiment, the "masked" IFN comprises: TDVDYYREWSWTQV (SEQ ID NO: 14) and further comprises IFNα1 fused to an antibody which binds mesothelin.

In one embodiment, the "masked" IFN comprises: TDVDYYREWSWTQV (SEQ ID NO: 14) and further comprises IFNα2 fused to an antibody which binds CD138.

In one embodiment, the "masked" IFN comprises: TDVDYYREWSWTQV (SEQ ID NO: 14) and further comprises IFNα2 fused to an antibody which binds CD20.

In one embodiment, the "masked" IFN comprises: TDVDYYREWSWTQV (SEQ ID NO: 14) and further comprises IFNα2 fused to an antibody which binds Her2.

In one embodiment, the "masked" IFN comprises: TDVDYYREWSWTQV (SEQ ID NO: 14) and further comprises IFNα2 fused to an antibody which binds CSPG4.

In one embodiment, the "masked" IFN comprises: TDVDYYREWSWTQV (SEQ ID NO: 14) and further comprises IFNα2 fused to an antibody which binds PSCA.

In one embodiment, the "masked" IFN comprises: TDVDYYREWSWTQV (SEQ ID NO: 14) and further comprises IFNα2 fused to an antibody which binds CEA.

In one embodiment, the "masked" IFN comprises: TDVDYYREWSWTQV (SEQ ID NO: 14) and further comprises IFNα2 fused to an antibody which binds RCC.

In one embodiment, the "masked" IFN comprises: TDVDYYREWSWTQV (SEQ ID NO: 14) and further comprises IFNα2 fused to an antibody which binds 5T4.

In one embodiment, the "masked" IFN comprises: TDVDYYREWSWTQV (SEQ ID NO: 14) and further comprises IFNα2 fused to an antibody which binds mesothelin.

In one embodiment, the "masked" IFN comprises: TDVDYYREWSWTQVS (SEQ ID NO: 15).

In one embodiment, the "masked" IFN comprises: TDVDYYREWSWTQVS (SEQ ID NO: 15) and further comprises IFNα1.

In one embodiment, the "masked" IFN comprises: TDVDYYREWSWTQVS (SEQ ID NO: 15) and further comprises IFNα2.

In one embodiment, the "masked" IFN comprises: TDVDYYREWSWTQVS (SEQ ID NO: 15) and further comprises IFNα4.

In one embodiment, the "masked" IFN comprises: TDVDYYREWSWTQVS (SEQ ID NO: 15) and further comprises IFNα5.

In one embodiment, the "masked" IFN comprises: TDVDYYREWSWTQVS (SEQ ID NO: 15) and further comprises IFNα1 fused to an antibody which binds CD138.

In one embodiment, the "masked" IFN comprises: TDVDYYREWSWTQVS (SEQ ID NO: 15) and further comprises IFNα1 fused to an antibody which binds CD20.

In one embodiment, the "masked" IFN comprises: TDVDYYREWSWTQVS (SEQ ID NO: 15) and further comprises IFNα1 fused to an antibody which binds Her2.

In one embodiment, the "masked" IFN comprises: TDVDYYREWSWTQVS (SEQ ID NO: 15) and further comprises IFNα1 fused to an antibody which binds CSPG4.

In one embodiment, the "masked" IFN comprises: TDVDYYREWSWTQVS (SEQ ID NO: 15) and further comprises IFNα1 fused to an antibody which binds PSCA.

In one embodiment, the "masked" IFN comprises: TDVDYYREWSWTQVS (SEQ ID NO: 15) and further comprises IFNα1 fused to an antibody which binds CEA.

In one embodiment, the "masked" IFN comprises: TDVDYYREWSWTQVS (SEQ ID NO: 15) and further comprises IFNα1 fused to an antibody which binds RCC.

In one embodiment, the "masked" IFN comprises: TDVDYYREWSWTQVS (SEQ ID NO: 15) and further comprises IFNα1 fused to an antibody which binds 5T4.

In one embodiment, the "masked" IFN comprises: TDVDYYREWSWTQVS (SEQ ID NO: 15) and further comprises IFNα1 fused to an antibody which binds mesothelin.

In one embodiment, the "masked" IFN comprises: TDVDYYREWSWTQVS (SEQ ID NO: 15) and further comprises IFNα2 fused to an antibody which binds CD138.

In one embodiment, the "masked" IFN comprises: TDVDYYREWSWTQVS (SEQ ID NO: 15) and further comprises IFNα2 fused to an antibody which binds CD20.

In one embodiment, the "masked" IFN comprises: TDVDYYREWSWTQVS (SEQ ID NO: 15) and further comprises IFNα2 fused to an antibody which binds Her2.

In one embodiment, the "masked" IFN comprises: TDVDYYREWSWTQVS (SEQ ID NO: 15) and further comprises IFNα2 fused to an antibody which binds CSPG4.

In one embodiment, the "masked" IFN comprises: TDVDYYREWSWTQVS (SEQ ID NO: 15) and further comprises IFNα2 fused to an antibody which binds PSCA.

In one embodiment, the "masked" IFN comprises: TDVDYYREWSWTQVS (SEQ ID NO: 15) and further comprises IFNα2 fused to an antibody which binds CEA.

In one embodiment, the "masked" IFN comprises: TDVDYYREWSWTQVS (SEQ ID NO: 15) and further comprises IFNα2 fused to an antibody which binds RCC.

In one embodiment, the "masked" IFN comprises: TDVDYYREWSWTQVS (SEQ ID NO: 15) and further comprises IFNα2 fused to an antibody which binds 5T4.

In one embodiment, the "masked" IFN comprises: TDVDYYREWSWTQVS (SEQ ID NO: 15) and further comprises IFNα2 fused to an antibody which binds mesothelin.

In one embodiment, the "masked" IFN comprises a neutralizing scFv which also acts as a mask (as defined within the context of the disclosure) to provide a synergistic ability to mask the IFNAR.

The resulting embodiments, such as the targeted masked IFN provides a unique advantage over the prior art for several reasons. First, the IFN is masked so that its activity is significantly reduced and/or eliminated until it reaches the tumor. At which time, the mask is removed, and the activity is re-activated which maximizes the efficacy in the tumor. Second, by attaching the C-terminal linked masked IFN to the C-terminal of the antibody the masked IFN can be targeted to a specific TAA. The specific targeting allows for greater opportunity that the IFN will be directed to the cancer of interest and avoid normal tissue.

The disclosure contemplates general embodiments of the resulting Targeted Masked IFN, including but not limited to the following:

First, a composition as shown herein:

(i) Antibody-linker-cytokine (e.g. IFN)-linker-Protease cleavage (PC) site-linker-mask; and Second, a composition as shown herein:

(ii) Antibody-linker-PC cleavage site-linker-cytokine (e.g. IFN)

It will be appreciated that one of skill in the art will appreciate and understand that the composition set forth in (ii) has an additional property of the antibody acting as a partial mask through steric hindrance of the cytokine presented in the composition.

In some embodiments, the protease cleavage site is a tumor-associated protease cleavage site. A "tumor-associated protease cleavage site" as provided herein is an amino acid sequence recognized by a protease, whose expression is specific for a tumor cell or tumor cell environment thereof. In some embodiments, exemplary protease cleavage site include a tumor-associated protease cleave site, such as a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site, a matriptase protease cleavage site (ST14) or a legumain protease cleavage site. In some aspects protease cleavage sites may be designated by a specific amino acid sequence.

V.) Treatment of Cancer(s) Expressing a Tumor Associates Antigen (TAA)

Also provided herein are fusion proteins, such as targeted masked IFNs, or compositions, that are useful in a variety of therapeutic, diagnostic and prophylactic methods and uses. For example, the fusion proteins and compositions are useful in treating a variety of diseases and disorders in a subject, such as a cancer or a tumor. Such methods and uses include therapeutic methods and use, for example, involving administration of the fusion protein or compositions, to a subject having a disease or disorder, such as a tumor or a cancer. In some embodiments, the fusion protein or compositions are administered in an effective amount to effect treatment of the disease or disorder. Uses include uses of the fusion proteins or compositions in such methods and treatments, and in the preparation of a medicament in order to carry out such therapeutic methods. In some embodiments, the fusion proteins or compositions are for use in treating a variety of diseases and disorders in a subject, for example, in accordance with the therapeutic methods. In some embodiments, the methods are carried out by administering the fusion proteins or compositions, to the subject having or suspected of having the disease or disorder, such as a tumor or a cancer. In some embodiments, the methods thereby treat the disease or disorder in the subject.

In some aspects, the provided fusion proteins, e.g., targeted masked IFNs, are employed in methods or uses for treatment of a disease or disorder such as a tumor or a cancer, including those expressing a tumor-associated antigen (TAA). The identification of a TAA of the disclosure as a protein that is normally expressed in a restricted set of tissues or cells, but which is also expressed in cancers, for example, solid tumor cancer, opens a number of therapeutic approaches to the treatment of such cancers utilizing masked fusion proteins disclosed herein.

Of note, targeted antitumor therapies have been useful even when the targeted protein is expressed on normal tissues or cells, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensable, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a TAA protein, comprising a targeted masked IFN fusion proteins of the invention are useful for patients suffering from a cancer that expresses a TAA (such as, for example, solid tumor cancers in the lung, kidney, prostate, ovary, breast and other types of cancer known in the art). The therapeutic approach involves IFNA induced killing (e.g. when the "mask" is removed and the IFN is reactivated in the tumor of interest), ADCC, CDC, and/or immune modulation. In addition, the antibody which binds the TAA may also synergistically modulate the function of a cancer cell. In addition, further, the "unmasked" or activated IFN can modulate activity of immune cells involved in anti-tumor or anti-cancer immunity, by virtue of binding of the IFN to the interferon receptor (e.g., IFNAR). The modulation of the antibody which binds the TAA generally fall into two classes. The first class modulates TAA function as it relates to tumor cell growth leading to inhibition or retardation of tumor cell growth or inducing its killing. The second class comprises various methods for inhibiting the binding or association of a TAA protein with its binding partner or with other proteins.

Accordingly, Cancer patients can be evaluated for the presence and level of TAA expression, preferably using immunohistochemical assessments of tumor tissue, quantitative TAA imaging, or other techniques that reliably indicate the presence and degree of TAA expression. Immunohistochemical analysis of tumor biopsies or surgical specimens is preferred for this purpose, if applicable. Methods for immunohistochemical analysis of tumor tissues are well known in the art.

VI.) Targeted Masked IFN Fusion Protein Cocktails

Therapeutic methods of the invention contemplate the administration of single targeted masked IFN fusion protein as well as combinations, or cocktails, of different MAbs (i.e. naked MAbs that bind the same TAA as the masked IFN fusion protein or MAbs that bind another protein or another targeted masked IFN fusion protein which binds another TAA altogether). Such MAb cocktails can have certain advantages inasmuch as they contain MAbs that target different epitopes, exploit different effector mechanisms or combine directly cytotoxic MAbs with MAbs that rely on immune effector functionality. Such MAbs in combination can exhibit synergistic therapeutic effects. In addition, targeted masked IFN fusion proteins can be administered concomitantly with other therapeutic modalities, including but not limited to various chemotherapeutic and biologic agents, androgen-blockers, immune modulators (e.g., IL-2, GM-CSF), surgery or radiation. In a preferred embodiment, the targeted masked IFNs are administered in fusion protein form.

Targeted masked IFN fusion protein formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the targeted masked IFN fusion protein preparation, via an acceptable route of administration such as intravenous injection (IV), typically at a dose in the range, including but not limited to, 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg targeted masked IFN fusion protein per week are effective and well tolerated.

Based on clinical experience with the Herceptin® (Trastuzumab) in the treatment of metastatic breast cancer, an initial loading dose of approximately 4 mg/kg patient body weight IV, followed by weekly doses of about 2 mg/kg IV of the MAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half-life of the TAA MAbs used, the degree of TAA expression in the patient, the extent of circulating shed TAA antigen, the desired steady-state antibody concentration level, frequency of treatment, and the influence of chemotherapeutic or other agents used in combination with the treatment method of the invention (i.e. targeted masked IFN), as well as the health status of a particular patient.

Optionally, patients should be evaluated for the levels of TAA in a given sample (e.g. the levels of circulating TAA and/or TAA expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

An object of the present invention is to provide targeted masked IFN fusion proteins, which inhibit or retard the growth of tumor cells expressing a specific TAA to which the fusion protein binds. A further object of this invention is to provide methods to inhibit angiogenesis and other biological functions and thereby reduce tumor growth in mammals, preferably humans, using such targeted masked IFN comprising fusion proteins which bind TAAs, and in particular using such targeted masked IFN comprising fusion proteins which find a specific TAA combined with other drugs or immunologically active treatments.

VII.) Combination Therapy

In some embodiments, also provided are methods and uses that involve a combination therapy, for example, that involve the use of any of the provided fusion proteins or compositions, and an additional therapeutic agent, such as a chemotherapeutic agent or radiation. In some embodiments, the provided fusion proteins or compositions can be used in combination with an additional therapeutic agent for treatment of the disease or disorder, such as an anti-cancer or anti-tumor agent.

In some embodiments, there is synergy when tumors, including human tumors, are treated with targeted masked IFN fusion proteins which bind a specific TAA in conjunction with an additional therapeutic agent, such as, chemotherapeutic agents, radiation, an immunomodulating therapy, or any combinations thereof. In other words, the inhibition of tumor growth by a targeted masked IFN fusion protein which binds a specific TAA is enhanced more than expected when combined with chemotherapeutic agents or radiation or combinations thereof. Synergy may be shown, for example, by greater inhibition of tumor growth with combined treatment than would be expected from a treatment of only targeted masked IFN fusion proteins which bind a specific TAA or the additive effect of treatment with a targeted masked IFN fusion proteins which bind a specific TAA and a chemotherapeutic agent or radiation. Preferably, synergy is demonstrated by remission of the cancer where remission is not expected from treatment either from a targeted masked IFN fusion proteins which bind a specific TAA or with treatment using an additive combination of a targeted masked IFN fusion proteins which bind a specific TAA and a chemotherapeutic agent or radiation.

The method for inhibiting growth of tumor cells using a targeted masked IFN fusion proteins which bind a specific TAA and a combination of chemotherapy, radiation, or immunomodulating therapies, or a combination of any one, two, or three comprises administering the targeted masked IFN fusion proteins which bind a specific TAA before, during, or after commencing chemotherapy or radiation therapy, as well as any combination thereof (i.e. before and during, before and after, during and after, or before, during, and after commencing the chemotherapy and/or radiation therapy). For example, the targeted masked IFN fusion proteins which bind a specific TAA is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the targeted masked IFN fusion proteins which bind a specific TAA and the chemotherapeutic agent are administered as separate molecules. Particular examples of chemotherapeutic agents or chemotherapy include bortezomib, carfilzomib, lenalidomide, pomalidomide, cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with a targeted masked IFN fusion proteins which bind a specific TAA, can be either external or internal to the patient being treated. When the source is external to the patient, the therapy is known as external beam radiation therapy (EBRT). When the source of radiation is internal to the patient, the treatment is called brachytherapy (BT).

The above described therapeutic regimens may be further combined with additional cancer treating agents and/or regimes, for example, bortezomib, pomalidomide, and/or additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

Examples of immunomodulating therapies used in cancer treatment, include but are not limited to, anti-(CTLA-4, PD-1, PD-L1, TIGIT, LAG3, T1B7-H3, B7-H4) and others known in the art.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

VIII.) Kits/Articles of Manufacture

For use in the laboratory, prognostic, prophylactic, diagnostic and therapeutic applications described herein, kits, article of manufacture, systems, and apparatuses are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a targeted masked IFN fusion protein which bind a specific TAA or several TAAs of the disclosure. Kits can comprise a container comprising a targeted masked IFN. The kit can include all or part of the targeted masked IFN fusion protein which binds a specific TAA and/or diagnostic assays for detecting cancer and/or other immunological disorders.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as targeted masked IFN fusion protein which binds a specific TAA of the disclosure. The article of manufacture typically comprises at least one container and at least one label. Suitable containers include, for example, bottles, vials, syringes, and test tubes. The containers can be formed from a variety of materials such as glass, metal or plastic. The container can hold one or several targeted masked IFN fusion protein which bind a specific TAAs and/or one or more therapeutics doses of targeted masked IFNs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a targeted masked IFN fusion protein which bind a specific TAA of the present disclosure.

The article of manufacture can further comprise a second container comprising a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXEMPLARY EMBODIMENTS

Among the provided embodiments are:
1) A composition, comprising the polypeptide sequence TDVDYYREWSWTQV (SEQ ID NO: 14), wherein said polypeptide sequence masks the activity of a Type-I interferon (IFN) and wherein said composition further comprises a fusion protein which is fused to an antibody that binds to a tumor associated antigen.
2) The composition of embodiment 1, further comprising a flexible peptide linker.
3) The composition of embodiment 1 or 2, further comprising a tumor associated protease cleavage site.
4) The composition of any one of embodiments 1-3, wherein the Type-I interferon comprises IFNα1.
5) The composition of any one of embodiments 1-3, wherein the Type-I interferon comprises IFNα2.
6) The composition of any one of embodiments 1-3, wherein the Type-I interferon comprises IFNα4.
7) The composition of any one of embodiments 1-3, wherein the Type-I interferon comprises IFNα5.
8) The composition of any one of embodiments 1-3, wherein the Type-I interferon comprises IFNα6.

9) The composition of any one of embodiments 1-3, wherein the Type-I interferon comprises IFNα14.
10) The composition of any one of embodiments 1-3, wherein the Type-I interferon comprises IFNβ1.
11) The composition of any one of embodiments 1-3, wherein the Type-I interferon or functional mutant thereof is selected from a Type-I interferon as shown in Table II.
12) The composition of any one of embodiments 1-11, wherein the Tumor Associated Antigen comprises CD138.
13) The composition of any one of embodiments 1-11, wherein the Tumor Associated Antigen comprises CD20.
14) The composition of any one of embodiments 1-11, wherein the Tumor Associated Antigen comprises mesothelin.
15) The composition of any one of embodiments 1-11, wherein the Tumor Associated Antigen comprises 5T4.
16) The composition of any one of embodiments 1-11, wherein the Tumor Associated Antigen is selected from a tumor associated antigen as shown in Table I.
17) A Targeted Masked IFN comprising:
    a. an antibody comprising a heavy chain and/or a light chain which specifically binds to a tumor associated antigen;
    b. a Type-I interferon, wherein the N-terminal of said Type-I interferon is fused to the C-terminal of said antibody heavy and/or light chains; and
    c. an interferon mask which comprises (SEQ ID NO: 14) whereby said interferon mask is attached at the C-terminal of said Type-I interferon.
18) The Targeted Masked IFN of embodiment 17, wherein the N-terminal of said Type-I interferon is fused to the C-terminal of said antibody heavy and/or light chain further comprising a flexible peptide linker.
19) The Targeted Masked IFN of embodiment 17 or 18, wherein the interferon mask (SEQ ID NO: 14) is attached to the C-terminal of said Type-I interferon further comprising a flexible peptide linker.
20) The Targeted Masked IFN of embodiment 19, further comprising a tumor associated protease cleavage site inserted between said antibody and said flexible peptide linker.
21) The Targeted Masked IFN of any of embodiments 17-19, further comprising a tumor associated protease cleavage site inserted between said Type-I interferon and said interferon mask.
22) The Targeted Masked IFN of any one of embodiments 17-21, wherein said Type-I IFN or functional mutant thereof is set forth in Table II.
23) The Targeted Masked IFN of any one of embodiments 17-22, wherein said antibody binds a tumor associated antigen set forth in Table I.
24) The Targeted Masked IFN of any one of embodiments 17-22, wherein said antibody binds CD138.
25) The Targeted Masked IFN of any one of embodiments 17-22, wherein said antibody binds CD20.
26) The Targeted Masked IFN of any one of embodiments 17-22, wherein said antibody binds mesothelin.
27) The Targeted Masked IFN of any one of embodiments 17-22, wherein said antibody binds 5T4.
28) A method of making the composition of any one of embodiments 1-16 or the Targeted Masked IFN of any one of embodiments 17-27.
29) A pharmaceutical composition comprising the composition of any one of embodiments 1-16 or the Targeted Masked IFN of any one of embodiments 17-27, (i) wherein, optionally, the pharmaceutical composition is for use in therapy including treatment of cancer, wherein, optionally, (a) the cancer comprises a cancer found in a solid tumor; or (b) the cancer arises in the hematopoietic system, and (ii) wherein, optionally, the pharmaceutical composition further comprises one or more anti-neoplastic agents;
30) A kit comprising the composition of any one of embodiments 1-16 or the Targeted Masked IFN of any one of embodiments 17-27.
31) A method of treating cancer in a subject, comprising administering to said subject a therapeutically effective amount of the composition of any one of embodiments 1-16 or the Targeted Masked IFN of any one of embodiments 17-27, wherein, optionally, the subject is a human subject.

EXAMPLES

Various aspects of the invention are further described and illustrated by way of the several examples that follow, none of which is intended to limit the scope of the invention.

EXAMPLE 1: CHARACTERIZATION OF TARGETED MASKED IFNα2 FUSED TO ANTI-CD138 (ANTI-CD138-IFNα2)

In this example, it is shown that the IFN mask can be cleaved from the H chain using Matripase ST 14. Briefly, an anti-CD138-IFNα2 and anti-CD138-IFNα2-mask were generated using the procedures set forth, supra. See, *Methods of Masking IFNs of the Disclosure*. The modified heavy chain was then transiently expressed in 293T cells with the appropriate L chain yielding anti-CD138-IFNα2-mask. Confirmation by SDS-PAGE analysis showed that the fusion protein was correctly assembled in $H_2L_2$ molecules with H and L chains of appropriate size. FACS analysis then showed the modified fusion protein bound to CD138 expressing cells.

The resulting analysis via Western Blot showed that Matriptase ST 14 can cleave the IFN mask from the H chain. Anti-CD138-IFNα2 without a mask was used as a control. (See, FIG. 1).

Example 2: Characterization of Targeted Masked IFNα2 Fused to Anti-CD138 Aglycosylated (N297Q) (Anti-CD138-IFNα2 N297Q)

In this example, it is shown that the IFN mask can be cleaved from the H chain using Matripase ST 14. Briefly, for samples treated with MST14 (R&D Systems), 50 ug of Ab was incubated with 0.5 ug MST14 for 1 hr. At 37 deg. C. Then, one (1) ug of each purified Ab was denatured by heating to 95 deg. C., reduced with ~2% beta-mercaptoethanol (Thermofisher), and run on 4-12% Bis-Tris SDS-PAGE gels (Invitrogen). Four (4) ug of each non-reduced Ab was denatured by heating to 95 deg. C and run on 5% PO4 SDS-PAGE gels. The resulting analysis shows that Matripase ST 14 efficiently cleaves the IFN mask on the aglycosylated Fusion Ab. Anti-CD138-IFNα2 without a mask was used as a control. (See, FIG. 2).

Example 3: Characterization of Targeted Masked IFNα2 Fused to Anti-5T4 & Anti-Mesothelin Fusion Abs In this example, it is shown that the IFN mask can be cleaved from the H chain using Matripase ST 14 on Fusion Abs to a plurality of targets. Briefly, for samples treated with MST14 (R&D Systems), 50 ug of Ab was incubated with 0.5 ug MST14 for 1 hr. At 37 deg. C. Then, one (1) ug of each purified Ab was denatured by heating to 95 deg. C., reduced with ~2% beta-mercaptoethanol (Thermofisher), and run on 4-12% Bis-Tris SDS-PAGE gels (Invitrogen). Four (4) ug of each non-reduced Ab was denatured by heating to 95 deg. C and run on 5% PO4 SDS-PAGE gels. The resulting analysis shows that Matripase ST 14 efficiently cleaves the IFN mask on 5T4 and mesothelin Fusion Abs. Anti-CD138-IFNα2 without a mask was used as a control. (See, FIG. 3).

Example 4: Binding of Masked Fusion Abs to IFNα2 Receptor

Figure 5:
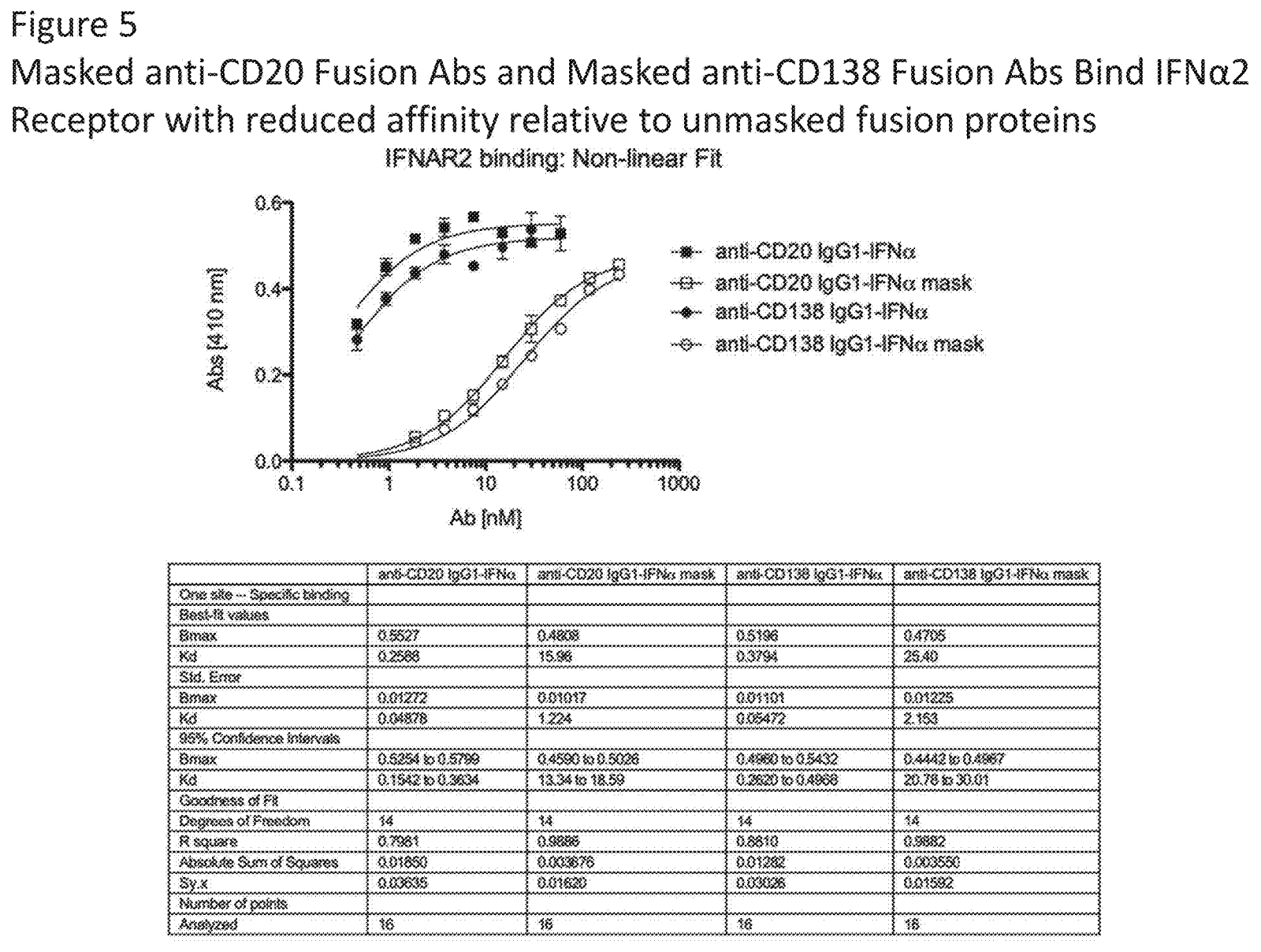

In this example, it is shown that a plurality of Masked Fusion Abs of the disclosure can bind to the IFNα2 receptor. Briefly, Immulon 2 HB plates (Thermofisher) were coated with 10 ug/mL IFNαR2 (R&D Systems) overnight at 4 deg. C and blocked with 2% BSA (Fisher) for a minimum of 2 hrs. at room temperature. Then, wells were washed 3× with PBS+0.05% Tween (Sigma). Indicated Ab concentrations were overlayed overnight at 4 deg. C. Wells were then washed 3× with PBS+0.05% Tween. Bound Abs were detected with anti-human Kappa-AP (Southern Biotech) diluted 1:3000 in PBS+1% BSA. Absorbance changes after addition of AP substrate (Sigma) were assayed at 410 nm using a Biotek EPOCH ELISA reader. The results show the masked 5T4, mesothelin, CD20, and CD138 Abs bind IFNαR2 with lower affinity compared to the unmasked 5T4, mesothelin, CD20, and CD138 Fusion Abs. (See, FIG. 4 and FIG. 5).

Example 5: Methods of Reducing and Restoring Masked IFNα Activity

Figure 6:
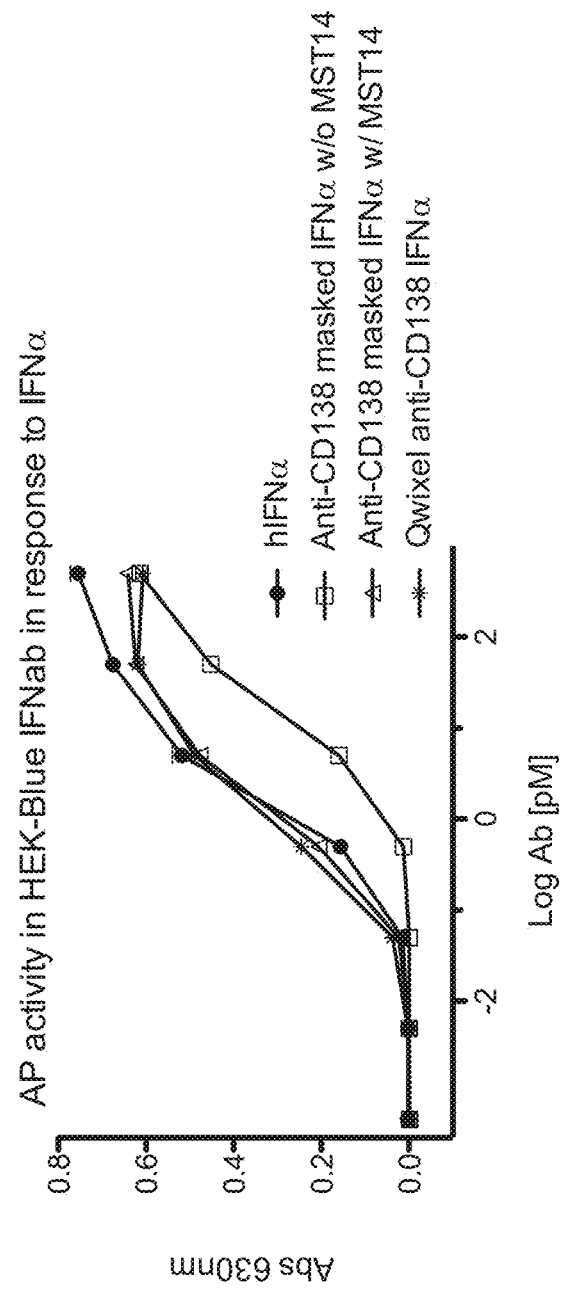
FIG. 6. Masking Reduces IFNα Fusion Protein Activation of IFN Receptor, while MST14 Restores Activity.

In this example, it is shown that the masked IFN fusion protein (anti-CD138-IFNα2) does not activate the type I IFN signaling pathway. The activation could then be restored following Matriptase ST 14 treatment. Briefly, using HEK-Blue™ IFN-α/β cells (Invitrogen, San Diego, Calif.) activation of the type I IFN signaling pathway is detected using a reporter gene expressing secreted embryonic alkaline phosphatase (SEAP) with gene activation monitored by quantitating alkaline phosphatase activity in the supernatant of treated cell. HEK-Blue™ IFN-α/β cells were incubated with hIFNα2, anti-CD138 masked IFNα2 w/o MST14, anti-CD138 masked IFNα2 w MST14; and an anti-CD138-IFNα2 for twenty-four (24) hours. The results show IFNα activity in masked anti-CD138-IFNα2 was found to be reduced to less than 10% of that seen in the unmasked protein; IFNα2 activity was restored to nearly 100% following matriptase/ST14 treatment (See, FIG. 6).

Example 6: Methods of Reducing and Restoring Masked IFNα Activity

Figure 7:
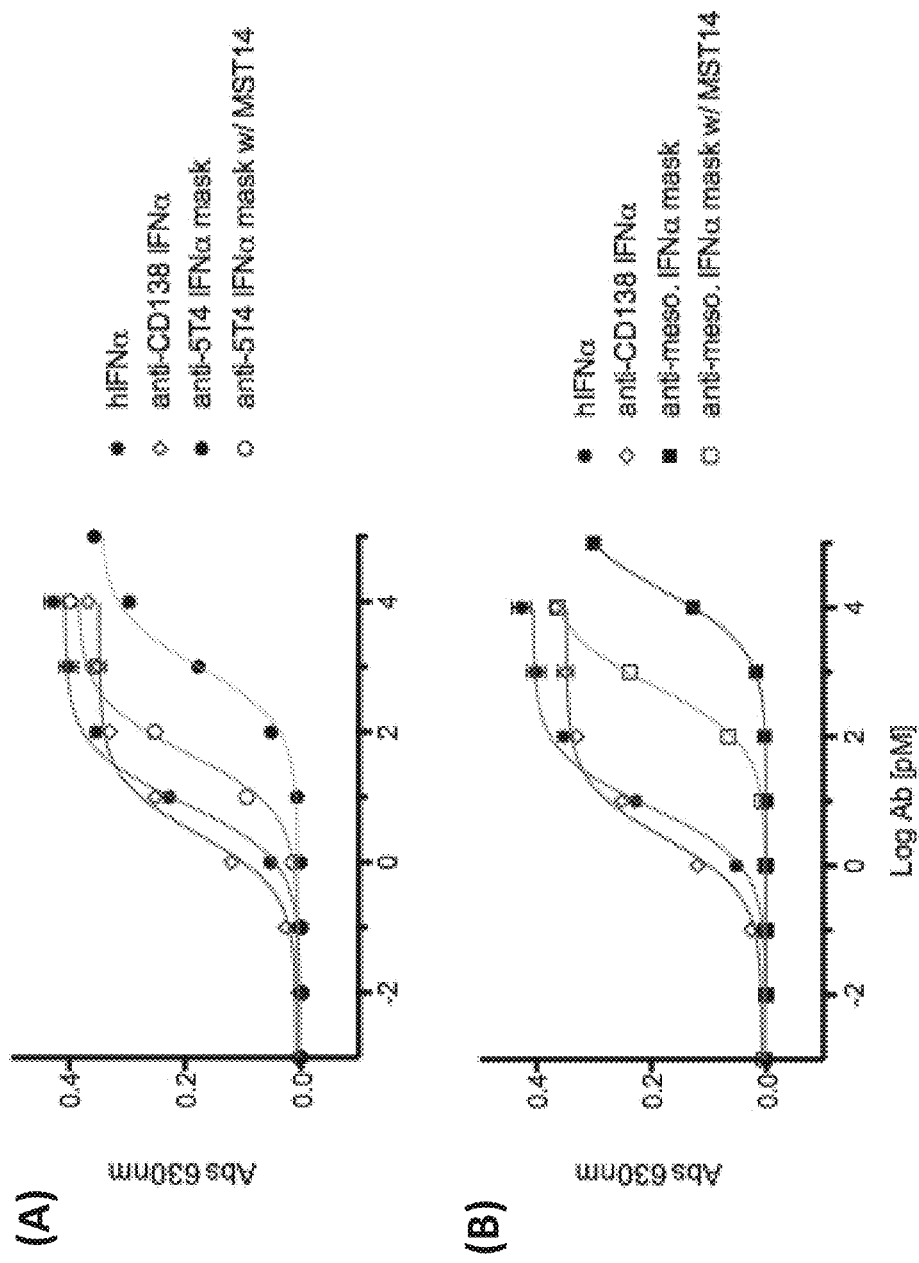
FIG. 7(A-B). Methods of Reducing and Restoring masked IFNα Activity.

In this example, it is shown that a plurality of Masked Fusion Abs of the disclosure can reduce and restore IFNα activity. Briefly, HEK Blue IFNa/b cells (Invivogen) were seeded into 96-well tissue culture plates (Fisher) at a density of 1×10e4 cells/well (50 uL/well). 50 uL/well of recombinant IFNα (Novus Biologicals) or indicated Abs (5T4 or Mesothelin) were incubated with the cells at the indicated concentrations overnight at 37 deg. C. Abs cleaved with MST14 (R&D Systems) were prepared by incubating 50 ug of Ab with 0.5 ug of MST14 for 1 hr. At 37 deg. C. Then, 10 uL of supernatant was added to a plate containing 90 uL/well Quanti-Blue substrate (Invivogen). Absorbance changes were read at 630 nm using a Biotek EPOCH ELISA reader. The results show that the IFNα activity in masked anti-5T4-IFNα and masked anti-mesothelin-IFNα was reduced by approximately 1 to 2 logs compared to when the mask is cleaved. (See, FIG. 7(A) & FIG. 7(B)).

Example 7: Methods of Reducing IP-10 Induction in PBMCs

Figure 8:
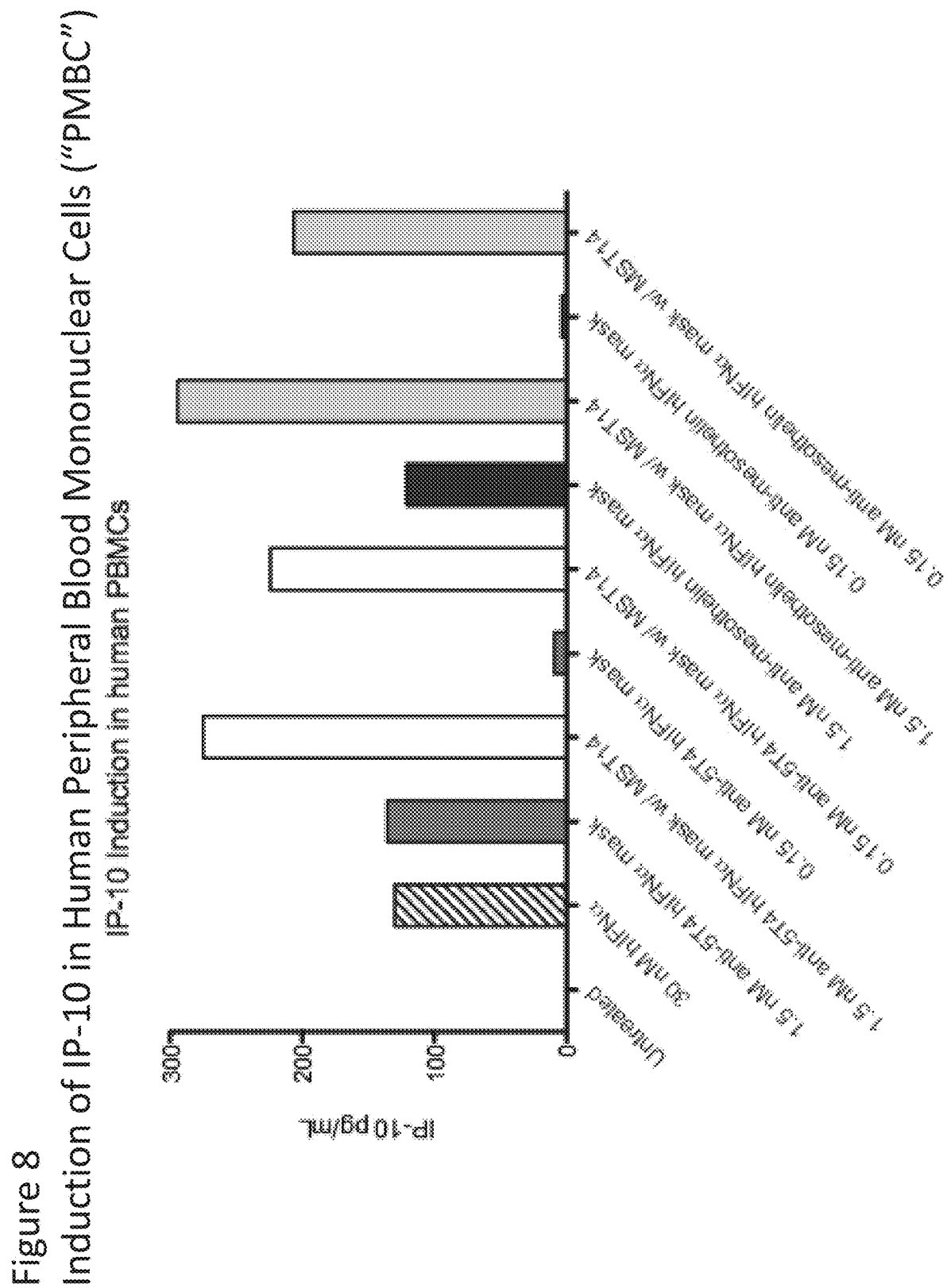
FIG. 8. Induction of IP-10 in Human Peripheral Blood Mononuclear Cells ("PMBC").

In this example, it is shown that a plurality of Masked Fusion Abs of the disclosure can reduce IP-10 induction. Briefly, freshly thawed human PBMCs (Human Cells Biosciences) were washed once with cold RPMI+10% FBS (Invitrogen) and seeded into a 12-well plate (Themofisher) at a density of ~1×10e6 cells/well (1 mL/well). Any Fc receptor and/or CD138 antigen expression was blocked/reduced with addition of 300 nM unfused anti-CD138 IgG1 to the cells for one (1) hr. before proceeding with the described experiment. Then, recombinant human IFNα (Novus Biologicals) or indicated Abs (5T4 or mesothelin) were added to the cells and allowed to incubate at 37 deg. C for an additional seven (7) hrs. Abs cleaved with MST14 (R&D Systems) were prepared by incubating 50 ug of Ab with 0.5 ug of MST14 for 1 hr. At 37 deg. C. After the seven (7) hr. incubation, cells were spun down for 3 min. at 500×g and 20 uL of supernatant from each sample and was assayed for IP-10 (Abcam) by ELISA according the manufacturer's protocol. The results show that the mask reduces IP-10 induction in both anti-5T4 and anti-mesothelin fusion Abs (See, FIG. 8).

Example 8: Methods of Making Mask Fusion Proteins

In this example, the construct design and characterization of QXL138AM is shown. Briefly, an anti-CD138 IgG1 is made using standard methods in the art. The heavy chain isotype is a human gamma 1 and the light chain isotype is human kappa. The mask was generated as described in the instant specification, See, *Methods of Masking IFNs of the Disclosure*. The resulting construct denoted QXL138AM (Anti-CD138-IFNα2-cleavable linker-mask) comprises the IgG heavy chain (set forth in Yellow) (SEQ ID NO: 6), a fusion protein linker (SGGGGS) (SEQ ID NO: 3), IFNα2 (set forth in green) (SEQ ID NO: 7), a cleavable linker, GSSGLSGRSDNHGSSGGSGGSGGSG (set forth in blue) (SEQ ID NO: 16), and a mask of the disclosure (set forth in purple) (SEQ ID NO: 15) (See, FIG. 9; full sequence set forth in SEQ ID NO:17, full sequence without signal peptide set forth in SEQ ID NO:18).

Figure 10:
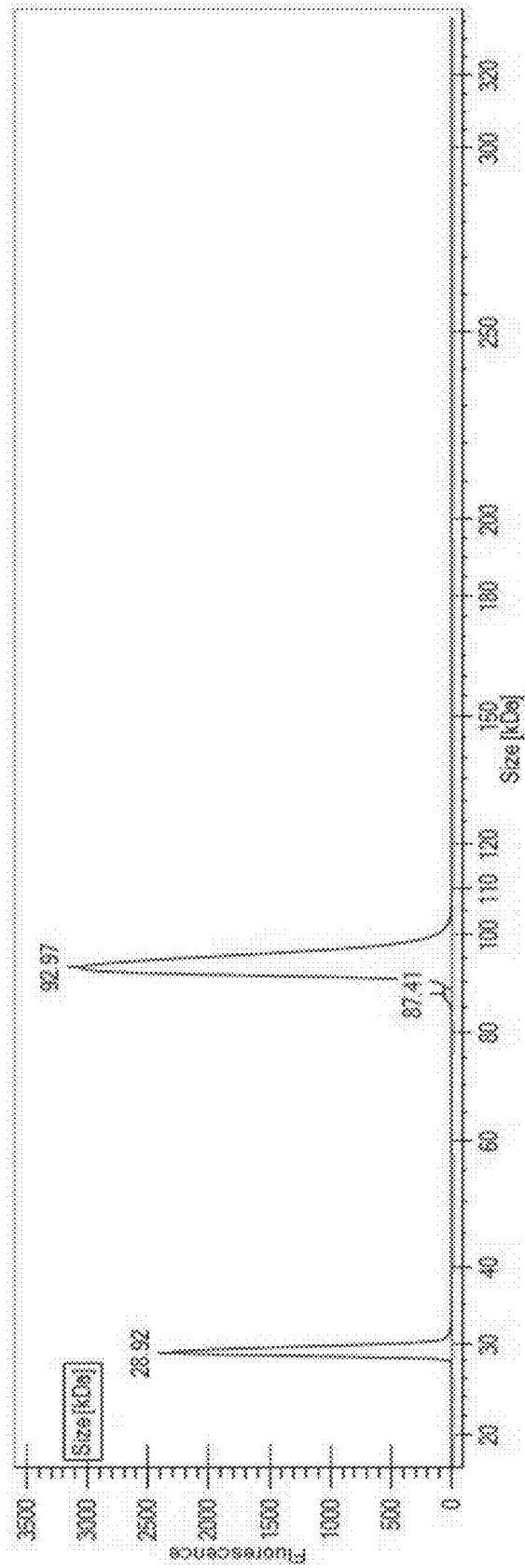
FIG. 10. QXL138AM Expression/Purification Characterization.
Figure 11:
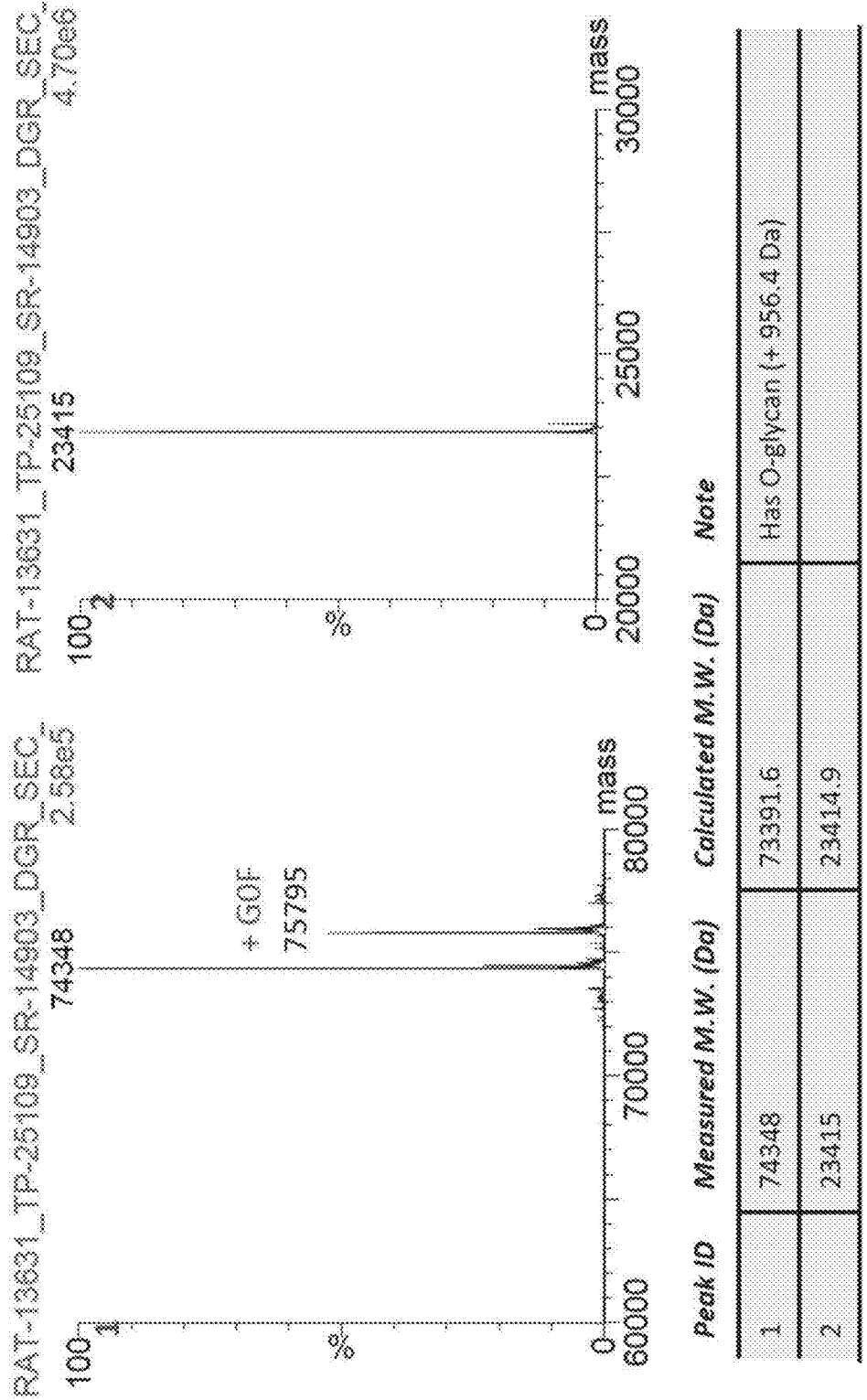
FIG. 11. QXL138AM Analysis of Heavy and Light Chain by Mass Spectrometer.

The construct set forth in FIG. 9 was transiently expressed in TunaCHO for fourteen (14) days. The titer reached 179 mgs/L and was purified by Protein A chromatography using standard methods (Lake Pharma, Belmont, Calif.) (FIG. 10). Further analysis of the heavy and light chain was assessed by mass spectrometer using standard methods ((Lake Pharma, Belmont, Calif.) (FIG. 11).

Example 9: Determination of Ab-Cytokine-Mask Structural Integrity

Figure 12:
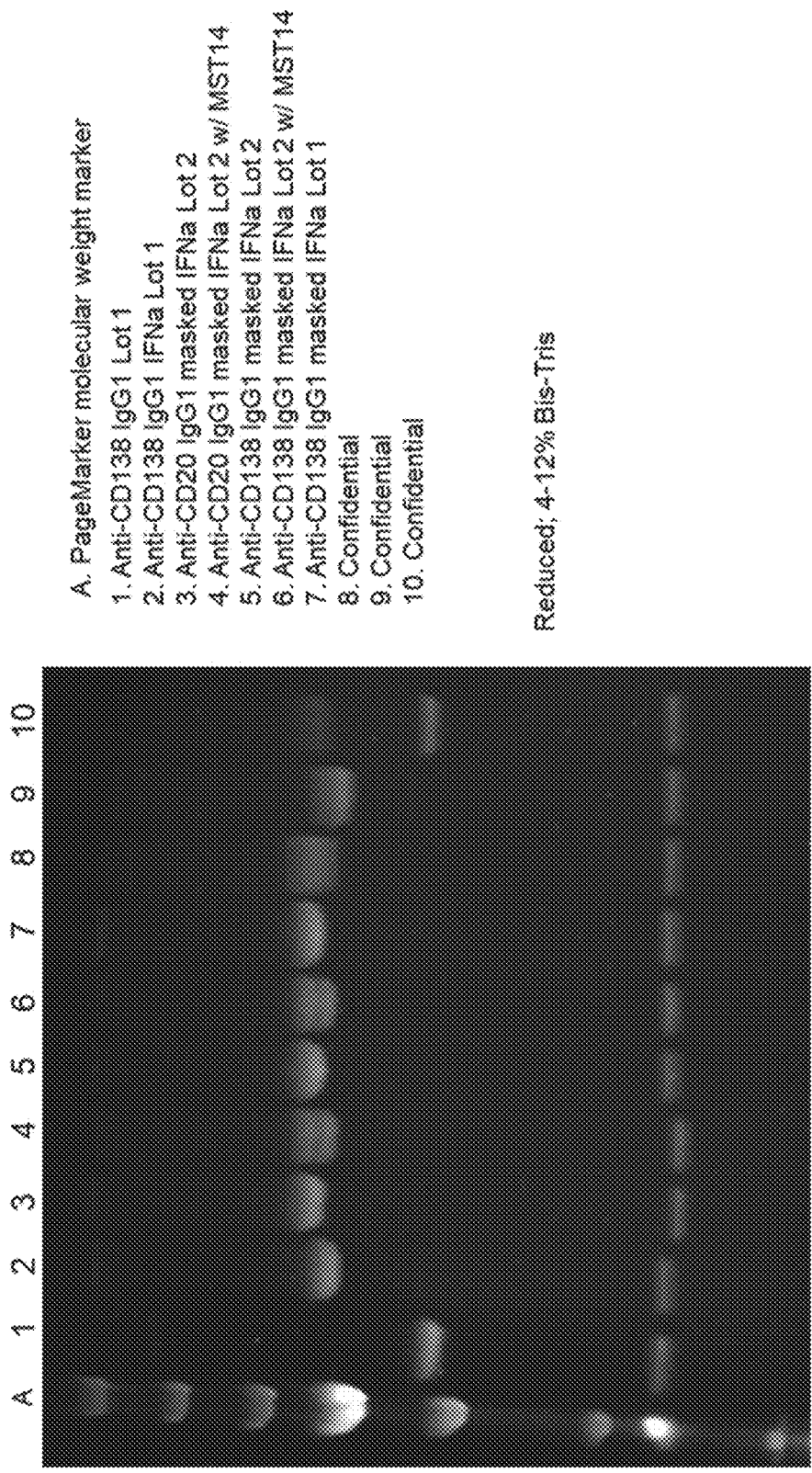
FIG. 12. QXL138AM Characterization by SDS-Page.

In this example, the structural integrity of the Ab-Cytokine-Mask construct of QXL138AM was determined. Briefly, two lots of QXL138AM were evaluated by reducing SDS-PAGE. For samples treated with MST14 (R&D Systems), 8 ug of Ab was incubated with ~125 ng MST14 for 15 min. at 37 deg. C. Then, 2 ug of each purified Ab was denatured by heating to 95 deg. C., reduced with ~2% beta-mercaptoethanol (Sigma), and run on 4-12% Bis-Tris SDS-PAGE gels (Invitrogen). Lot 2 was evaluated +/− pretreatment with Matripase (MST14). The results show the Ab-Cytokine-Mask structure appears intact as purified. Furthermore, the mask is released by MST14 without disruption of the Ab-Cytokine protein. (See, FIG. 12).

Figure 13:
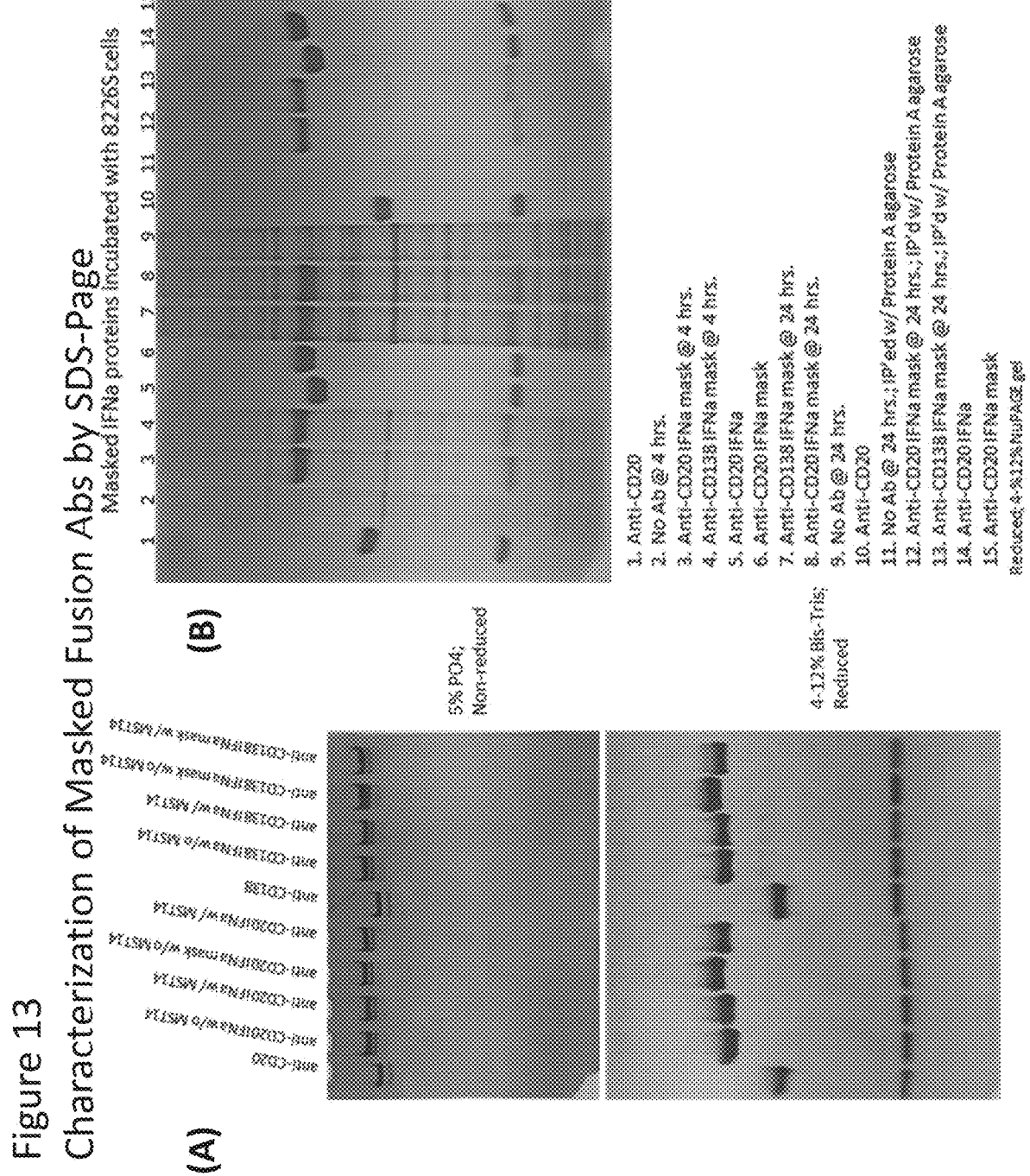
FIG. 13(A-B). Characterization of Masked Fusion Abs by SDS-Page.

Example 10: Determination of Fusion Protein Structural Integrity and Cleavage Specificity In this example, the structural integrity of a plurality of Fusion Abs was determined as well as the ability to cleave the mask by MST14. Briefly, for the samples treated with MST14 (R&D Systems), 50 ug of Ab was incubated with 0.5 ug MST14 for 1 hr. At 37 deg. C. One (1) ug of each purified Ab was denatured by heating to 95 deg. C., reduced with ~2% beta-mercaptoethanol (Thermofisher), and run on 4-12% Bis-Tris SDS-PAGE gels (Invitrogen). 4 ug of each non-reduced Ab was denatured by heating to 95 deg. C and run on 5% PO4 SDS-PAGE gels. 10 ug of indicated masked Abs were incubated with 1×10e6 RPMI 8226S cells in 100 uL of serum-free RPMI (Invitrogen) for 4 hrs. After 4 hrs. cells were spun down for three (3) min. at 500×g and 10 uL of supernatant was denatured by heating to 95 deg. C., reduced with ~2% beta-mercaptoethanol (Thermofisher). The remaining cells were then resuspended and allowed to incubate overnight at 37 deg. C. Then, after approximately 24 hrs. cells were gently spun down and processed as above. The results show the masked Fusion Abs appear the correct size and are specifically cleaved by MST14. (See, FIG. 13(A)).

In a parallel set-up, 10 ug of indicated masked Abs were allowed to incubate with 1×10e6 RPMI 8226S cells in 1 mL of serum-free RPMI (Invitrogen) for 24 hrs. at 37 deg. C. After approximately 24 hrs. cells were spun down as noted in the above paragraph, and the supernatants were immune precipitated with protein A agarose (Sigma). Samples were denatured and reduced as indicated above and run on 4-12% Bis-Tris SDS-PAGE gels. The results show that targeting mask anti-CD138 Fusion Ab to 8226S cells does not affect cleavage of the mask in vitro. (See, FIG. 13(B)).

Example 11: Methods of Binding Fusion Abs to Masking Peptides

In this example, it is shown that a plurality of Fusion Abs specifically binds to several peptide masks of the disclosure. For reference, two (2) peptide masks were tested:

```
Peptide 1 (Mask1):
                                      (SEQ ID NO: 19)
GSGTDVDYYREWSWTQVS;

Peptide 2 (Mask2):
                                      (SEQ ID NO: 20)
GSGTDVDYYREWSWTQV;
```

Figure 14:
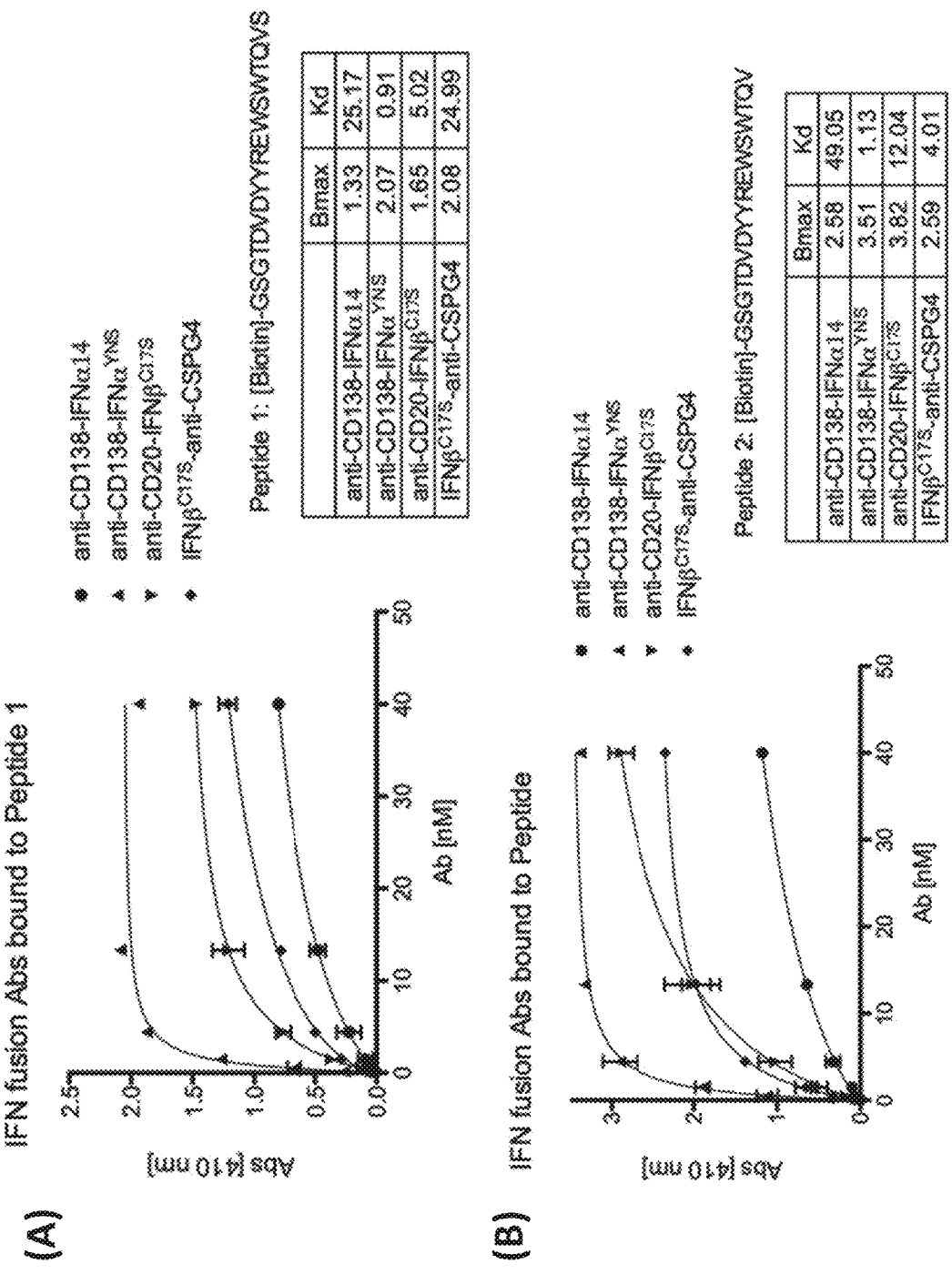
FIG. 14(A-B). Binding of Fusion Abs to Mask by ELISA.

Briefly, Streptavidin coated plates (Pierce) were overlayed with 50 uM of each indicated peptide (Thermofisher) for a minimum of two (2) hrs. at room temperature. Wells were then washed 3× with PBS+0.05% Tween. Abs at the indicated concentrations were then allowed to bind overnight at 4 deg. C. Wells were washed 3× with PBS+0.05% Tween. Bound Abs were detected with anti-human Kappa-AP (Southern Biotech) diluted 1:3000 in PBS+1% BSA. Absorbance changes after addition of AP substrate (Sigma) were assayed at 410 nm using a Biotek EPOCH ELISA reader. The results show Peptide 1 binds all the IFN Fusion Abs tested. (See, FIG. 14(A)). Additionally, Peptide 2 binds to all the IFN Fusion Abs tested in varying degree relative to Peptide 1. (See, FIG. 14(B)).

Example 12: Characterization of Targeted Fusion Abs Versus Non-Targeted Fusion Abs Fusion Abs of the disclosure were tested in several cell lines to compare the effectiveness of targeted fusion Abs versus non-targeted fusion Abs. Briefly, 1×10e4 cells/well (50 uL/well) of each cell line were seeded into 96-well tissue culture plates (Becton Dickinson). The next day cells were treated with 50 uL/well of each indicated Ab at the indicated concentrations. Six (6) days later, 20 uL/well MTS reagent (Promega) was added to the plates. Absorbance changes are read at 490 nm with a Biotek EPOCH reader. The results show that the Targeted Fusion Abs are more effective than the Non-Targeted Fusion Abs. (See, FIG. 15(A) & FIG. 15(B)).

In another experiment, 1.5×10e4 U266 cells/well (50 uL/well) or 1×10e4 CAPAN-2 cells/well (50 uL/well) were seeded into 96-well tissue culture plates (Becton Dickinson). U266 cells were treated the same day, while CAPAN-2 cells were treated the next day with 50 uL/well of each indicated Ab at the indicated concentrations. Six (6) days after treatment, 20 uL/well MTS reagent (Promega) was added to the plates. Absorbance changes are read at 490 nm with a Biotek EPOCH reader. The results show that the Targeted Fusion Abs are more effective than the Non-Targeted Fusion Abs. In addition, the masked Fusion Ab is less effective than the cleaved version. (See, FIG. 16(A) & FIG. 16(B)).

Example 13: Methods of Inhibiting Cell Proliferation Using Anti-CD138-IFNα2

Figure 17:
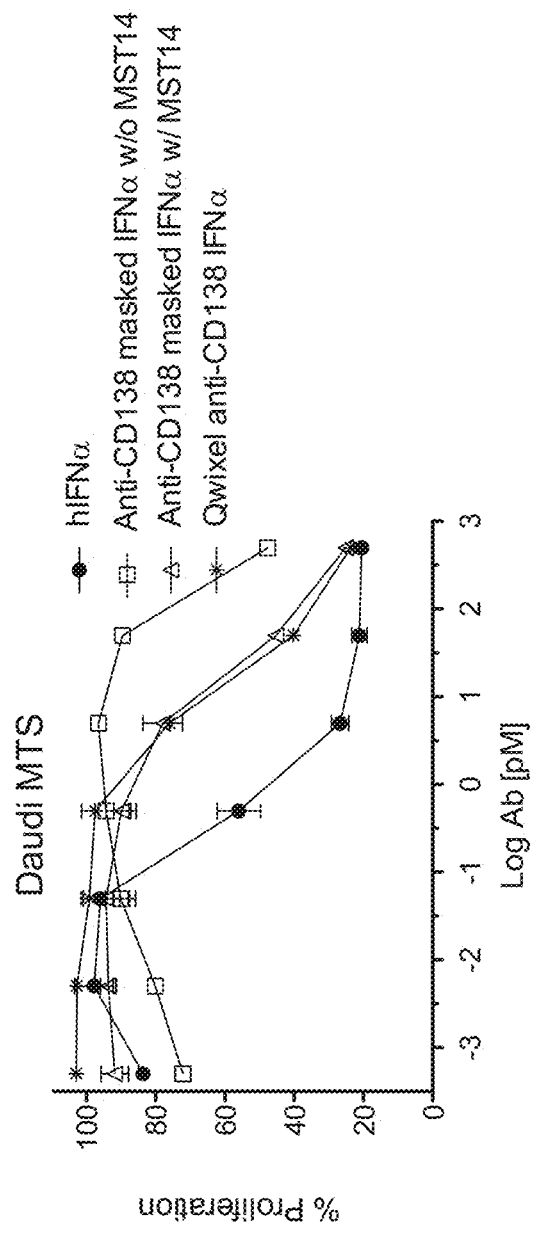
FIG. 17. Removal of the IFN Mask Restores Inhibition of Cell Proliferation.

In this example, it is shown that the IFN fusion protein (anti-CD138-IFNα2) inhibits cell proliferation in a cancer cell (i.e. Daudi cell). The inhibition of the proliferation of cancer cells significantly decreased while the IFN mask was in place. Subsequent to removing the IFN mask, the inhibition of the cell proliferation was restored. Briefly, Daudi cells were incubated with hIFNα2, anti-CD138 masked IFNα2 w/o MST14, anti-CD138 masked IFNα2 w MST14; and an anti-CD138-IFNα2 for three (3) days and the proliferation was measured using the MTS assay. It is noted that proliferation is expressed as the percentage (%) relative to untreated cells. The results show that removal of the IFN mask restores inhibition of cell proliferation. (See, FIG. 17).

Example 14: Methods of Reducing Off-Target IFNα-Induced Cytotoxicity

Figure 18:
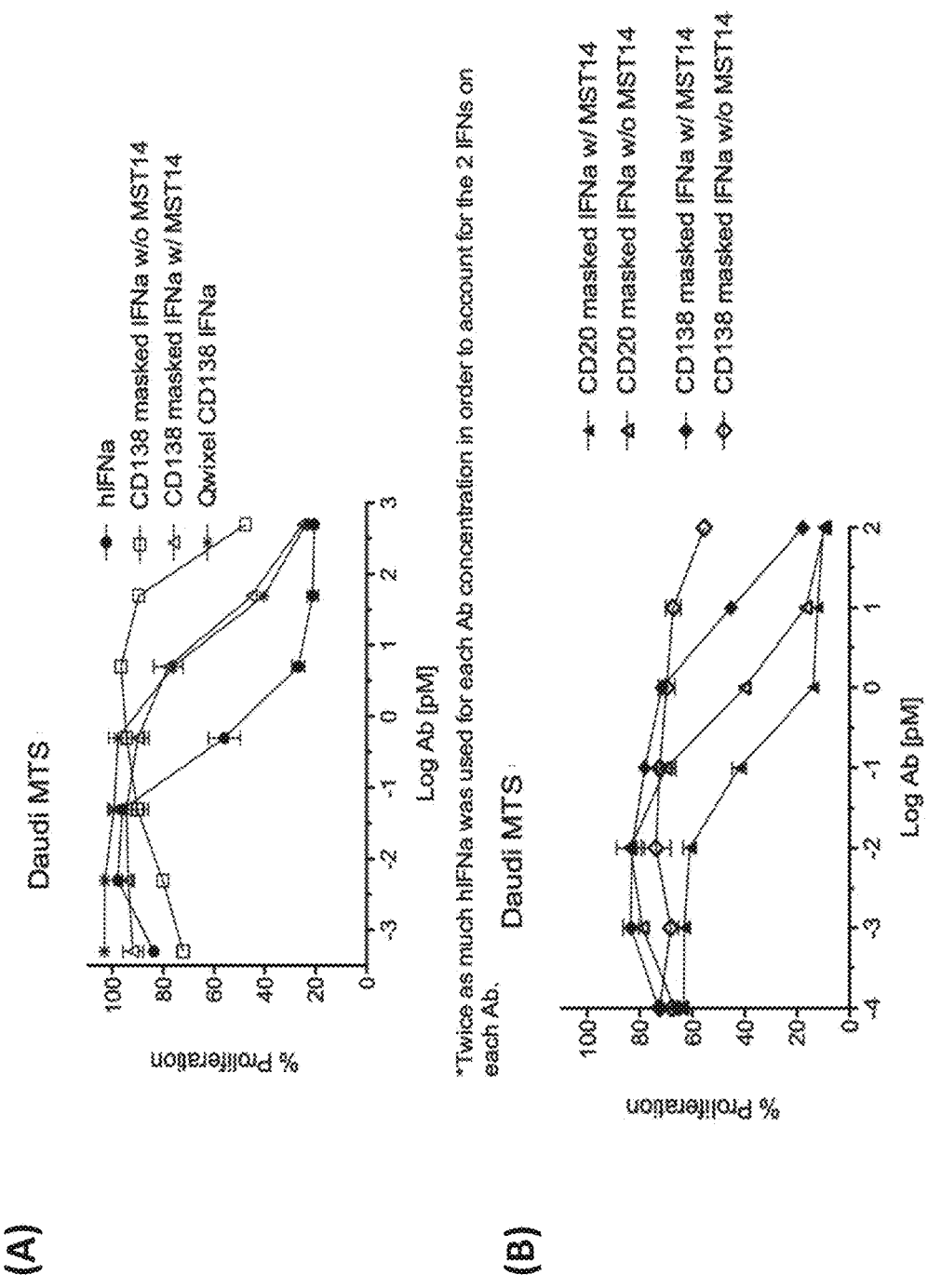
FIG. 18(A-B). Ab Targeting and Masking Facilitate Reduction in off Target IFNα-Induced Cytotoxicity. FIG.

In this experiment, the ability of the mask was shown to reduce off-target IFNα-induced cytotoxicity. Briefly, 1×10e4 cells/well (50 uL/well) of each cell line were seeded into 96-well tissue culture plates (Becton Dickinson). 50 uL/well of each indicated Ab at the indicated concentrations were added to the plates. Three (3) days later, 20 uL/well MTS reagent (Promega) was added to the plates. Absorbance changes are read at 490 nm with a Biotek EPOCH reader. For samples treated with MST14 (R&D Systems), 50 ug of Ab was incubated with 0.5 ug MST14 for 1 hr. At 37 deg. C. The results show that the CD138 Fusion Protein and the cleaved CD138 Fusion Protein are approximately 50× less potent that free IFNα on CD138 cells and the masked CD138 Fusion Protein is approximately 1000× less potent that IFNα on CD138 cells (See, FIG. 18(A)). Additionally, masking reduces on or off target activity by about 10× in cell culture. Ab targeting to the cell surface enhances activity by approximately 100×. The targeted unmasked Fusion Protein is approximately 10,000× more potent that the untargeted masked Fusion Protein. (See, FIG. 18(B)).

Figure 19:
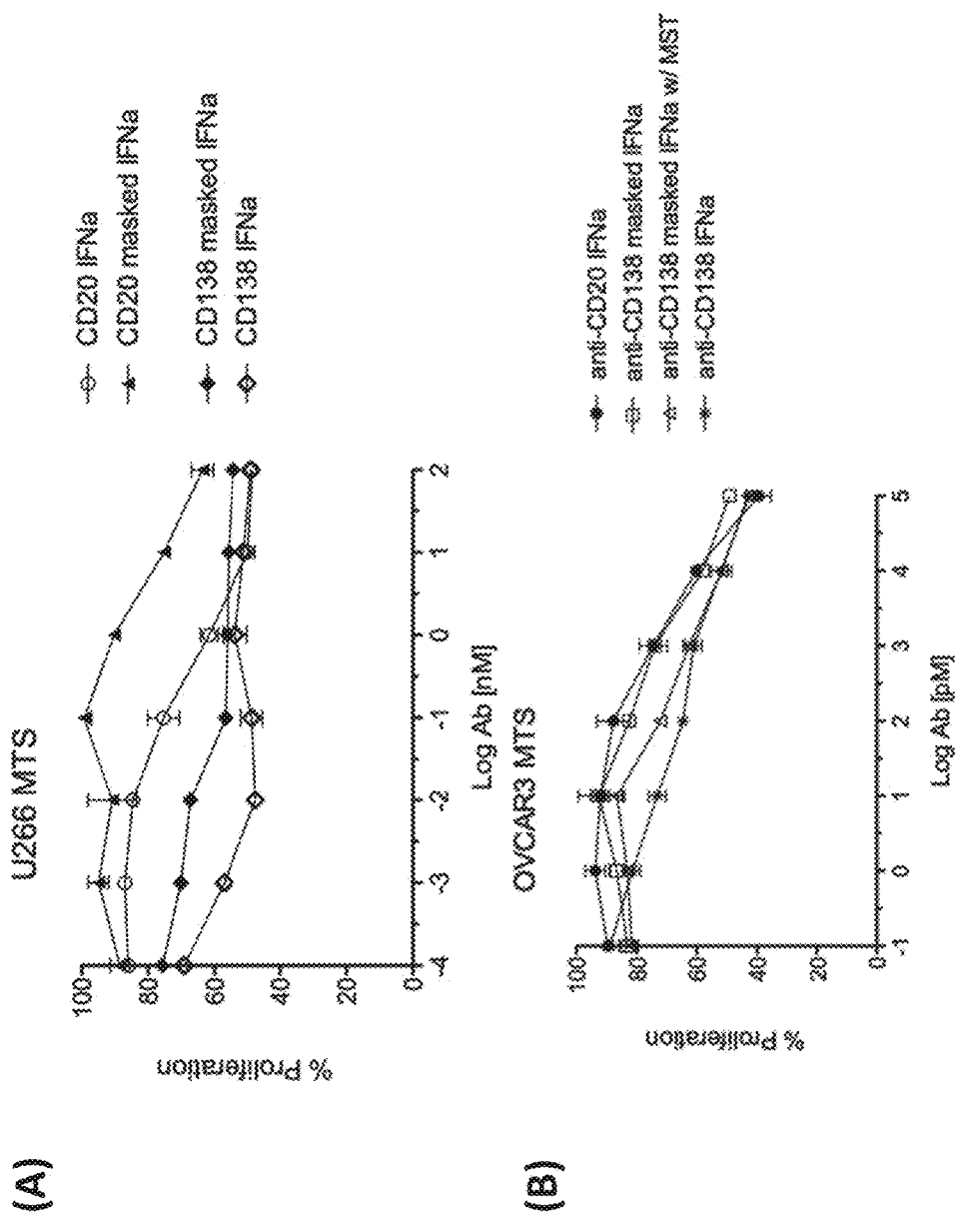
Figure 20:
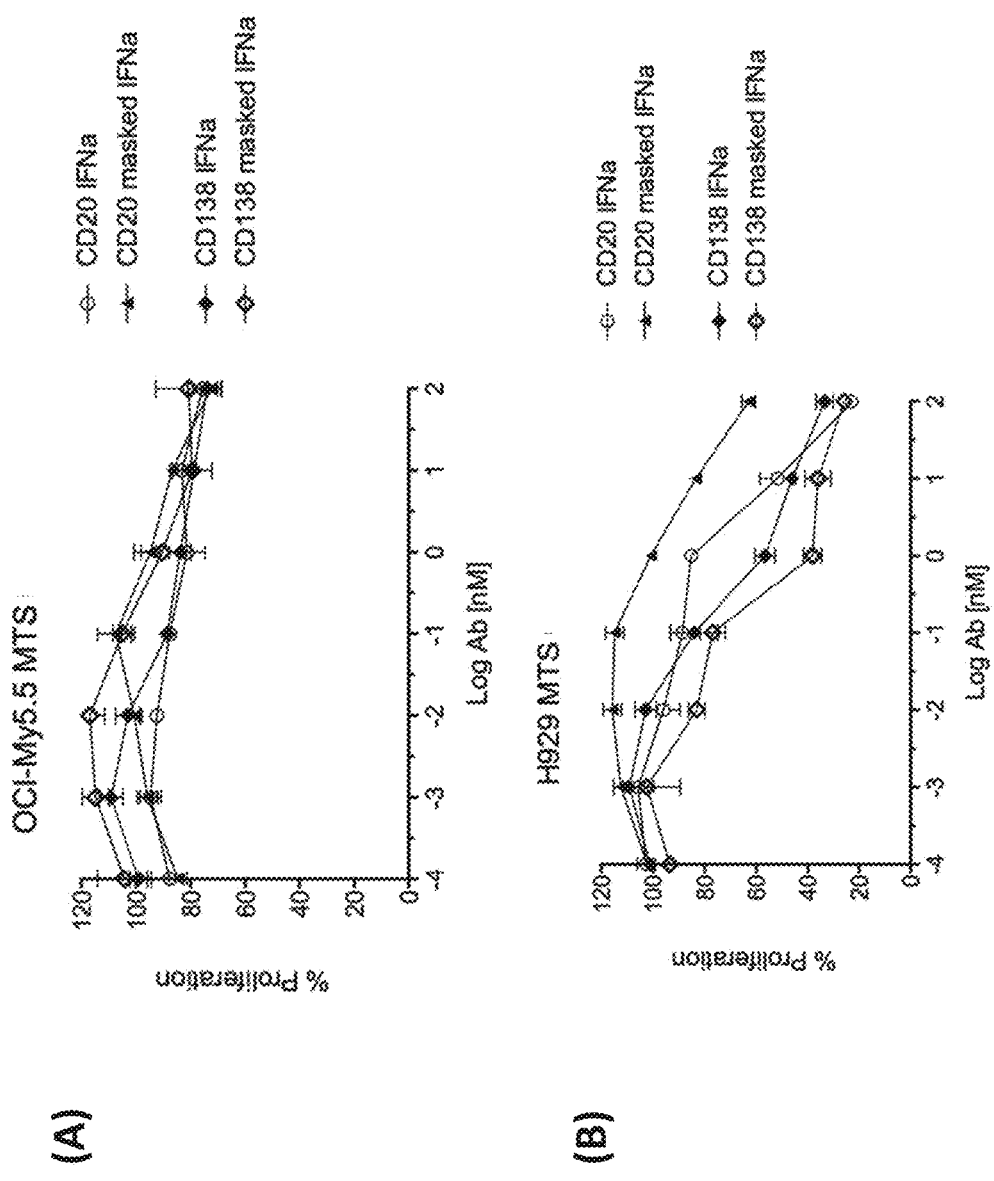

Example 15: Tumor Cell Line Cytotoxicity of Masked Versus Unmasked & Targeted Versus Untargeted Fusion Proteins Studies comparing the cytotoxicity of various cell lines using Masked versus Unmasked & Targeted versus Untargeted Fusion Proteins of the disclosure were performed using the following protocol. Briefly, 1.5×10e4 U266, H929, or OCI-My5.5 cells/well (50 uL/well) were seeded into 96-well tissue culture plates (Becton Dickinson). Additionally, 1×10e4 OVCAR3 or BCMW1 cells/well (50 uL/well) were seeded into 96-well tissue culture plates (Becton Dickinson). The U266, H929, or OCI-My5.5 cells were treated the same day, while OVCAR3 or BCMW1 cells were treated the next day with 50 uL/well of each indicated Ab at the indicated concentrations. U266, H929, or OCI-My5.5 were assayed four (4) days after treatment by adding 20 uL/well MTS reagent (Promega) to the plates and measuring absorbance changes at 490 nm with a Biotek EPOCH reader. OVCAR3 or BCMW1 cells were assayed similarly after six (6) days of treatment. The results show antigen targeting increases the anti-proliferative effects of the masked and unmasked fusion antibodies relative to their non-targeted counterparts. In addition, masking the interferon moiety reduces the fusion antibody's anti-proliferative effect relative to their unmasked counterparts in the cell lines assayed. (See, FIGS. 19 and 20).

Example 16: Methods of Reducing IFNR Activation of PBMCs

In this experiment, freshly thawed human PBMCs (HumanCells Biosciences) were washed once with cold RPMI+10% FBS (Invitrogen) and seeded into a 12-well plate (Themofisher) at a density of ~1×10e6 cells/well (1 mL/well). Any Fc receptor expression was blocked/reduced with addition of 167 nM human Fc Block (Becton Dickinson) to the cells for one (1) hr. before proceeding with the experiment. Recombinant human IFNα (Novus Biologicals) or indicated Abs were added to the cells and allowed to incubate at 37 deg. C for an additional 7 hrs. Abs cleaved with MST14 (R&D Systems) were prepared by incubating 50 ug of Ab with 0.5 ug of MST14 for 1 hr. At 37 deg. C. After 7 hrs. incubation, cells were spun down for 3 min. at 500×g and 20 uL of supernatant from each sample was assayed for IP-10 (Abcam) by ELISA according the manufacturer's protocol.

Additionally, A Western blot was done on the cell pellets from the same experiment. Cells were lysed with 100 uL NDET (1% Nonidet P-40, 0.4% deoxycholate, 66 mM EDTA, and 10 mM Tris, pH 7.4). 10 uL/sample were denatured by heating to 95 deg. C., reduced with ~2% beta-mercaptoethanol (Thermofisher), and run on a 4-12% Bis-Tris SDS-PAGE gel (Invitrogen). Proteins were transferred to a 0.45 um PVDF membrane (GE Healthcare) and blocked O/N at 4 deg. C with PBS+3% BSA (Thermofisher). The membrane was then blotted with rabbit anti-pSTAT1 (Cell Signaling) 1:3000 in PBS+3% BSA O/N at 4 deg. C. After three 10-minute washes with PBS+0.1% Tween (Sigma), the blot was incubated with anti-rabbit IgG-HRP diluted 1:10000 in PBS+3% BSA for 1 hr. At RT. Following another three (3), ten (10) minute washes with PBS+0.1% Tween, the blot was incubated with SuperSignal West Pico HRP substrate (Pierce). Blot images were captured using an Azure 280 (Azure Biosystems). Immediately after blot image capture, the blot was washed 3× with PBS+0.1% Tween and incubated with rabbit anti-GAPDH diluted 1:20000 in PBS+3% BSA O/N @ 4 deg. C.

Detection was accomplished as described previously. Lastly, the blot was stripped by heating it to 65 deg. C for 15 min. in 10 mM Tris pH 6.8+2% SDS+0.7% beta-mercaptoethanol. After four (4), ten (10) minute washes with PBS+0.1% Tween, the blot was re-blocked with PBS+3% BSA and blotted with rabbit anti-STAT1 diluted 1:1000 in PBS+3% BSA O/N at 4 deg. C. Detection followed as described previously.

Figure 21:
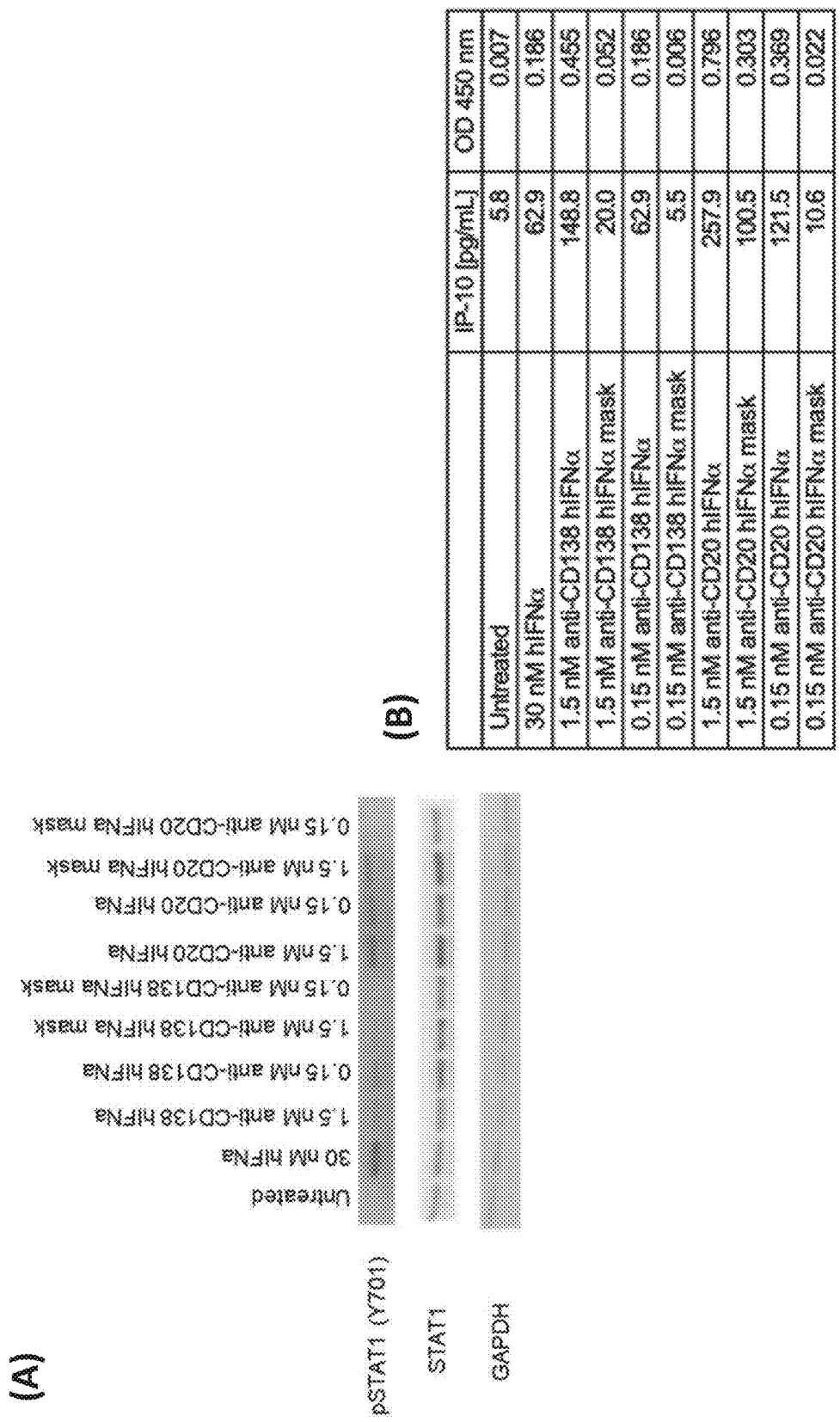

The results show there is a dose dependent STAT1 activation where masked Fusion Protein activates STAT1 less effective compared to equimolar concentrations of unmasked Fusion Protein. (See, FIG. 21(A)). In addition, FIG. 21(B) shows there is a dose dependent induction of IP-10 where masked Fusion Protein induces IP-10 less effectively compared to equimolar concentrations of unmasked Fusion Protein.

Figure 22:
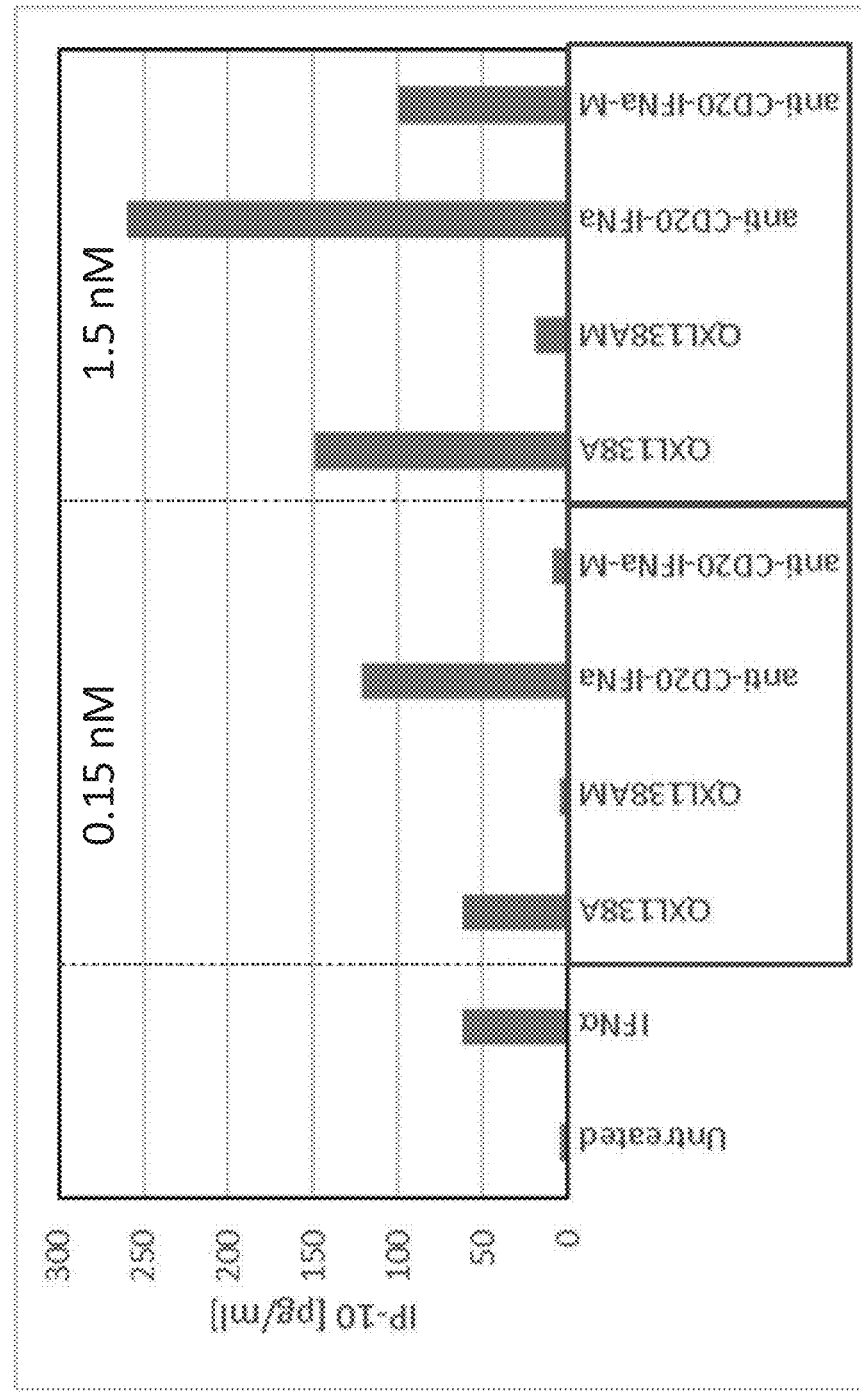

In another experiment, freshly thawed human PBMCs (HumanCells Biosciences) were washed once with cold RPMI+10% FBS (Invitrogen) and seeded into a 12-well plate (Themofisher) at a density of ~1×10e6 cells/well (1 mL/well). Any Fc receptor expression was blocked/reduced with addition of 167 nM human Fc Block (Becton Dickinson) to the cells for 1 hr. before proceeding with the experiment. Recombinant human IFNα (Novus Biologicals) or indicated Abs were added to the cells and allowed to incubate at 37 deg. C for an additional 7 hrs. Abs cleaved with MST14 (R&D Systems) were prepared by incubating 50 ug of Ab with 0.5 ug of MST14 for 1 hr. At 37 deg. C. After a seven (7) hr. incubation, cells were spun down for 3 min. at 500×g and 20 uL of supernatant from each sample was assayed for IP-10 (Abcam) by ELISA according the manufacturer's protocol. The results show that masking the IFNα significantly reduces (>10×) the potency of IP-10 induction. (See, FIG. 22).

Example 17: QXL138AM Functional Studies In Vitro

Figure 23:
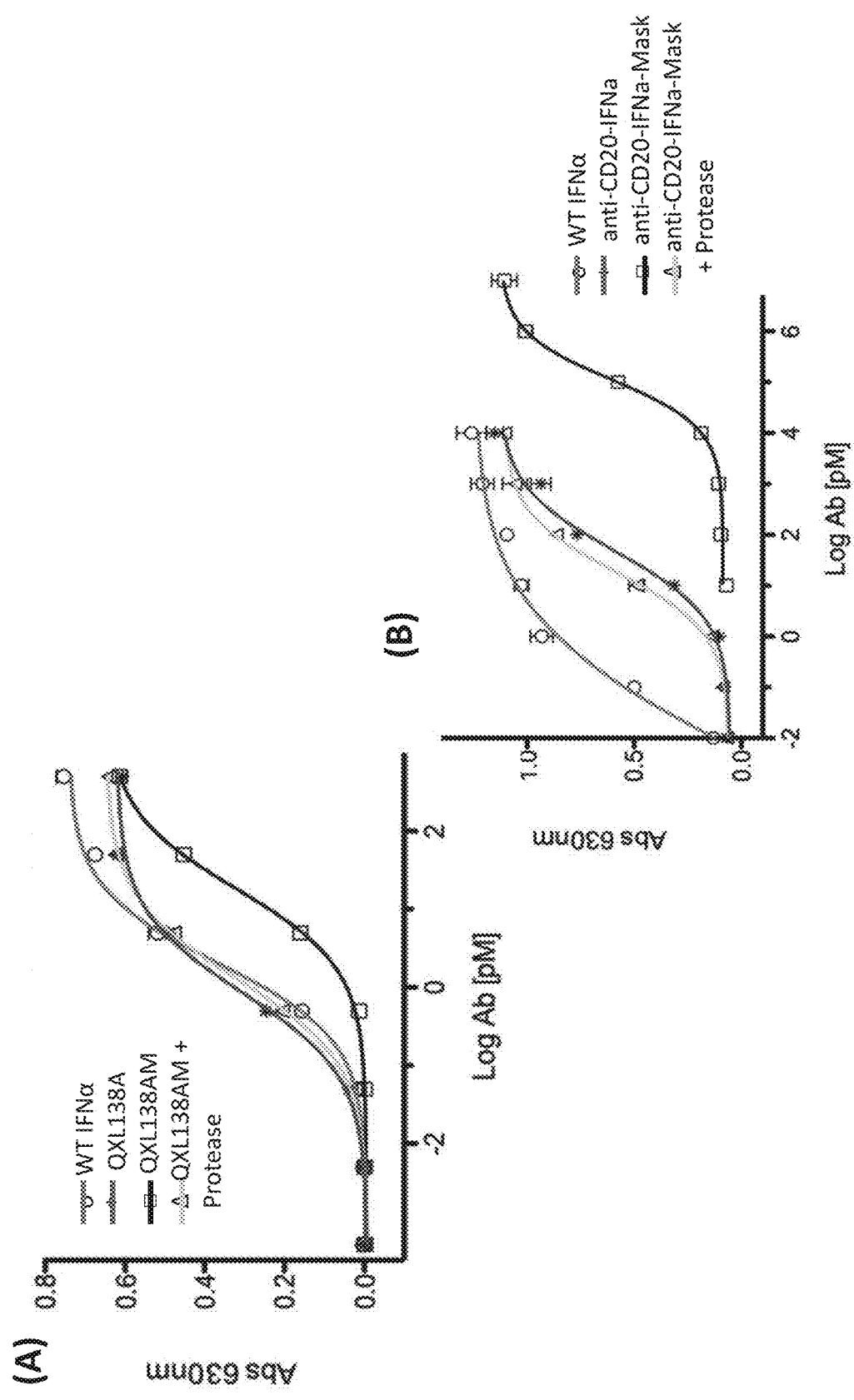

A study of the functional characterization of QXL138AM was performed using the following protocol. Briefly, HEK Blue IFNa/b cells (Invivogen) were seeded into 96-well tissue culture plates (Fisher) at a density of 5×10e4 cells/well (50 uL/well). Then fifty (50) uL/well of recombinant IFNα (Novus Biologicals) or indicated Abs were incubated with the cells at the indicated concentrations overnight at 37 deg. C. Abs cleaved with MST14 (R&D Systems) were prepared by incubating 50 ug of Ab with 0.5 ug of MST14 for 1 hr. At 37 deg. C. Ten (10) uL of supernatant was then added to a plate containing 90 uL/well Quanti-Blue substrate (Invivogen). Absorbance changes were read at 630 nm using a Biotek EPOCH ELISA reader. The results show (i) The Fusion Ab targeted IFNα is a potent as the wild type IFNα, (ii) the Non-Targeted Ab-IFNα is approximately 100× less potent that wild type IFNα, (iii) the mask is effective at blocking Non-Targeted IFNα, and (iv) the mask reduces IFNα activity even when targeted to transformed (non-tumorigenic) HEK cells expressing CD138. (See, FIG. 23(A) & FIG. 23(B)).

Example 18: QXL138AM Efficacy Studies In Vivo

Figure 24:
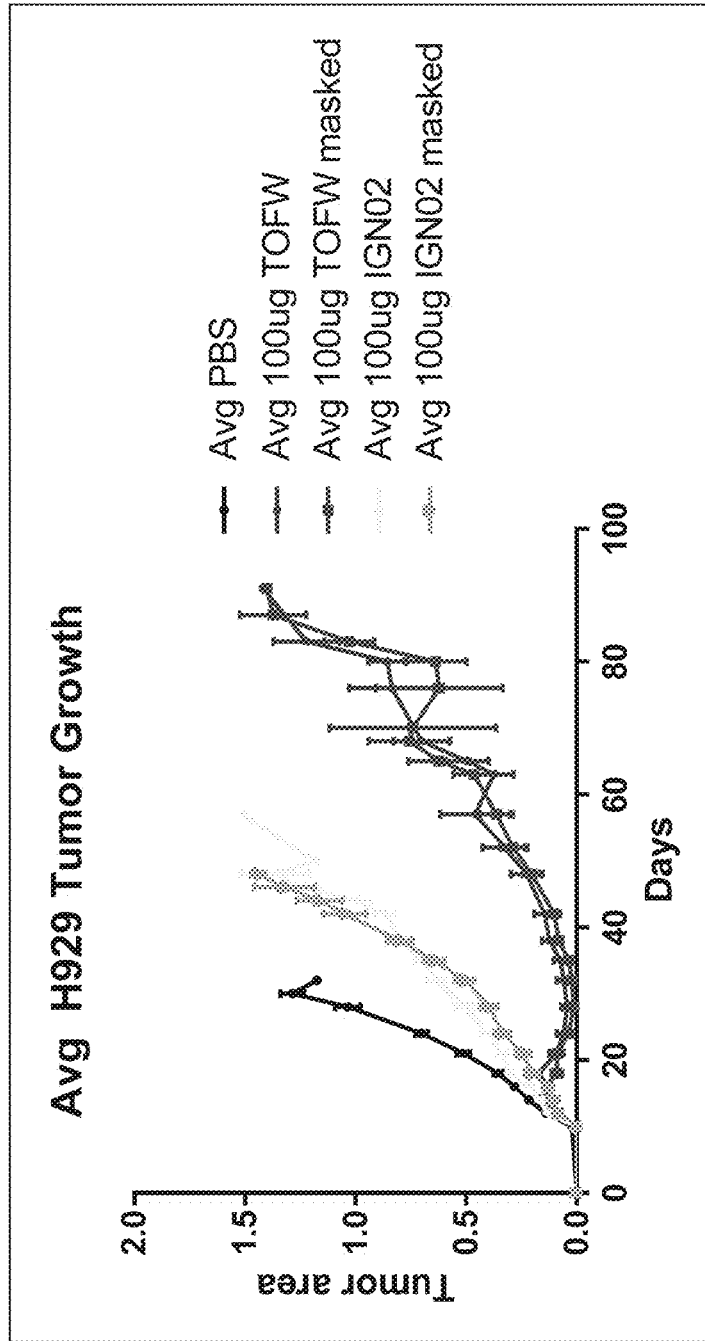
Figure 25:
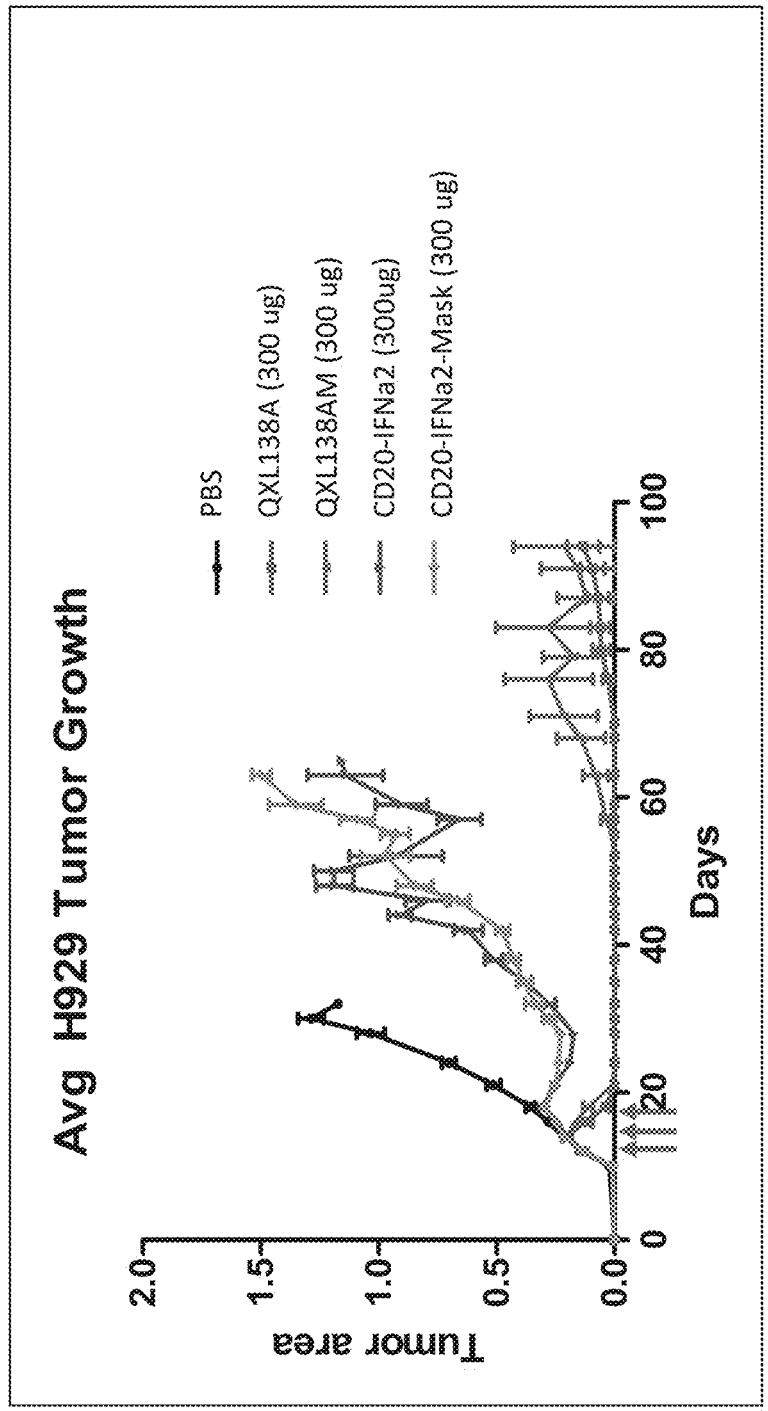

Efficacy studies of QXL138AM were performed using the following protocols. Briefly, 1×10^6 H929 cells were injected with matrigel (BD) s.c on the back of NSG mice. Mice were treated on day(s) 14, 16, and 18 post infection with 100 ug (5 mg/kg left graph) and 300 ug (15 mg/kg right graph) i.v. Tumor size area was measured three (3) times a week until they grew greater than 1.4 cm, at which point they were sacrificed. Targeted fusion protein was compared to non-targeted fusion protein. The masked versions of each were also compared. The results show that (i) QXL138AM is as potent as QXL138A and (ii) single agent QXL138A & QXL138AM is capable of achieving durable CRs that last for several months post treatment. (See, FIGS. 24 & 25).

Figure 26:
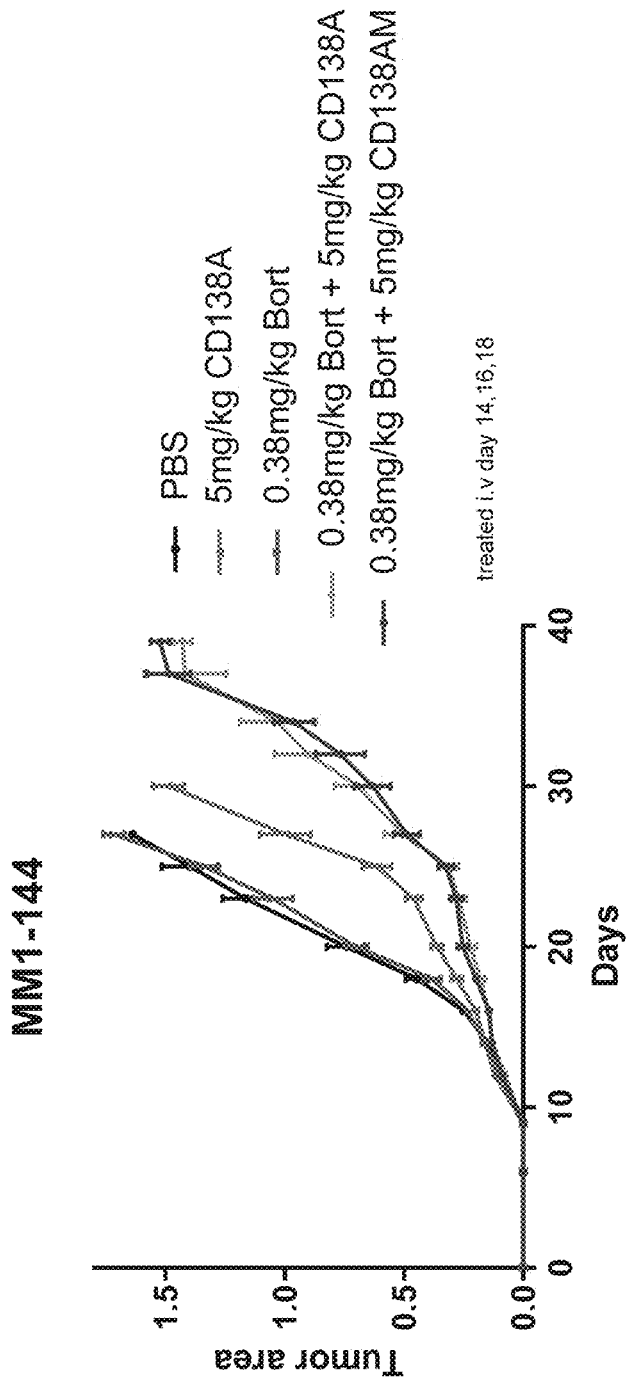

In another experiment, synergies with standard of care in myeloma (bortezomib) is shown. Briefly, 5×10^6 MM1-144 cells were injected with matrigel (BD) s.c on the back of NSG mice. Mice were treated on day(s) 14, 16, and 18 post infection with 100 ug (5 mg/kg) with fusion protein alone i.v, targeted masked and unmasked fusion protein were treated in combination with 0.38 mg/kg bortezomib i.v, or with 0.38 mg/kg of bortezomib i.v alone. Tumor size area was measured three (3) times a week until they grew greater than 1.4 cm, at which point they were sacrificed. The results show that both the masked and unmasked IFNα are synergistic and show similar efficacy when used with bortezomib. (See, FIG. 26).

Figure 27:
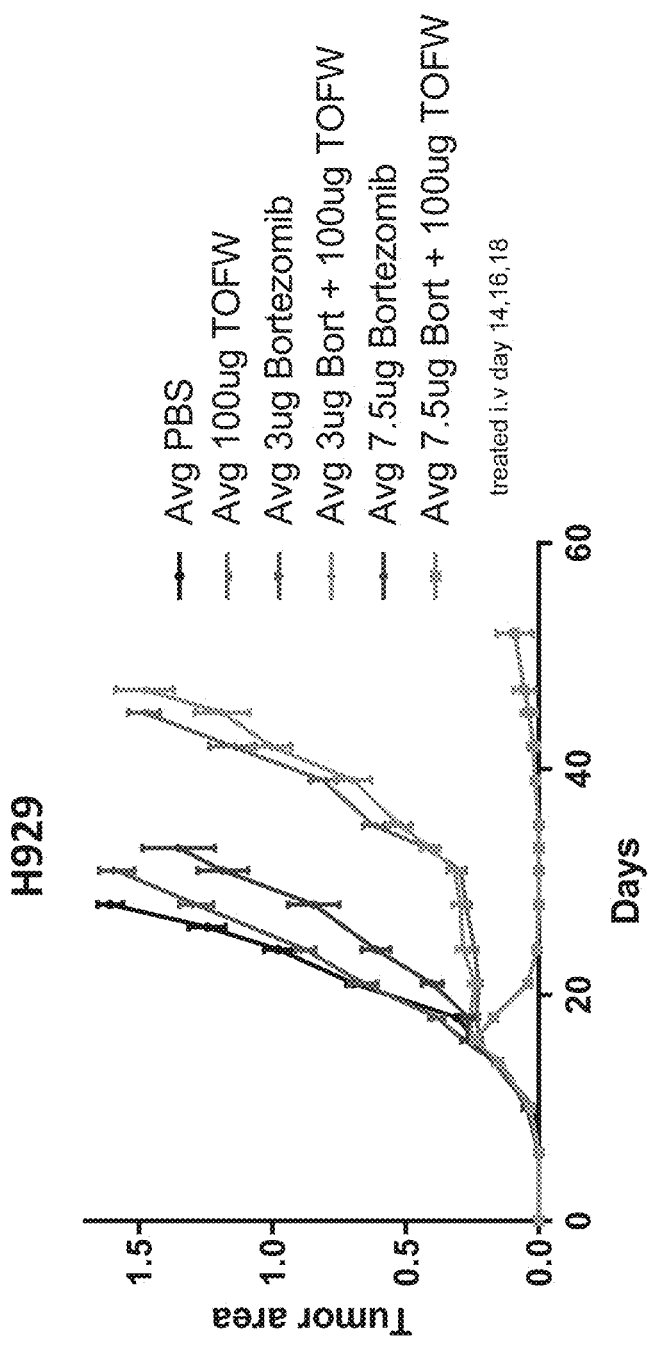

In another experiment, 1×10^6 H929 cells were injected with matrigel (BD) s.c on the back of NSG mice. Mice were treated on day(s) 14, 16, and 18 post injection with 100 ug (5 mg/kg) with fusion protein alone i.v, 0.38 mg/kg bortezomib alone i.v, or 0.15 mg/kg bortezomib alone i.v. Targeted fusion protein (QXL138A) was treated in combination with 0.38 mg/kg bortezomib i.v, or with 0.15 mg/kg of bortezomib i.v. Tumor size area was measured three (3) times a week until they grew greater than 1.4 cm, at which point they were sacrificed. The results show a synergistic effect of QXL138A and bortezomib in H929 cells in vivo. (See, FIG. 27).

Figure 28:
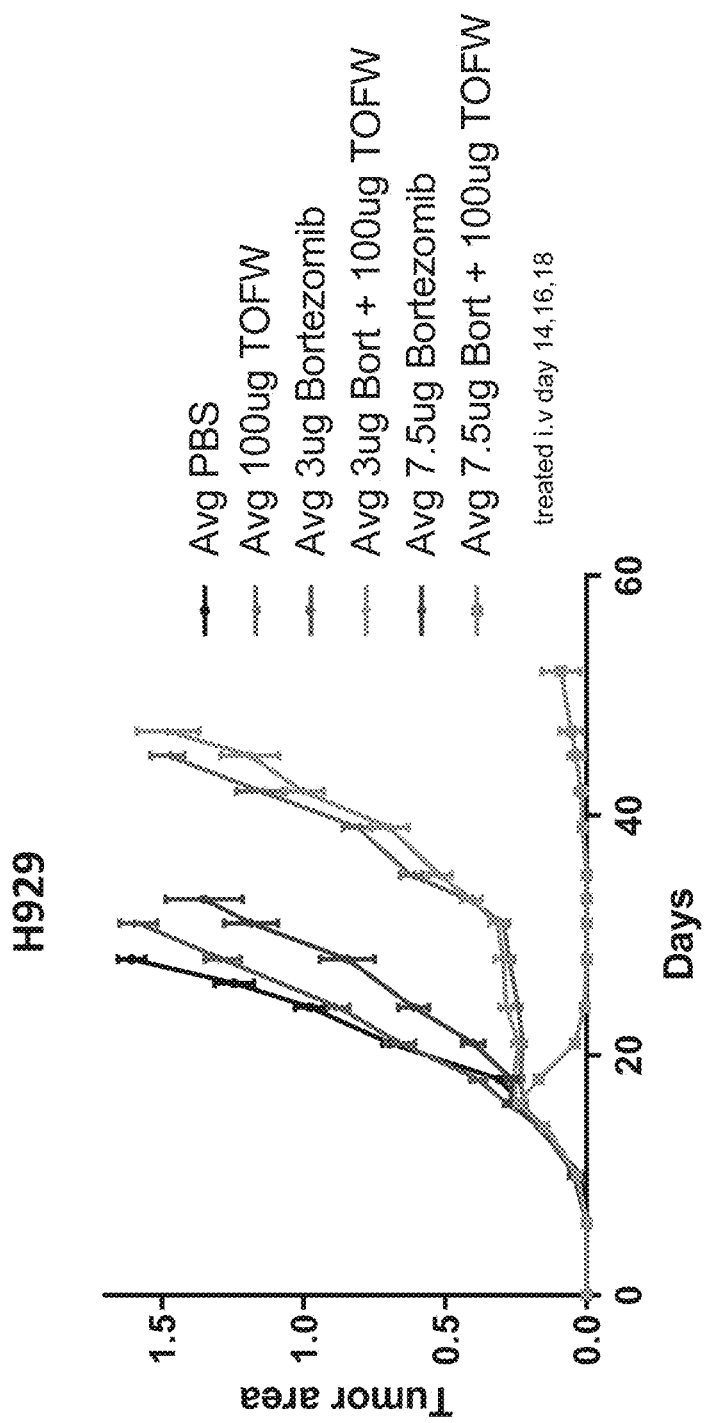

In another experiment, synergies with standard of care in myeloma (pomalidomide) is shown. Briefly, 1×10^6 H929 cells were injected with matrigel (BD) s.c on the back of NSG mice. Mice were treated on day(s) 14, 16, and 18 post injection with 100 ug (5 mg/kg) with fusion protein alone i.v or 500 ug (25 m/kg) pomalidomide alone i.v. Unmasked fusion protein (QXL183A) was treated in combination with 25 mg/kg pomalidomide i.v and tumor size area was measured three (3) times a week until they grew greater than 1.4 cm, at which point they were sacrificed. The results show a synergistic effect with QXL138AM and pomalidomide). (See, FIG. 28).

Figure 29:
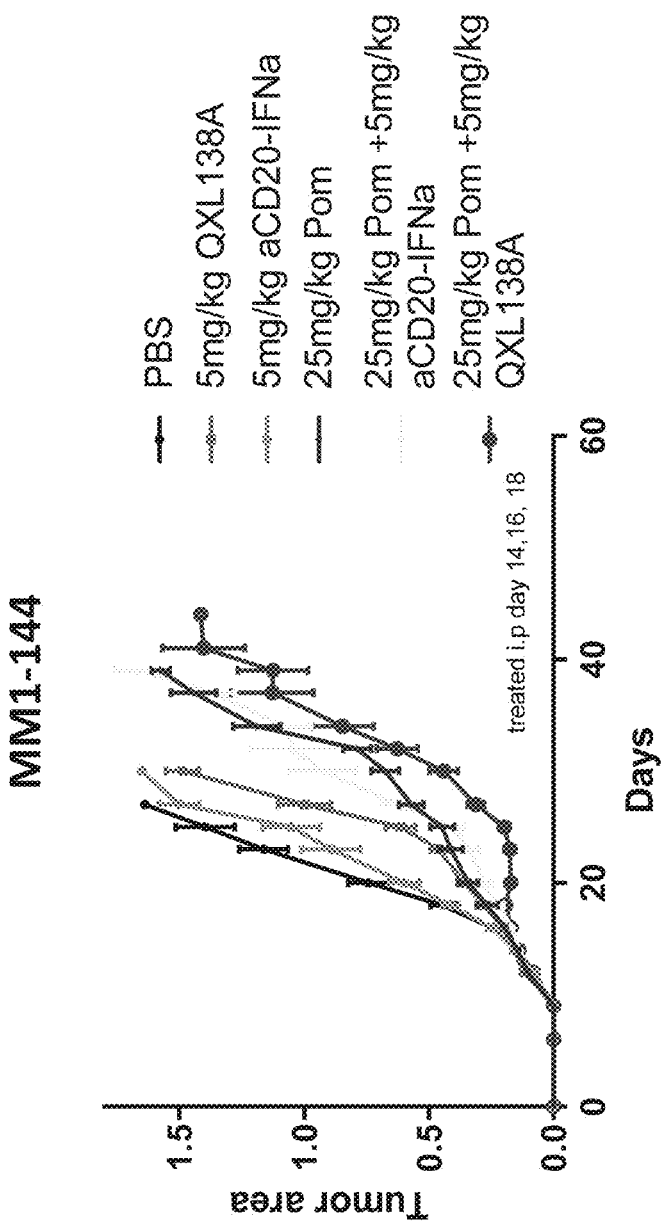
FIG. 29. QXL138AM Shows Synergies with Standard of Care Treatment (Pomalidomide) in Myeloma.

In another experiment, 5×10^6 MM1-144 cells were injected with matrigel (BD) s.c on the back of NSG mice. Mice were treated on day(s) 14, 16, and 18 post injection with 100 ug (5 mg/kg) with fusion protein (QXL138A) i.v alone or untargeted fusion protein i.v alone, or 25 mg/kg pomalidomide i.p alone. 25 mg/kg pomalidomide i.p was treated in combination with 5 mg/kg targeted fusion protein (QXL138A) i.v or 5 mg/kg untargeted fusion protein i.v. Tumor size area was measured three (3) times a week until they grew greater than 1.4 cm, at which point they were sacrificed. The results show a synergistic effect with QXL138A and pomalidomide. (See, FIG. 29).

Example 19: Characterization of Targeted Masked IFNα2 Fused to Anti-CD138 Using a Second Mask (anti-CD138-IFNα2-Mask2)

Figure 30:
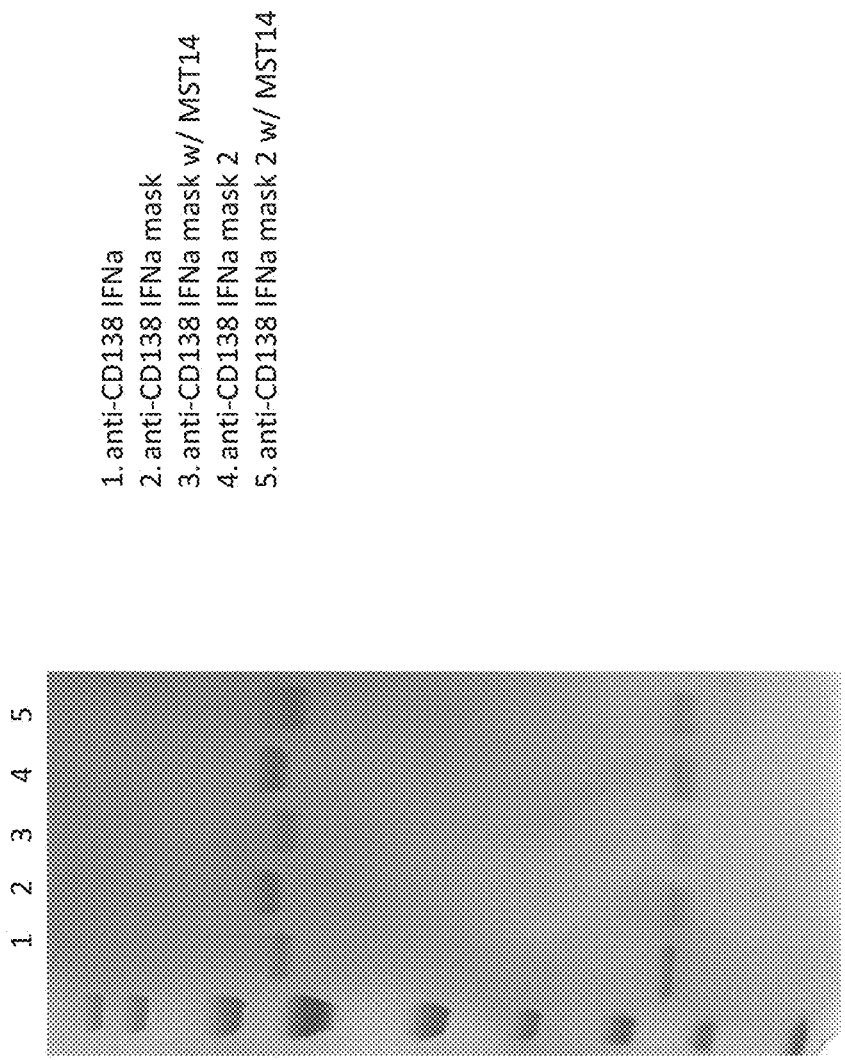
FIG. 30. Matriptase ST 14 Cleaves a Second IFN Mask from the Heavy Chain of an anti-CD138 Fusion.

In this example, it is shown that a second IFN mask (mask2) can be cleaved from the Heavy chain using Matripase ST 14. Briefly, for samples treated with MST14 (R&D Systems), 50 ug of Ab was incubated with 0.5 ug MST14 for 1 hr. At 37 deg. C. Then, one (1) ug of each purified Ab was denatured by heating to 95 deg. C., reduced with ~2% beta-mercaptoethanol (Thermofisher), and run on 4-12% Bis-Tris SDS-PAGE gels (Invitrogen). The resulting analysis shows that Matripase ST 14 efficiently cleaves the IFN mask (mask2) on the anti-CD138 Fusion Ab. (See, FIG. 30).

Example 20: Binding of Masked Fusion Abs (Utilizing Mask2) to IFNα2 Receptor

Figure 31:
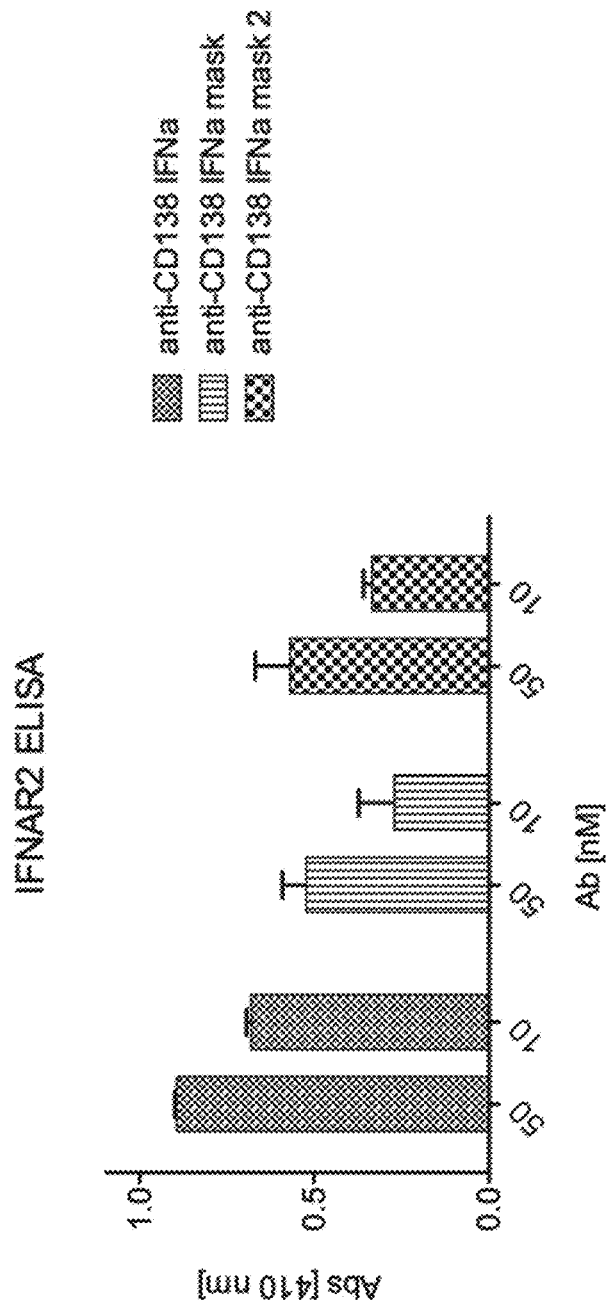
FIG. 31. Masked anti-CD138 (Mask1) Fusion Abs and Masked anti-CD138 (Mask2) Fusion Abs Bind IFNα2 Receptor with reduced affinity relative to unmasked fusion protein.

In this example, it is shown that a Masked Fusion Ab (utilizing mask2) of the disclosure can bind to the IFNα2 receptor. Briefly, Immulon 2 HB plates (Thermofisher) were coated with 10 ug/mL IFNαR2 (R&D Systems) overnight at 4 deg. C and blocked with 2% BSA (Fisher) for a minimum of 2 hrs. at room temperature. Then, wells were washed 3× with PBS+0.05% Tween (Sigma). Indicated Ab concentrations were overlayed overnight at 4 deg. C. Wells were then washed 3× with PBS+0.05% Tween. Bound Abs were detected with anti-human Kappa-AP (Southern Biotech) diluted 1:3000 in PBS+1% BSA. Absorbance changes after addition of AP substrate (Sigma) were assayed at 410 nm using a Biotek EPOCH ELISA reader. The results show that both mask1 and mask2 are able to inhibit Fusion Ab binding to IFNαR2. (See, FIG. 31).

Example 21: Methods of Reducing and Restoring Masked IFNα Activity

Figure 32:
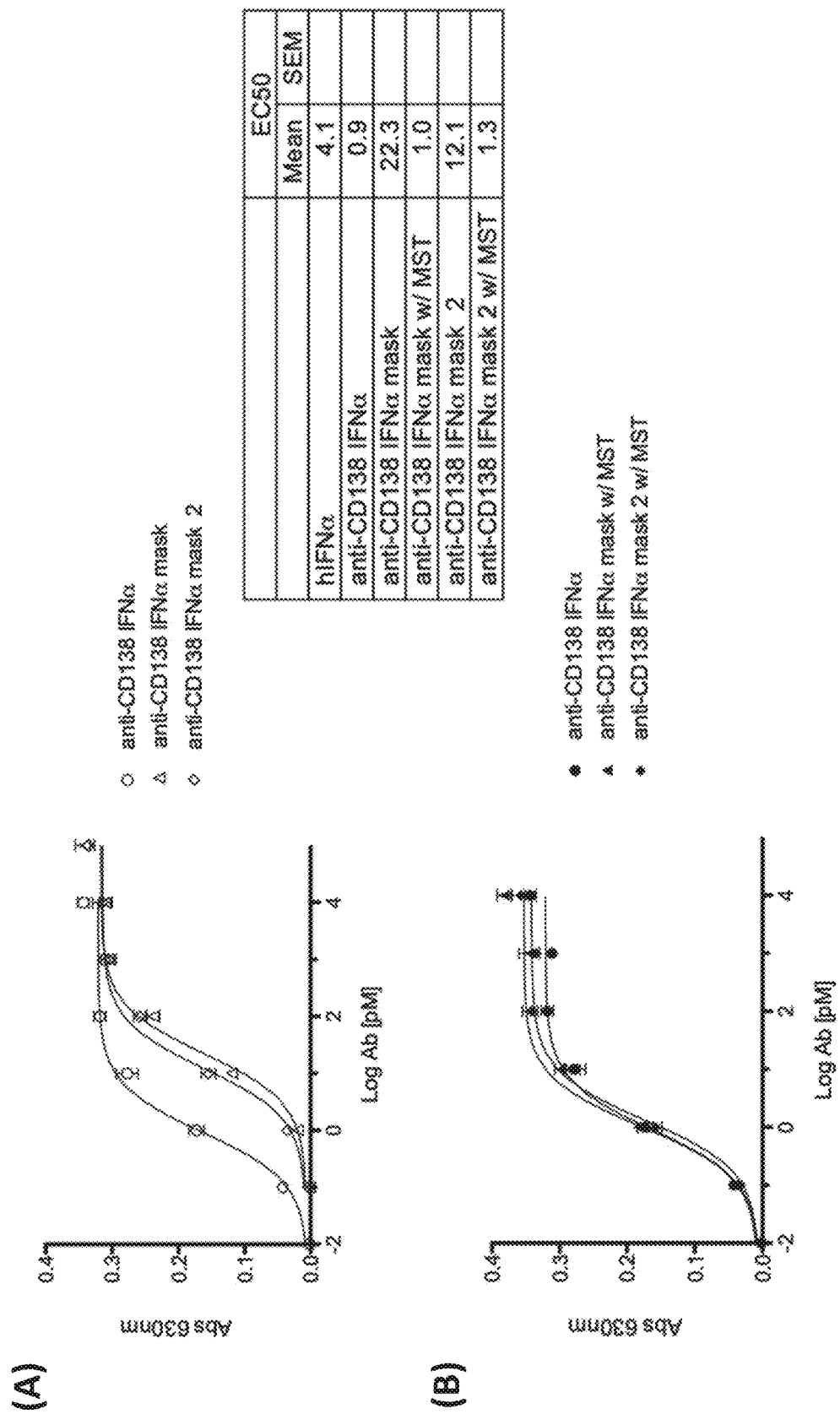
FIG. 32(A-B). Methods of Reducing and Restoring masked IFNα Activity.

In this example, it is shown that both Mask1 and Mask2 of the disclosure can reduce and restore IFNα activity. Briefly, HEK Blue IFNa/b cells (Invivogen) were seeded into 96-well tissue culture plates (Fisher) at a density of 1×10e4 cells/well (50 uL/well). 50 uL/well of recombinant IFNα (Novus Biologicals) or indicated Abs (5T4 or Mesothelin) were incubated with the cells at the indicated concentrations overnight at 37 deg. C. Abs cleaved with MST14 (R&D Systems) were prepared by incubating 50 ug of Ab with 0.5 ug of MST14 for 1 hr. At 37 deg. C. Then, 10 uL of supernatant was added to a plate containing 90 uL/well Quanti-Blue substrate (Invivogen). Absorbance changes were read at 630 nm using a Biotek EPOCH ELISA reader. The results show that the IFNα activity in masked anti-CD138-IFNα (Mask1) and masked anti-CD138-IFNα (Mask2) was reduced compared to when the mask is cleaved. (See, FIG. 32(A) & FIG. 32(B)).

Example 22: Characterization of Targeted Masked IFNα1 Fused to Anti-PSCA (Anti-PSCA-IFNα1)

In this example, it is shown that the IFN mask can be cleaved from the H chain using Matriptase ST 14. Briefly, anti-PSCA-IFNα1 and anti-PSCA-IFNα1+mask is generated using the procedures set forth, supra. See, *Methods of Masking IFNs of the Disclosure*. The modified heavy chain is transiently expressed in 293T cells with the appropriate L chain yielding anti-PSCA-IFNα1+mask in 293T cells. Confirmation by SDS-PAGE analysis shows that the fusion protein is correctly assembled in H2L2 molecules with H and L chains of appropriate size. FACS analysis shows the modified fusion protein binds to PSCA expressing cells. The resulting analysis shows that Matriptase ST 14 can cleave the IFN mask from the H chain. Anti-PSCA-IFNα1 without a mask is used as a control.

Example 23: Characterization of Targeted Masked IFNα2 Fused to Anti-PSCA (Anti-PSCA-IFNα2)

In this example, it is shown that the IFN mask can be cleaved from the H chain using Matriptase ST 14. Briefly, anti-PSCA-IFNα2 and anti-PSCA-IFNα2+mask is generated using the procedures set forth, supra. See, *Methods of Masking IFNs of the Disclosure*. The modified heavy chain is transiently expressed in 293T cells with the appropriate L chain yielding anti-PSCA-IFNα2+mask in 293T cells. Confirmation by SDS-PAGE analysis shows that the fusion protein is correctly assembled in $H_2L_2$ molecules with H and L chains of appropriate size. FACS analysis shows the modified fusion protein binds to PSCA expressing cells. The resulting analysis shows that Matriptase ST 14 can cleave the IFN mask from the H chain. Anti-PSCA-IFNα2 without a mask is used as a control.

Example 24. Methods of Inhibiting Tumor Growth Utilizing Targeted Masked IFN Fusion Proteins In Vivo The significant expression of TAAs in tumor cells, together with the restrictive expression in normal cells makes TAAs of the disclosure, and preferably TAAs expressed in solid tumor cancer a good target for targeted masked IFN fusion protein therapy. Thus, the therapeutic efficacy of targeted masked IFN fusion protein which bind a TAA expressed in human cancer xenograft mouse models is evaluated.

Masked IFN fusion protein efficacy on tumor growth and metastasis formation is studied in mouse cancer xenograft models (e.g. subcutaneous and orthotopically).

Subcutaneous (s.c.) tumors are generated by injection of $5 \times 10^4$-$10^6$ cancer cells mixed at a 1:1 dilution with Matrigel (Collaborative Research) in the right flank of SCID mice. To test masked IFN fusion protein efficacy on tumor formation the masked IFN fusion protein injections are started on the same day as tumor-cell injections. As a control, mice are injected with either purified human IgG or PBS; or a purified MAb that recognizes an irrelevant antigen not expressed in human cells. In preliminary studies, no difference is found between control IgG or PBS on tumor growth. Tumor sizes are determined by caliper measurements, and the tumor volume is calculated as width$^2$×Length/2, wherein width is the smallest dimension and length is the largest dimension. Mice with subcutaneous tumors greater than 1.4 cm in diameter are sacrificed.

An advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff et al., Clin Cancer Res. (2001) 7:2870; Solesvik et al., Eur J Cancer Clin Oncol. (1984) 20:1295). The effect of antibody and small molecule on neovascularization is studied in accordance with procedures known in the art, such as by IHC analysis of tumor tissues and their surrounding microenvironment.

It is shown that masked IFN fusion proteins which bind a TAA that is expressed in human cancers inhibits tumor growth in vivo.

Example 25: Human Clinical Trials for the Treatment of Human Carcinomas Through the Use of Masked IFN Fusion Protein which Bind Specific TAAs Masked IFN fusion protein which bind specific TAAs are synthesized in accordance with the present invention which specifically accumulate in a tumor cell and are used in the treatment of certain tumors and other immunological disorders and/or other diseases. In connection with each of these indications, two clinical approaches are successfully pursued.

I.) Adjunctive therapy: In adjunctive therapy, patients are treated with masked IFN fusion protein which bind specific TAAs in combination with a chemotherapeutic or pharmaceutical or biopharmaceutical agent or a combination thereof. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the masked IFN fusion protein which bind specific TAAs in monotherapy of tumors, the masked IFN fusion protein which bind specific TAAs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single masked IFN fusion protein which bind specific TAA injection may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the masked IFN fusion protein which bind a specific TAA, and the particular therapeutic or prophylactic effect to be achieved, and (b) the limitations inherent in the art of compounding such an compound for the treatment of sensitivity in individuals.

Clinical Development Plan (CDP)

The CDP follows and develops treatments of cancer(s) and/or immunological disorders using masked IFN fusion protein which bind specific TAAs of the disclosure in connection with adjunctive therapy or monotherapy. Trials initially demonstrate safety and thereafter confirm efficacy in repeat doses. Trials are open label comparing standard chemotherapy with standard therapy plus masked IFN fusion protein which bind specific TAAs. As will be appreciated, one non-limiting criteria that can be utilized in connection with enrollment of patients is concentration of masked IFN fusion protein which bind specific TAAs in a tumor as determined by standard detection methods known in the art.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Select Tumor Associated Antigen(s).

| | | |
|---|---|---|
| CD138 | HPV E6 E7 | CEA |
| MUC1 | EGFRvIII | STEAP |
| LMP2 | HER-2/neu | MART1 |
| CD20 | TMPRSS2 | PSMA |
| gp100 | NA17 | PLAC1 |
| EGFR | B7-H4 | GM3 |
| PR1 | ALK | BORIS |
| FAP | NECTIN-4 | Tn |
| Tyrosinase | Cyclin B1 | GloboH |
| Folate Receptor Alpha | CSPG4 | ETV6-AML |
| PSA | RCC | NY-BR-1 |
| SLC34A2 | TRP-2 | RGS5 |
| EphA2 | GD3 | SART3 |
| PAP | Fucosyl GM1 | STn |
| B7-H3 | Mesothelin | PAX5 |
| AFP | PSCA | OY-TES1 |
| EpCAM | MAGE A1 | SLITRK6 |
| AKAP-4 | XAGE 1 | TAA |
| 5T4 | CD38 | GPR94 |
| SSX2 | AXL | CD-37 |

TABLE II

List of Interferon(s) and functional mutants.

| Approved Symbol | Approved Name |
|---|---|
| IFNA1 | Interferon alpha 1 |
| IFNA2 | Interferon alpha 2 |
| IFNA4 | Interferon alpha 4 |
| IFNA5 | Interferon alpha 5 |
| IFNA6 | Interferon alpha 6 |
| IFNA7 | Interferon alpha 7 |
| IFNA8 | Interferon alpha 8 |
| IFNA10 | Interferon alpha 10 |
| IFNA11P | Interferon alpha 11 |
| IFNA12P | Interferon alpha 12 |
| IFNA13 | Interferon alpha 13 |
| IFNA14 | Interferon alpha 14 |
| IFNA16 | Interferon alpha 16 |
| IFNA17 | Interferon alpha 17 |
| IFNA20P | Interferon alpha 20, pseudogene |
| IFNA21 | Interferon alpha 21 |
| IFNA22P | Interferon alpha 22, pseudogene |
| IFNB1 | Interferon beta 1 |
| YNS | |
| IFNA | |

TABLE III

Amino Acid Abbreviations.

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

The invention claimed is:

1. A composition, comprising the polypeptide sequence TDVDYYREWSWTQV (SEQ ID NO: 14), wherein said polypeptide sequence masks the activity of a Type-I interferon (IFN) and wherein said composition further comprises a fusion protein which is fused to an antibody that binds to a tumor associated antigen.

2. The composition of claim 1, further comprising a flexible peptide linker.

3. The composition of claim 1, further comprising a tumor associated protease cleavage site.

4. The composition of claim 1, wherein the Type-I interferon comprises IFNα1.

5. The composition of claim 1, wherein the Type-I interferon comprises IFNα2.

6. The composition of claim 1, wherein the Type-I interferon comprises IFNα4.

7. The composition of claim 1, wherein the Type-I interferon comprises IFNα5.

8. The composition of claim 1, wherein the Type-I interferon comprises IFNα6.

9. The composition of claim 1, wherein the Type-I interferon comprises IFNα14.

10. The composition of claim 1, wherein the Type-I interferon comprises IFNβ1.

11. The composition of claim 1, wherein the Type-I interferon or functional mutant thereof is selected from IFNA1 (Interferon alpha 1), IFNA2 (Interferon alpha 2), IFNA4 (Interferon alpha 4), IFNA5 (Interferon alpha 5), IFNA6 (Interferon alpha 6), IFNA7 (Interferon alpha 7), IFNA8 (Interferon alpha 8), IFNA10 (Interferon alpha 10), IFNA11P (Interferon alpha 11), IFNA12P (Interferon alpha 12), IFNA13 (Interferon alpha 13), IFNA14 (Interferon alpha 14), IFNA16 (Interferon alpha 16), IFNA17 (Interferon alpha 17), IFNA20P (Interferon alpha 20, pseudogene), IFNA21 (Interferon alpha 21), IFNA22P (Interferon alpha 22, pseudogene), IFNB1 (Interferon beta 1), YNS mutant, or IFNA (Interferon alpha).

12. The composition of claim 1, wherein the Tumor Associated Antigen comprises CD138.

13. The composition of claim 1, wherein the Tumor Associated Antigen comprises CD20.

14. The composition of claim 1, wherein the Tumor Associated Antigen comprises mesothelin.

15. The composition of claim 1, wherein the Tumor Associated Antigen comprises 5T4.

16. The composition of claim 1, wherein the Tumor Associated Antigen is selected from CD138, HPV E6 E7, CEA, MUC1, EGFRvIII, STEAP, LMP2, HER-2/neu, MART1, CD20, TMPRSS2, PSMA, gp100, NA17, PLAC1, EGFR, B7-H4, GM3, PR1, ALK, BORIS, FAP, NECTIN-4, Tn, Tyrosinase, Cyclin B1, GloboH, Folate Receptor Alpha, CSPG4, ETV6-AML, PSA, RCC, NY-BR-1, SLC34A2, TRP-2, RGS5, EphA2, GD3, SART3, PAP, Fucosyl GM1, STn, B7-H3, Mesothelin, PAX5, AFP, PSCA, OY-TES1, EpCAM, MAGE A1, SLITRK6, AKAP-4, XAGE 1, TAA, 5T4, CD38, GPR94, SSX2, AXL, or CD-37.

17. A Targeted Masked IFN comprising:

a. an antibody comprising a heavy chain and/or a light chain which specifically binds to a tumor associated antigen;

b. a Type-I interferon, wherein the N-terminal of said Type-I interferon is fused to the C-terminal of said antibody heavy and/or light chains; and c. an interferon mask comprising the polypeptide sequence TDVDYYREWSWTQV (SEQ ID NO: 14) whereby said interferon mask.

18. The Targeted Masked IFN of claim 17, wherein the N-terminal of said Type-I interferon is fused to the C-terminal of said antibody heavy and/or light chain further comprising a flexible peptide linker.

19. The Targeted Masked IFN of claim 17, wherein the interferon mask of SEQ ID NO: 14is attached to the C-terminal of said Type-I interferon further comprising a flexible peptide linker.

20. The Targeted Masked IFN of claim 18, further comprising a tumor associated protease cleavage site inserted between said antibody and said flexible peptide linker.

21. The Targeted Masked IFN of claim 17, further comprising a tumor associated protease cleavage site inserted between said Type-I interferon and said interferon mask.

22. The Targeted Masked IFN of claim 17, wherein said Type-I IFN or functional mutant thereof comprises IFNA1 (Interferon alpha 1), IFNA2 (Interferon alpha 2), IFNA4 (Interferon alpha 4), IFNA5 (Interferon alpha 5), IFNA6 (Interferon alpha 6), IFNA7 (Interferon alpha 7), IFNA8 (Interferon alpha 8), IFNA10 (Interferon alpha 10), IFNA11P (Interferon alpha 11), IFNA12P (Interferon alpha 12), IFNA13 (Interferon alpha 13), IFNA14 (Interferon alpha 14), IFNA16 (Interferon alpha 16), IFNA17 (Interferon alpha 17), IFNA20P (Interferon alpha 20, pseudogene), IFNA21 (Interferon alpha 21), IFNA22P (Interferon alpha 22, pseudogene), IFNB1 (Interferon beta 1), YNS mutant, or IFNA (Interferon alpha).

23. The Targeted Masked IFN of claim 17, wherein said antibody binds a tumor associated antigen selected from CD138, HPV E6 E7, CEA, MUC1, EGFRvIII, STEAP, LMP2, HER-2/neu, MART1, CD20, TMPRSS2, PSMA, gp100, NA17, PLAC1, EGFR, B7-H4, GM3, PR1, ALK, BORIS, FAP, NECTIN-4, Tn, Tyrosinase, Cyclin B1, GloboH, Folate Receptor Alpha, CSPG4, ETV6-AML, PSA, RCC, NY-BR-1, SLC34A2, TRP-2, RGS5, EphA2, GD3, SART3, PAP, Fucosyl GM1, STn, B7-H3, Mesothelin, PAX5, AFP, PSCA, OY-TES1, EpCAM, MAGE A1, SLITRK6, AKAP-4, XAGE 1, TAA, 5T4, CD38, GPR94, SSX2, AXL, or CD-37.

24. The Targeted Masked IFN of claim 17, wherein said antibody binds CD138.

25. The Targeted Masked IFN of claim 17, wherein said antibody binds CD20.

26. The Targeted Masked IFN of claim 17, wherein said antibody binds mesothelin.

27. The Targeted Masked IFN of claim 17, wherein said antibody binds 5T4.

28. A method of making the Targeted Masked IFN of claim 17, the method comprising expressing a construct encoding the Targeted Masked IFN in a host cell.

29. A pharmaceutical composition comprising the Targeted Masked IFN of claim 17.

30. A kit comprising the Targeted Masked IFN of claim 17.

31. A method of treating cancer in a subject, comprising administering to said subject a therapeutically effective amount of the Targeted Masked IFN of claim 17, wherein, optionally, the subject is a human subject.

* * * * *

SEQUENCE LISTING

```
<160> NUMBER OF SEQ ID NOS: 21

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 5
```

-continued

```
<212> TYPE: PRT
<213> ORGANISM: Artificial Sequence
<220> FEATURE:
<223> OTHER INFORMATION: Synthetic

<400> SEQUENCE: 2

Gly Gly Gly Gly Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Ser Gly Gly Gly Gly Ser
1               5

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Ala Gly Ala Ala Ala Lys Gly Ala Ala Ala Lys Ala Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ser Gly Gly Ala Gly Gly Ser
1               5

<210> SEQ ID NO 6
<211> LENGTH: 475
<212> TYPE: PRT
<213> ORGANISM: Artificial Sequence
<220> FEATURE:
<223> OTHER INFORMATION: Synthetic

<400> SEQUENCE: 6

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Gln Ser Gly
                20                  25                  30

Ser Glu Leu Met Met Pro Gly Ala Ser Val Lys Ile Ser Cys Lys Ala
            35                  40                  45

Thr Gly Tyr Thr Phe Ser Asn Tyr Trp Ile Glu Trp Val Lys Gln Arg
        50                  55                  60

Pro Gly His Gly Leu Glu Trp Ile Gly Glu Ile Leu Pro Gly Thr Gly
65                  70                  75                  80

Arg Thr Ile Tyr Asn Glu Lys Phe Lys Gly Lys Ala Thr Phe Thr Ala
                85                  90                  95

Asp Ile Ser Ser Asn Thr Val Gln Met Gln Leu Ser Ser Leu Thr Ser
                100                 105                 110
```

Glu Asp Ser Ala Val Tyr Tyr Cys Ala Arg Arg Asp Tyr Tyr Gly Asn
            115                 120                 125

Phe Tyr Tyr Ala Met Asp Tyr Trp Gly Gln Gly Thr Ser Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
    195                 200                 205

Tyr Ser Leu Ser Ser Val Val Thr Val Pro Ser Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
    275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
    355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
    435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly
465                 470                 475

<210> SEQ ID NO 7
<211> LENGTH: 165
<212> TYPE: PRT
<213> ORGANISM: Artificial Sequence
<220> FEATURE:
<223> OTHER INFORMATION: Synthetic

<400> SEQUENCE: 7

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Leu Ser Gly Arg Ser Asp Asn His Gly Ser Ser Gly Thr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Thr Asp Val Asp Tyr Tyr Arg Glu Trp Ser Trp Thr Gln Val Ser
1               5                   10                  15

<210> SEQ ID NO 10
<211> LENGTH: 39
<212> TYPE: PRT
<213> ORGANISM: Artificial Sequence
<220> FEATURE:
<223> OTHER INFORMATION: Synthetic

<400> SEQUENCE: 10

Gly Gln Ser Gly Gln Thr Asp Val Asp Tyr Tyr Arg Glu Trp Ser Glu
1               5                   10                  15

Thr Gln Val Ser Gly Ser Ser Gly Gly Ser Val His Met Pro Leu Gly
            20                  25                  30

Phe Leu Gly Pro Gly Gly Ser
            35

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Val His Met Pro Leu Gly Phe Leu Gly Pro
1               5                   10

<210> SEQ ID NO 12
<211> LENGTH: 66
<212> TYPE: PRT
<213> ORGANISM: Artificial Sequence
<220> FEATURE:
<223> OTHER INFORMATION: Synthetic

<400> SEQUENCE: 12

Val Val Arg Ala Glu Ile Met Arg Ser Phe Ser Leu Ser Thr Asn Leu
1               5                   10                  15

Gln Glu Ser Leu Arg Ser Lys Glu Gly Ser Ser Gly Leu Ser Gly Arg
            20                  25                  30

Ser Asp Asn His Gly Ser Ser Gly Gly Ser Gly Gly Ser Gly Gly Ser
        35                  40                  45

Gly Thr Asp Val Asp Tyr Tyr Arg Glu Trp Ser Trp Thr Gln Val Ser
    50                  55                  60

Gly Gly
65

<210> SEQ ID NO 13
<211> LENGTH: 65
<212> TYPE: PRT
<213> ORGANISM: Artificial Sequence
<220> FEATURE:
<223> OTHER INFORMATION: Synthetic

<400> SEQUENCE: 13

Val Val Arg Ala Glu Ile Met Arg Ser Phe Ser Leu Ser Thr Asn Leu
1               5                   10                  15

Gln Glu Ser Leu Arg Ser Lys Glu Gly Ser Ser Gly Leu Ser Gly Arg
            20                  25                  30

Ser Asp Asn His Gly Ser Ser Gly Gly Ser Gly Gly Ser Gly Gly Ser
        35                  40                  45

Gly Thr Asp Val Asp Tyr Tyr Arg Glu Trp Ser Trp Thr Gln Val Gly
    50                  55                  60

Gly
65

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Thr Asp Val Asp Tyr Tyr Arg Glu Trp Ser Trp Thr Gln Val
1               5                   10

<210> SEQ ID NO 15
<211> LENGTH: 15

```
<212> TYPE: PRT
<213> ORGANISM: Artificial Sequence
<220> FEATURE:
<223> OTHER INFORMATION: Synthetic

<400> SEQUENCE: 15

Thr Asp Val Asp Tyr Tyr Arg Glu Trp Ser Trp Thr Gln Val Ser
1               5                   10                  15

<210> SEQ ID NO 16
<211> LENGTH: 25
<212> TYPE: PRT
<213> ORGANISM: Artificial Sequence
<220> FEATURE:
<223> OTHER INFORMATION: Synthetic

<400> SEQUENCE: 16

Gly Ser Ser Gly Leu Ser Gly Arg Ser Asp Asn His Gly Ser Ser Gly
1               5                   10                  15

Gly Ser Gly Gly Ser Gly Gly Ser Gly
            20                  25

<210> SEQ ID NO 17
<211> LENGTH: 688
<212> TYPE: PRT
<213> ORGANISM: Artificial Sequence
<220> FEATURE:
<223> OTHER INFORMATION: Synthetic

<400> SEQUENCE: 17

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Gln Ser Gly
                20                  25                  30

Ser Glu Leu Met Met Pro Gly Ala Ser Val Lys Ile Ser Cys Lys Ala
            35                  40                  45

Thr Gly Tyr Thr Phe Ser Asn Tyr Trp Ile Glu Trp Val Lys Gln Arg
    50                  55                  60

Pro Gly His Gly Leu Glu Trp Ile Gly Glu Ile Leu Pro Gly Thr Gly
65                  70                  75                  80

Arg Thr Ile Tyr Asn Glu Lys Phe Lys Gly Lys Ala Thr Phe Thr Ala
                85                  90                  95

Asp Ile Ser Ser Asn Thr Val Gln Met Gln Leu Ser Ser Leu Thr Ser
            100                 105                 110

Glu Asp Ser Ala Val Tyr Tyr Cys Ala Arg Arg Asp Tyr Tyr Gly Asn
        115                 120                 125

Phe Tyr Tyr Ala Met Asp Tyr Trp Gly Gln Gly Thr Ser Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
```

-continued

```
              225                 230                 235                 240
Asp Lys Lys Val Glu Pro Lys Ser Cys Asp Lys Thr His Thr Cys Pro
                245                 250                 255
Pro Cys Pro Ala Pro Glu Leu Leu Gly Gly Pro Ser Val Phe Leu Phe
                260                 265                 270
Pro Pro Lys Pro Lys Asp Thr Leu Met Ile Ser Arg Thr Pro Glu Val
                275                 280                 285
Thr Cys Val Val Val Asp Val Ser His Glu Asp Pro Glu Val Lys Phe
                290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
                340                 345                 350
Ser Asn Lys Ala Leu Pro Ala Pro Ile Glu Lys Thr Ile Ser Lys Ala
                355                 360                 365
Lys Gly Gln Pro Arg Glu Pro Gln Val Tyr Thr Leu Pro Pro Ser Arg
370                 375                 380
Asp Glu Leu Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
                420                 425                 430
Phe Phe Leu Tyr Ser Lys Leu Thr Val Asp Lys Ser Arg Trp Gln Gln
                435                 440                 445
Gly Asn Val Phe Ser Cys Ser Val Met His Glu Ala Leu His Asn His
                450                 455                 460
Tyr Thr Gln Lys Ser Leu Ser Leu Ser Pro Gly Ser Gly Gly Gly Gly
465                 470                 475                 480
Ser Cys Asp Leu Pro Gln Thr His Ser Leu Gly Ser Arg Arg Thr Leu
                485                 490                 495
Met Leu Leu Ala Gln Met Arg Arg Ile Ser Leu Phe Ser Cys Leu Lys
                500                 505                 510
Asp Arg His Asp Phe Gly Phe Pro Gln Glu Glu Phe Gly Asn Gln Phe
                515                 520                 525
Gln Lys Ala Glu Thr Ile Pro Val Leu His Glu Met Ile Gln Gln Ile
                530                 535                 540
Phe Asn Leu Phe Ser Thr Lys Asp Ser Ser Ala Ala Trp Asp Glu Thr
545                 550                 555                 560
Leu Leu Asp Lys Phe Tyr Thr Glu Leu Tyr Gln Gln Leu Asn Asp Leu
                565                 570                 575
Glu Ala Cys Val Ile Gln Gly Val Gly Val Thr Glu Thr Pro Leu Met
                580                 585                 590
Lys Glu Asp Ser Ile Leu Ala Val Arg Lys Tyr Phe Gln Arg Ile Thr
                595                 600                 605
Leu Tyr Leu Lys Glu Lys Lys Tyr Ser Pro Cys Ala Trp Glu Val Val
                610                 615                 620
Arg Ala Glu Ile Met Arg Ser Phe Ser Leu Ser Thr Asn Leu Gln Glu
625                 630                 635                 640
Ser Leu Arg Ser Lys Glu Gly Ser Ser Gly Leu Ser Gly Arg Ser Asp
                645                 650                 655
```

-continued

Asn His Gly Ser Ser Gly Gly Ser Gly Gly Ser Gly Thr
            660             665             670

Asp Val Asp Tyr Tyr Arg Glu Trp Ser Trp Thr Gln Val Ser Gly Gly
        675             680             685

<210> SEQ ID NO 18
<211> LENGTH: 664
<212> TYPE: PRT
<213> ORGANISM: Artificial Sequence
<220> FEATURE:
<223> OTHER INFORMATION: Synthetic

<400> SEQUENCE: 18

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

```
Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Ser Gly Gly Gly Ser Cys Asp Leu Pro Gln Thr His
            450                 455                 460

Ser Leu Gly Ser Arg Arg Thr Leu Met Leu Leu Ala Gln Met Arg Arg
465                 470                 475                 480

Ile Ser Leu Phe Ser Cys Leu Lys Asp Arg His Asp Phe Gly Phe Pro
            485                 490                 495

Gln Glu Glu Phe Gly Asn Gln Phe Gln Lys Ala Glu Thr Ile Pro Val
            500                 505                 510

Leu His Glu Met Ile Gln Gln Ile Phe Asn Leu Phe Ser Thr Lys Asp
            515                 520                 525

Ser Ser Ala Ala Trp Asp Glu Thr Leu Leu Asp Lys Phe Tyr Thr Glu
530                 535                 540

Leu Tyr Gln Gln Leu Asn Asp Leu Glu Ala Cys Val Ile Gln Gly Val
545                 550                 555                 560

Gly Val Thr Glu Thr Pro Leu Met Lys Glu Asp Ser Ile Leu Ala Val
            565                 570                 575

Arg Lys Tyr Phe Gln Arg Ile Thr Leu Tyr Leu Lys Glu Lys Lys Tyr
            580                 585                 590

Ser Pro Cys Ala Trp Glu Val Val Arg Ala Glu Ile Met Arg Ser Phe
            595                 600                 605

Ser Leu Ser Thr Asn Leu Gln Glu Ser Leu Arg Ser Lys Glu Gly Ser
            610                 615                 620

Ser Gly Leu Ser Gly Arg Ser Asp Asn His Gly Ser Ser Gly Gly Ser
625                 630                 635                 640

Gly Gly Ser Gly Gly Ser Gly Thr Asp Val Asp Tyr Tyr Arg Glu Trp
            645                 650                 655

Ser Trp Thr Gln Val Ser Gly Gly
            660

<210> SEQ ID NO 19
<211> LENGTH: 18
<212> TYPE: PRT
<213> ORGANISM: Artificial Sequence
<220> FEATURE:
<223> OTHER INFORMATION: Synthetic

<400> SEQUENCE: 19

Gly Ser Gly Thr Asp Val Asp Tyr Tyr Arg Glu Trp Ser Trp Thr Gln
1               5                   10                  15

Val Ser
```

```
<210> SEQ ID NO 20
<211> LENGTH: 17
<212> TYPE: PRT
<213> ORGANISM: Artificial Sequence
<220> FEATURE:
<223> OTHER INFORMATION: Synthetic

<400> SEQUENCE: 20

Gly Ser Gly Thr Asp Val Asp Tyr Tyr Arg Glu Trp Ser Trp Thr Gln
1               5                   10                  15

Val

<210> SEQ ID NO 21
<211> LENGTH: 451
<212> TYPE: PRT
<213> ORGANISM: Artificial Sequence
<220> FEATURE:
<223> OTHER INFORMATION: Synthetic

<400> SEQUENCE: 21

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

```
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

UNITED STATES PATENT AND TRADEMARK OFFICE
CERTIFICATE OF CORRECTION

PATENT NO. : 11,136,353 B2  
APPLICATION NO. : 16/849889  
DATED : October 5, 2021  
INVENTOR(S) : David Stover et al.

It is certified that error appears in the above-identified patent and that said Letters Patent is hereby corrected as shown below:

In the Claims

At Column 64, Claim number 17, Line number 63, "whereby said interferon mask." should read -- whereby said interferon mask is attached at the C-terminal of said Type-I interferon. --.

Signed and Sealed this  
Twenty-seventh Day of June, 2023

Katherine Kelly Vidal  
*Director of the United States Patent and Trademark Office*